(12) United States Patent
Gothelf et al.

(10) Patent No.: US 10,925,970 B2
(45) Date of Patent: Feb. 23, 2021

(54) SITE SELECTIVE CONJUGATION OF AN OLIGONUCLEOTIDE CONJUGATE OR A SMALL MOLECULE TO A METAL BINDING PROTEIN

(71) Applicant: AFFYCON APS, Risskov (DK)

(72) Inventors: Kurt Vesterager Gothelf, Risskov (DK); Thomas Torring, Aarhus (DK); Christian Bech Rosen, Berkeley, CA (US); Anne Louise Bank Kodal, Aarhus (DK); Michael Rosholm Mortensen, Aarhus (DK)

(73) Assignee: Affycon ApS, Risskov (DK)

( * ) Notice: Subject to any disclaimer, the term of this patent is extended or adjusted under 35 U.S.C. 154(b) by 235 days.

(21) Appl. No.: 15/500,019

(22) PCT Filed: Jul. 8, 2015

(86) PCT No.: PCT/EP2015/065643
§ 371 (c)(1),
(2) Date: Jan. 27, 2017

(87) PCT Pub. No.: WO2016/005474
PCT Pub. Date: Jan. 14, 2016

(65) Prior Publication Data
US 2017/0354743 A1 Dec. 14, 2017

(30) Foreign Application Priority Data
Jul. 8, 2014 (DK) .......................... PA 2014 70427

(51) Int. Cl.
*C12Q 1/68* (2018.01)
*A61K 47/68* (2017.01)
*A61K 47/64* (2017.01)

(52) U.S. Cl.
CPC .......... *A61K 47/6807* (2017.08); *A61K 47/64* (2017.08); *A61K 47/644* (2017.08); *A61K 47/6803* (2017.08)

(58) Field of Classification Search
CPC .................................................. A61K 47/6807
USPC ....................................................... 435/6.1
See application file for complete search history.

(56) References Cited

PUBLICATIONS

EP Patent Appln. No. 15738877.8, Communication dated May 29, 2019.
Barbuto et al. (2013) "Induction of Innate and Adaptive Immunity by Delivery of Poly dA:dT to Dendritic Cells", Nat. Chem. Biol. 9:250-256.
Corey et al. (1987) "Generation of a Hybrid Sequence-specific Single-stranded Deoxyribonuclease", Science 238:1401-1403.
Gautier et al. (2008) "An Engineered Protein Tag for Multiprotein Labeling in Living Cells", Chem. Biol. 15:128-136.
Howorka et al. (2001) "Sequence-specific Detection of Individual DNA Strands Using Engineered Nanopores", Nat. Biotechnol. 19:636-639.
Hughes et al. (2009) "Marinopyrrole A Target Elucidation by Acyl Sye Transfer", J. Am. Chem. Soc. 131:12094-12096.
Kazane et al. (2012) "Site-specific DNA-antibody Conjugates for Specific and Sensitive Immuno-PCR", Proc. Natl. Acad. Sci. U.S.A. 109:3731-3736.
Kazane et al. (2013) "Self-assembled Antibody Multimers Through Peptide Nucleic Acid Conjugation", J. Am. Chem. Soc. 135:340-346.
Keppler et al. (2003) "A General Method for the Covalent Labeling of Fusion Proteins with Small Molecules in Vivo", Nat. Biotechnol. 21:86-89.
Koshi et al. (2008) "Target-specific Chemical Acylation of Lectins by Ligand-tethered DMAP Catalysts", J. Am. Chem. Soc. 130:245-251.
Li et al. (2004) "DNA-templated Organic Synthesis: Nature's Strategy for Controlling Chemical Reactivity Applied to Synthetic Molecules", Angew. Chem. Int. Ed. 43:4848-4870.
Li et al. (2013) "Photoaffinity Labeling of Small-molecule-binding Proteins by DNA-templated Chemistry", Angew. Chem. Int. Ed. 52:9544-9549.
Liu et al., (2010) "DNA-Templated Covalent Coupling of G4 PAMAM Dendrimers", J. Amer. Chem. Soc. 132:18054-18056.
Los et al. (2008) "HaloTag: A Novel Protein Labeling Technology for Cell Imaging and Protein Analysis", ACS Chem. Biol. 3:373-382.
Meredith et al. (2004) "Targeted Protein Functionalization Using His-tags", Bioconjugate Chem. 15:969-982.
Netirojjanakul et al. (2013) "Synthetically Modified Fc Domains as Building Blocks for Immunotherapy Applications", Chem. Sci. 4:266-272.
Niemeyer et al. (1994) "Oligonucleotide-directed Self-assembly of Proteins: Semisynthetic DNA-streptavidin Hybrid Molecules as Connectors for the Generation of Macroscopic Arrays and the Construction of Supramolecular Bioconjugates", Nucl. Acids Res. 22:5530-5539.
Niemeyer (2010) "Semisynthetic DNA-protein Conjugates for Biosensing and Nanofabrication", Angew. Chem. Int. Ed. 49:1200-1216.
Rabuka et al. (2012) "Site-specific Chemical Protein Conjugation Using Genetically Encoded Aldehyde Tags", Nat. Protoc. 7:1052-1067.
Rosen et al. (2014) "Template-directed Covalent Conjugation of DNA to Native Antibodies, Transferrin and Other Metal-binding Proteins", Nature Chem. 6: 804-809.
Saghatelian et al. (2003) "DNA Detection and Signal Amplification Via an Engineered Allosteric Enzyme", J. Am. Chem. Soc. 125:344-345.
Stephanopoulos et al. (2011) "Choosing an Effective Protein Bioconjugation Strategy", Nat. Chem. Biol. 7:876-884.
Tsukiji et al. (2009) "Ligand-directed Tosyl Chemistry for Protein Labeling in Vivo", Nat. Chem. Biol. 5:341-343.

(Continued)

*Primary Examiner* — Jezia Riley
(74) *Attorney, Agent, or Firm* — Cheryl H. Agris; Agris & von Natzmer, LLP

(57) ABSTRACT

Provided are methods for site selective conjugation of an oligonucleotide conjugate to a metal binding protein comprising a metal binding site and for site selective conjugation of a small molecule conjugation compound (SMCoC) to an antibody comprising a metal binding site, metal binding protein conjugates obtainable by said methods, and uses of said metal binding protein conjugates.

45 Claims, 45 Drawing Sheets

Figure 1:
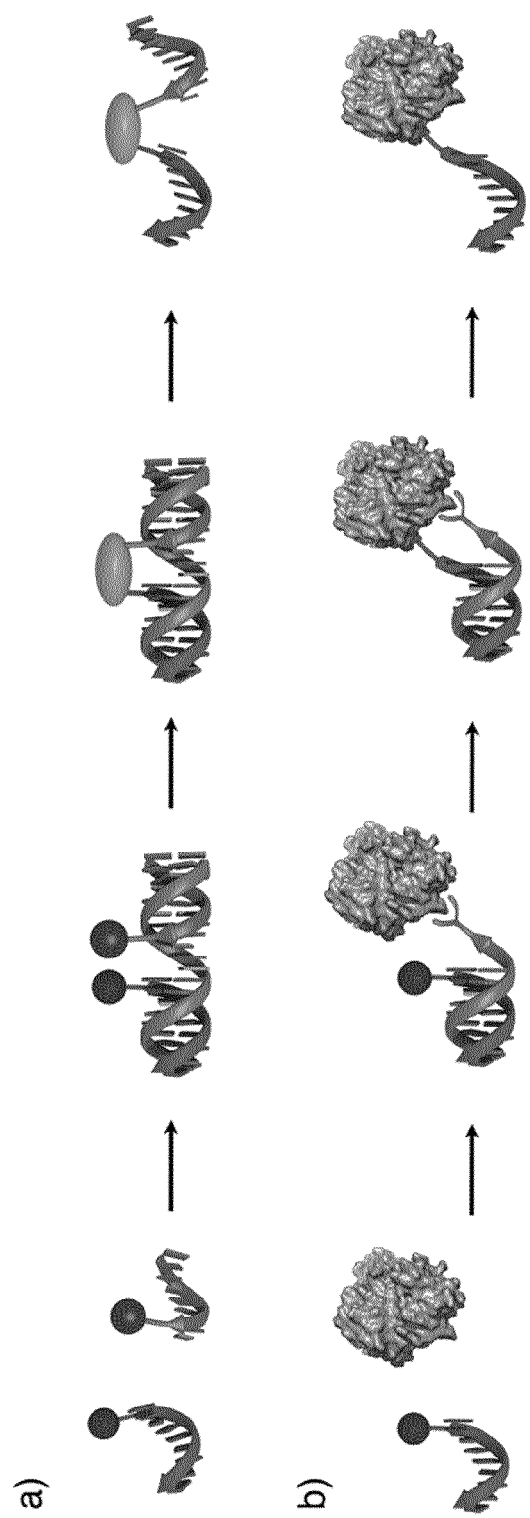

Specification includes a Sequence Listing.

(56) References Cited

PUBLICATIONS

Uchinomiya et al. (2009) "Site-specific Covalent Labeling of His-tag Fused Proteins with a Reactive Ni(II)-NTA Probe", Chem. Commun. 5880-5882.
Vinkenborg et al. (2012) "Aptamer-based Afinity Labeling of Proteins", Angew. Chem. Int. Ed. 51:9176-9180.
EP Patent Appln. No. 15738877.8, Amended Claims, Submitted Oct. 18, 2017.
PCT Appln. No. PCT/EP2015/065643, International Preliminary Report on Patentability, dated Jan. 10, 2017.
PCT Appln. No. PCT/EP2015/065643, International Search Report and Written Opinion, dated Oct. 7, 2015.

Serotransferrin n=1-4, m=1-4

GFP
SDS-PAGE

Transferrin
SDS-PAGE

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
acatacagcc tcgcatgagc cc                                          22

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide

<400> SEQUENCE: 2
gggctcatgc gaggcttacg aac                                         23

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide

<400> SEQUENCE: 3
gggctcatgc gaggctgtat gt                                          22

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
gttcgtaagc ctcgcatgag ccc                                         23
```

SITE SELECTIVE CONJUGATION OF AN OLIGONUCLEOTIDE CONJUGATE OR A SMALL MOLECULE TO A METAL BINDING PROTEIN

FIELD OF THE INVENTION

The present invention relates to methods for site selective conjugation of an oligonucleotide conjugate or a molecule to a metal binding protein, metal binding protein conjugates obtainable by said methods and uses of said metal binding protein conjugates.

BACKGROUND OF THE INVENTION

DNA-protein conjugates are important in bioanalytical chemistry, molecular diagnostics and bionanotechnology, where the DNA provides a unique handle to identify, functionalize or manipulate proteins. In order to maintain protein activity, site-selective conjugation is frequently required. However, the preparation of such high quality conjugates most often requires genetically engineered proteins, which is a laborious and technically challenging approach.

Protein bioconjugation (1,2) with DNA has typically been approached by expressing the protein of interest with a chemical handle, such as recombinant insertion of a cysteine residue. This has been applied for modifications of e.g. nucleases (3), proteases (4), and membrane pores (5). Cysteines can additionally be enzymatically transformed into useful aldehyde handles when expressed as a part of the peptide sequence recognized by formylglycine generating enzyme (FGE) (6). Furthermore, Schultz and coworkers have recently reported on the incorporation of an unnatural p-acetylphenylalanine amino acid for site-specific attachment of DNA to antibodies (7,8), and Francis and coworkers have demonstrated pyridoxal-5'-phosphate (PLP) mediated transamination of an inserted N-terminal tripeptide sequence to obtain site-specific DNA conjugation to antibody Fc domains (9). Muir and co-workers recently developed a protein-DNA ligation strategy based on expressed protein ligation (10). In relation to these, a widely applied method is the use of commercial fusion protein kits consisting of the protein of interest and Snap-Tags® (11), HaloTags®12 or CLIP-Tags™ (13).

As an alternative to genetic manipulation, wild-type proteins can be treated with a large excess of a non-selective small molecule linker, typically targeting multiple lysine residues on the protein surface. Such approaches of global residue-specific labeling has been pioneered by Niemeyer et al. by reacting streptavidin with an excess of a heterobifunctional linker (14). In this method, one end of the linker is covalently attached to the lysine side chains while the other end, consisting of a maleimide functionality, is subsequently coupled to thiolated DNA strands. Considerable disadvantages of using an unspecific global labeling method are the inability to control labeling stoichiometry as well as the potential loss or alteration of protein function (7).

In general, the methods that enable formation of a single conjugate product accordingly require genetically engineered proteins. In contrast, the approaches that use wild-type proteins inevitably result in a mixture of products. The choice is therefore often between a more cumbersome recombinant protein expression strategy and a heterogeneous mixture of products. An interesting alternative approach that has been used for labeling of proteins with small molecules, is employing a protein substrate or the nickel complex of nitrilotriacetic acid (NTA) to guide a tethered functional group to react with the protein (15-19). Very recently, Li and coworkers applied small-molecule-DNA constructs for the purpose of identifying target proteins in a cell lysate using DNA-directed chemistry and photoreactive groups (20). Mayer and coworkers have also previously employed photoreactive aptamers as a tool to identify potential off-targets (21).

SUMMARY OF THE INVENTION

An object of the present invention is to provide a method for site selective conjugation of DNA conjugates to metal binding proteins as well as site selective conjugation of small molecules to metal binding proteins such as for example antibodies.

A first aspect of the present invention relates to a method for site selective conjugation of an oligonucleotide conjugate to a metal binding protein comprising a metal binding site, said method comprising:
providing a first oligonucleotide conjugate comprising a compound that comprises a reactive chemical group capable of reacting with a nucleophilic amino acid residue in the vicinity of said metal binding site of said metal binding protein,
providing a second oligonucleotide conjugate capable of hybridizing to said first oligonucleotide conjugate and wherein said second oligonucleotide is conjugated to at least one ligand capable of binding a metal at said metal binding site,
contacting said metal binding protein with said first oligonucleotide and said second oligonucleotide,
whereby hybridization of the first oligonucleotide conjugate to the second oligonucleotide conjugate and binding of the ligand to the metal binding site guides the reactive chemical group of the first oligonucleotide conjugate into proximity with the nucleophilic amino acid residue in a nucleophilic reaction between the nucleophilic amino acid residue and the reactive group of the first oligonucleotide conjugate, thereby conjugating the first oligonucleotide conjugate to the metal binding protein.

A second aspect of the present invention relates to a method for site selective conjugation of a small molecule conjugation compound (SMCoC) to an antibody comprising a metal binding site, said method comprising
a) providing an antibody comprising a metal binding site;
b) providing a small molecule conjugation compound (SMCoC) comprising or consisting of the structure of Formula 1:

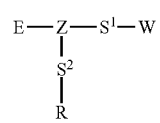

Formula 1 or a salt and/or hydrate thereof;
wherein:
E is an electrophile,
Z is a moiety that connects E, $S^1$, and $S^2$ or R; or is absent, in which case $S^1$ is directly connected to E,
R is a reactive chemical group that can couple to another compound, or is absent,
$S^1$ is a linker, optionally a cleavable linker,
$S^2$ is a linker, optionally a cleavable linker, or is absent, W is one or more covalently interlinked ligands L capable of binding one or more metal ions at a metal binding site of said metal binding antibody; and c) contacting said metal binding antibody with said SMCoC;

whereby binding of W to the metal binding site of the antibody via metal coordination guides E into proximity with a nucleophilic amino acid residue of the antibody, resulting in a nucleophilic reaction between the nucleophilic amino acid residue and the electrophile E, thereby conjugating SMCoC to the antibody.

Another aspect of the present invention relates to a metal binding protein conjugate obtainable by the methods described herein.

A further aspect of the present invention relates to the use of the metal binding protein conjugates of the present invention, e.g. in immuno-PCR, targeted gene silencing, DNA-sensor technology, DNA-PAINT superresolution microscopy, RNAi delivery, as PET contrast agents, for radioimmunotherapy, diagnostics and drug delivery.

DRAWING DESCRIPTION

FIG. 1. Expanding the concept of DNA templated synthesis. a, Two non-complementary DNA ONs with compatible functional groups will not react when highly diluted (nanomolar). By adding a templating ON capable of binding to both ONs the reactive species will come into close proximity, thereby facilitating a reaction. b, A chemically activated ON is site-specifically directed to a protein by a non-covalent template-facilitated reaction.

Figure 2:
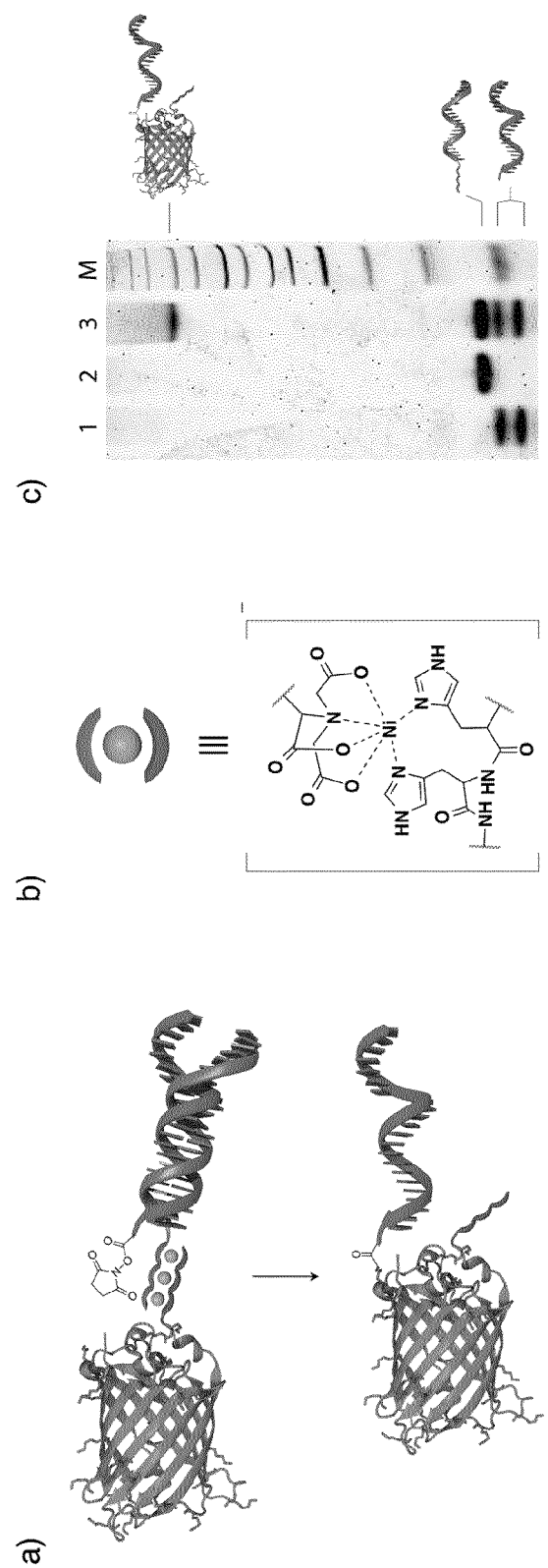

FIG. 2. Site-selective DNA-directed coupling of an activated ester to his6-tagged green fluorescent protein. a, Assembly of the reaction complex (PDB entry 1GFL). After successful reaction, the DNA protein complex can be purified. b, A single NTA functionality coordinating two histidine residues through a Ni(II) complex. The Guiding ON is modified with three NTA moieties facilitating a nanomolar binding affinity to his6 tags. c, Denaturing PAGE showing that a protein-DNA conjugate is only formed in the presence of the Guiding ON. Lane 1 GFP, Reacting ON and $NiCl_2$; 2 GFP, Guiding ON and $NiCl_2$; 3 GFP, Reacting ON and Guiding ON in the presence of $NiCl_2$; M DNA marker 25-500 bp. The gel is stained for nucleic acids with SYBR® Gold.

Figure 3:
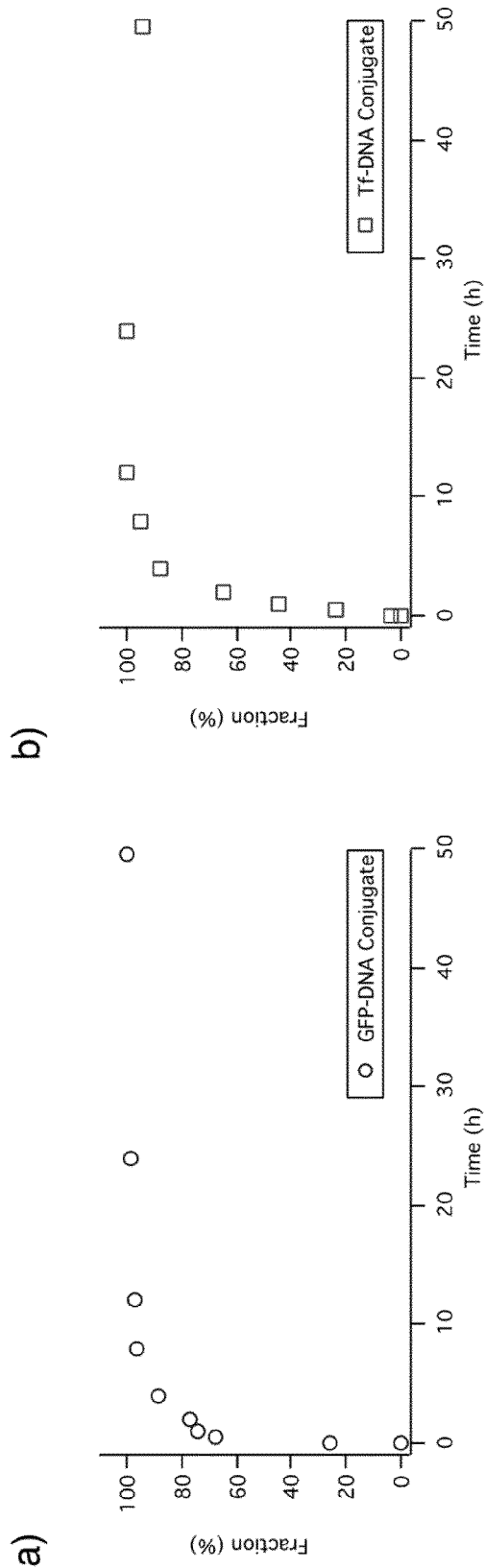

FIG. 3. Kinetics of product formation for labeling of his6-GFP and Tf using DTPC. a, Plot of product band intensities of GFP-DNA conjugates (normalized) from denaturing PAGE (6%) analysis over 49.5 hours. b, Same experiment for Tf. The results show that overnight conjugation reaction is preferable.

Figure 4:
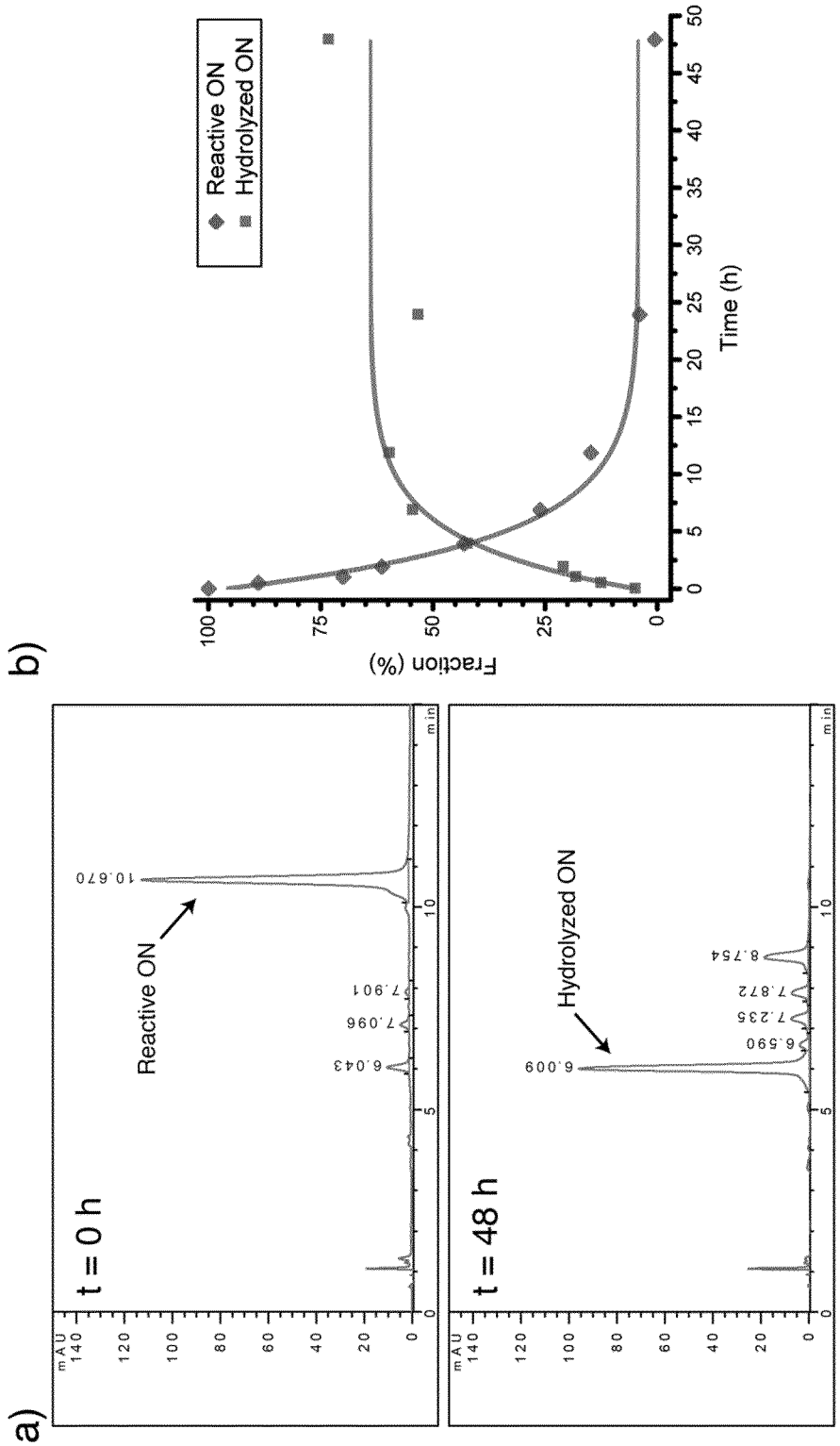

FIG. 4. Rate of hydrolysis of the NHS ester of the Reacting ON. a, Two representative chromatograms (t=0 h and t=48 h). The peak eluting at approx. 10.7 min. is the Reacting ON (containing the NHS ester). The peak eluting at approx. 6.0 min. is the corresponding carboxylic acid (hydrolyzed NHS ester). The peaks eluting between the two identified peaks are unidentified byproducts. b, The area of the Reacting ON peak and the area of carboxylic acid peak from RP-HPLC analysis plotted as a function of time. Similarly these results suggest that overnight reactions are preferable. The data corresponds well with the fact that PAGE analysis of reaction mixtures shows two distinct bands from the Reacting ON. We have determined that the lower of these are the carboxylic acid ON.

Figure 5:
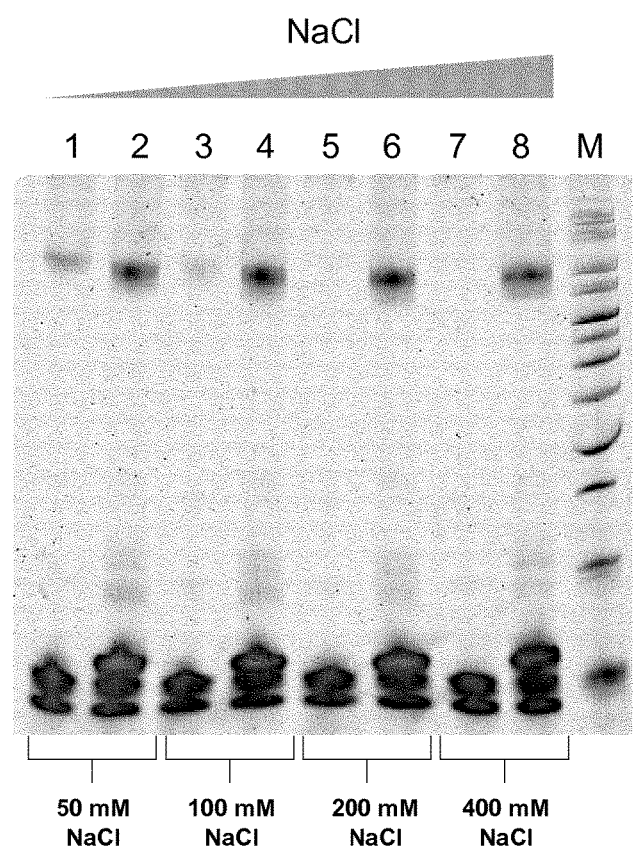

FIG. 5. Salt-dependency on unspecific labeling obtained by DTPC procedure. Denaturing PAGE (7%) analysis of DTPC performed on his6-tagged GFP at different NaCl concentrations. At increased salt concentrations less unspecific labeling is observed. Protein and Guiding ON are added in 1.2 eq. compared to Reacting ON and $NiCl_2$ are used in 5 eq. compared to Reacting ON. Lane (1) GFP, Reacting ON, $NiCl_2$ and 50 mM NaCl, (2) GFP, Reacting ON, Guiding ON, $NiCl_2$ and 50 mM NaCl, (3) GFP, Reacting ON, $NiCl_2$ and 100 mM NaCl, (4) GFP, Reacting ON, Guiding ON, $NiCl_2$ and 100 mM NaCl, (5) GFP, Reacting ON, $NiCl_2$ and 200 mM NaCl, (6) GFP, Reacting ON, Guiding ON, $NiCl_2$ and 200 mM NaCl, (7) GFP, Reacting ON, $NiCl_2$ and 400 mM NaCl, (8) GFP, Reacting ON, Guiding ON, NiCl2 and 400 mM NaCl, (M) DNA marker 25-500 bp (Bioline). The gel is stained for nucleic acids with SYBR® Gold.

Figure 6:
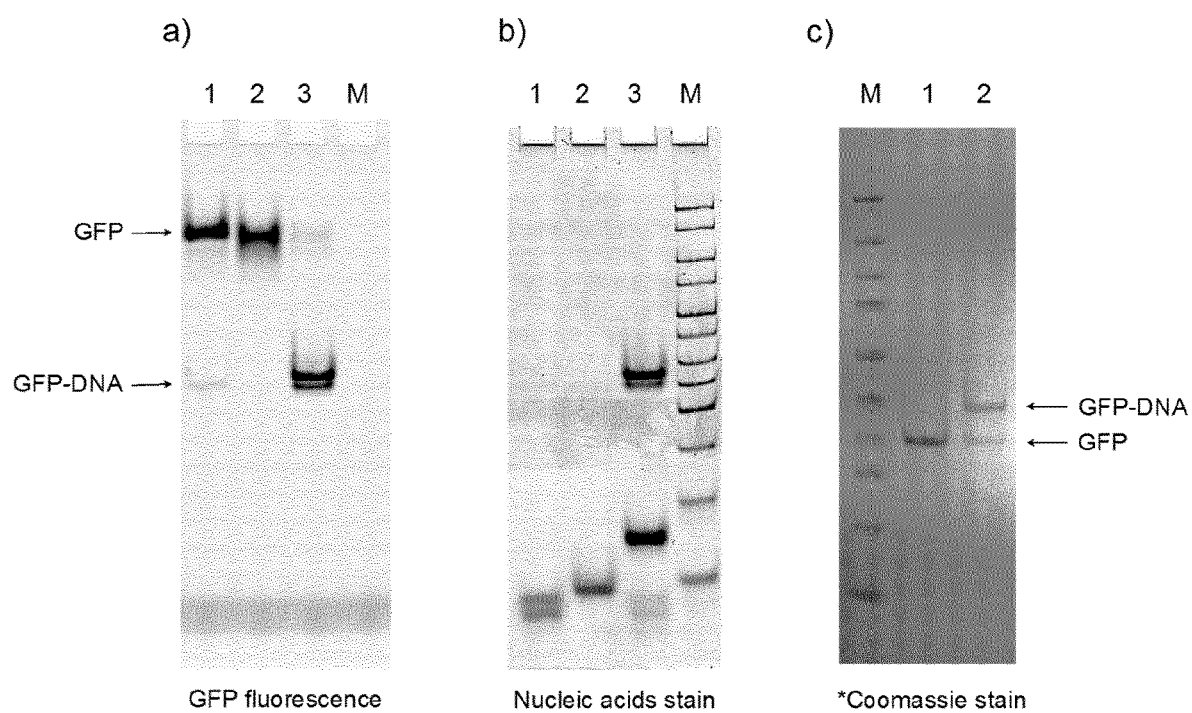

FIG. 6. DNA templated labeling of his6-tagged GFP showing nearly full conversion when comparing GFP fluorescence. a, GFP fluorescence scan of non-denaturing 6% PAGE showing nearly complete conversion to the conjugation product in the presence of templating ON. Lane (1) GFP, Reacting ON and NiCl2, (2) GFP, Guiding ON and NiCl2, (3) GFP, Reacting ON and Guiding ON in the presence of NiCl2, (M) DNA marker 25-500 bp (Bioline). b, Same gel as a, stained for nucleic acids with SYBR® Gold. Note that GFP was purchased as estimated 70% pure by the supplier. c, SDS-PAGE (4-12%) of the conjugate. Lane (M) SeeBlue® Plus2 Prestained protein marker (Life Technologies), (1) GFP, (2) GFP, Reacting ON and Guiding ON in the presence of NiCl2. *N.B. Proteins were visualized by Coomassie staining, which does not provide a quantitative readout, since the DNA conjugate does not stain as efficiently as proteins alone (see FIG. 24).

Figure 7:
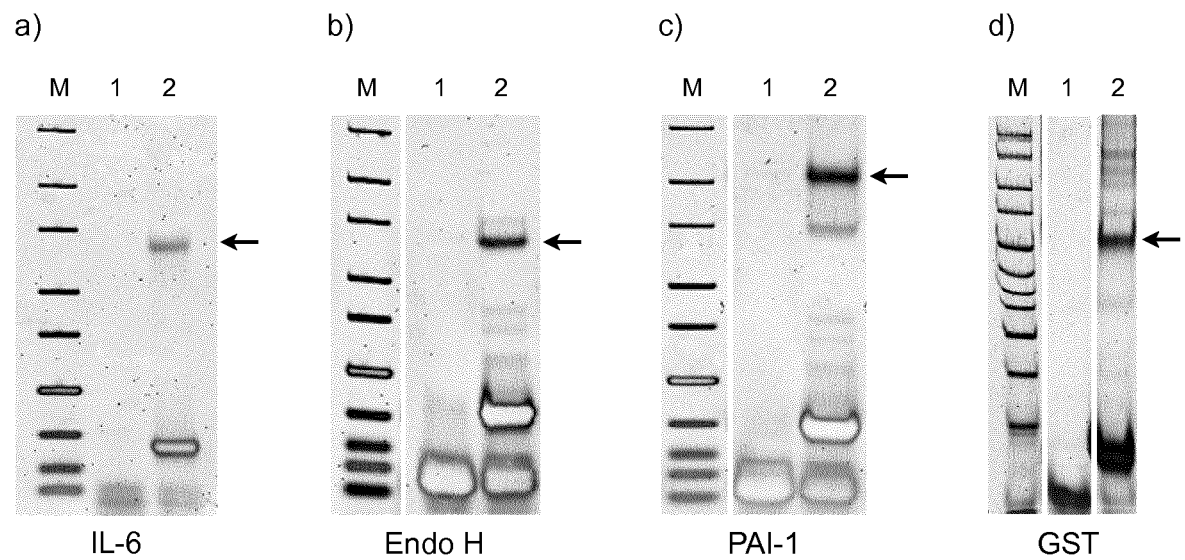

FIG. 7. Non-denaturing 6% PAGE showing DNA templated labeling of his6-tagged proteins. a, ON conjugation to N-terminal his6-tagged interleukin-6 (IL-6). b, C-terminal his6-tagged endoglycosidase H (Endo H). c, N-terminal his6-tagged plasminogen activator inhibitor-1 (PAI-1). d, N-terminal his6-tagged glutathione S-transferase (GST). a-d, Lane (M) DNA markers (a-c, 25-500 bp (Bioline); d, O'GeneRuler™ Ultra Low Range (Fermentas)), (1) his6-tagged protein, Reacting ON and NiCl2, (2) his6-tagged protein, Reacting ON and Guiding ON in the presence of NiCl2. The gels are stained for nucleic acids with SYBR® Gold. Arrows indicate single-ON-protein product band.

Figure 8:
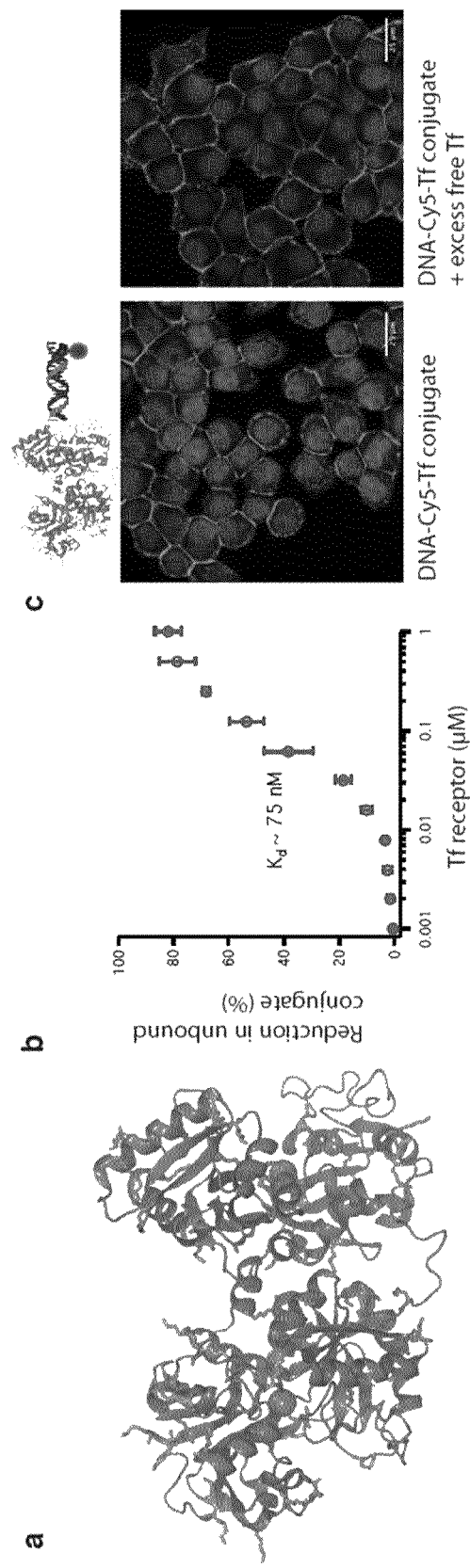

FIG. 8. DTPC labeling of Tf and cellular uptake of the conjugate. a, Crystal structure of human Tf (PDB entry 3QYT). b, Binding affinity of DNA-Tf conjugate with the Tf receptor. The Kd is estimated to 80 nM. c, (left) KB cells incubated with a Cy5-labeled DNA-Tf conjugate, (right) same experiment but with a tenfold excess of native Tf. The results reveal receptor-mediated uptake of the protein conjugates. Cell nuclei were stained with DAPI, and cell membranes were visualized using WGA Alexa Fluor® 488 Conjugate.

Figure 9:
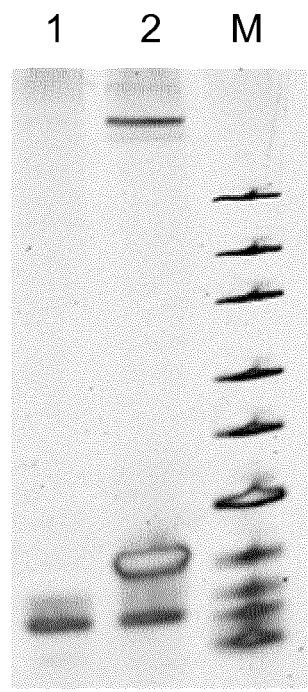

FIG. 9. Denaturing 6% PAGE showing DNA templated labeling of serotransferrin (Tf). Lane (M) DNA O'GeneRuler™ Ultra Low Range marker (Fermentas), (1) Tf, Reacting ON and NiCl2, (2) Tf, Reacting ON and Guiding ON in the presence of NiCl2. The gel is stained for nucleic acids with SYBR® Gold.

Figure 10:
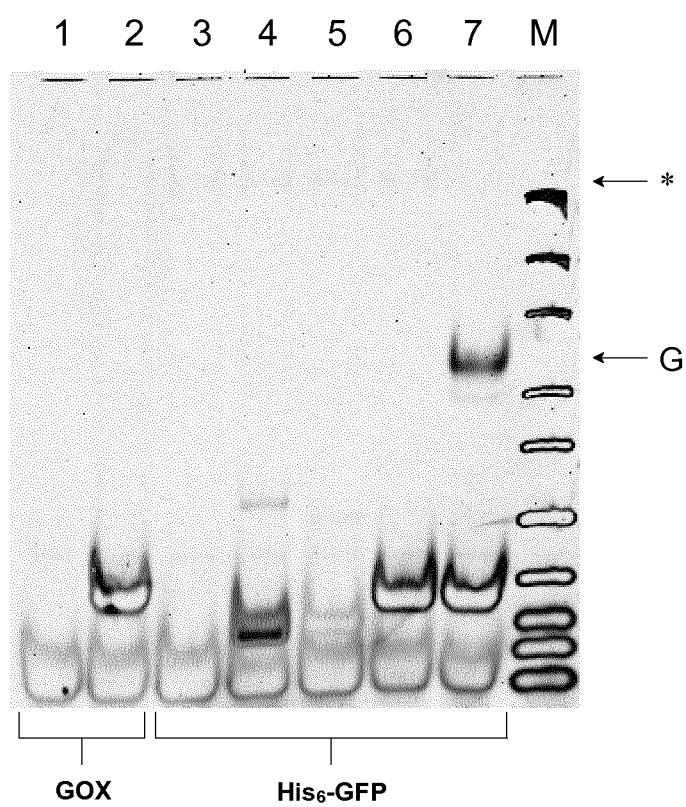

FIG. 10. Control experiments of DNA templated conjugation. Non-denaturing PAGE (6%) analysis showing that only a metal-binding protein is labeled and only when using a fully complementary Guiding ON in the presence of metal ions. Glucose oxidase (GOX) does not bind $Ni^{2+}$ and is accordingly not labeled using DTPC. Lane (1) GOX, Reacting ON and 3 eq. $NiCl_2$, (2) GOX, Reacting ON and Guiding ON in the presence of 3 eq. NiCl$_2$, (3) his$_6$-GFP, Reacting ON and 3 eq. NiCl$_2$, (4) his$_6$-GFP, Reacting ON and a Non-Guiding ON (complementary to Reacting ON but does not contain the tris(NTA) moiety) in the presence of 3 eq. NiCl$_2$, (5) his$_6$-GFP, Reacting ON and a mismatched Guiding ON (contains the tris(NTA) moiety but non-complementary to the Reacting ON) in the presence of 3 eq. NiCl$_2$, (6) his$_6$-GFP, Reacting ON and Guiding ON in the presence of 2.5 mM EDTA (no NiCl$_2$ added), (7) his$_6$-GFP, Reacting ON and Guiding ON in the presence of 3 eq. NiCl$_2$, (M) DNA markers (O'GeneRuler™ Ultra Low Range (Fermentas)). The gel is stained for nucleic acids with SYBR® Gold.

N.B. The very weak slow-migrating band in lane (3)-(6) arises from the fluorescence of non-labeled GFP.

Figure 11:
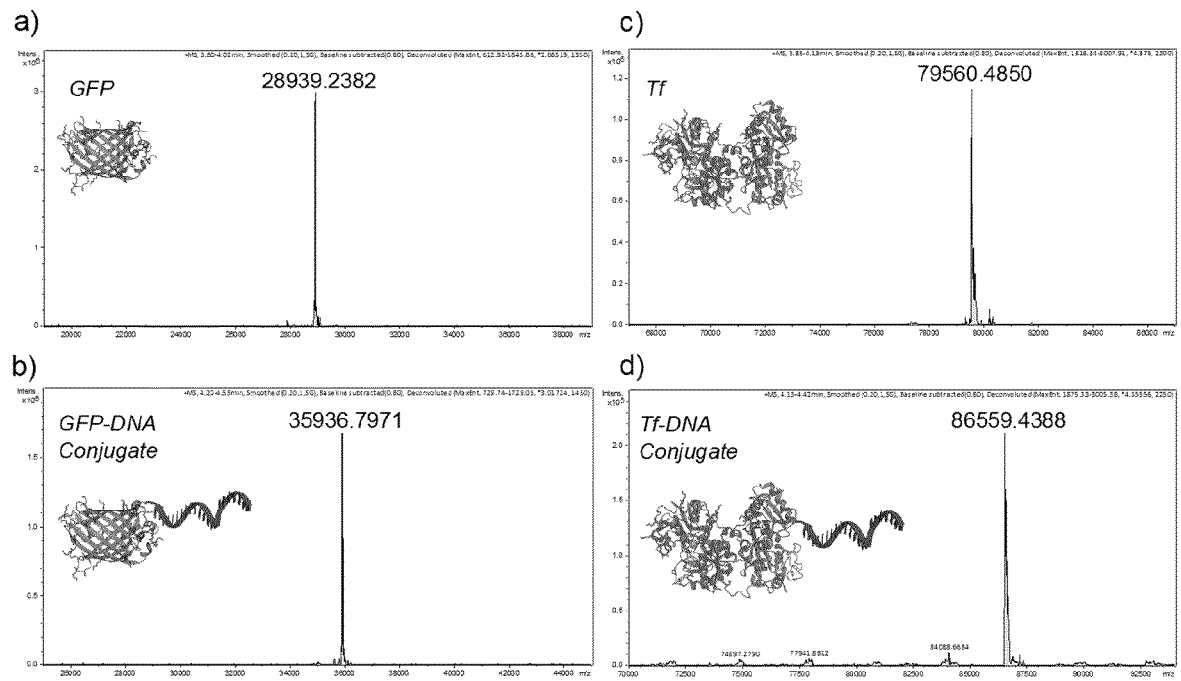

FIG. 11. Mass Spectrometry data on purified intact GFP and Tf conjugates produced by DTPC showing that only a single ON is conjugated. Deconvoluted electrospray ionization mass spectrometry data for; a, his6-GFP; b, his6-GFP-DNA conjugate; c, Tf; and d, Tf-DNA conjugate. The added molecular weight of a single DNA strand is 7000 Da (calc.). Δmass GFP (found)=35937 Da−28939 Da=6998 Da Δmass Tf (found)=86559 Da−79560 Da=6999 Da FIG. 12. Evaluation of attachment sites by MS/MS analysis of purified conjugates. a, Conjugation sites on GFP, where the greyscale colors specify the count of individual lysines identified from 5 different MS/MS experiments. b, Attachment sites on Tf, where the colors specify the count of individual lysines identified from 7 different MS/MS experiments. c, Conjugation sites on monoclonal IgG1 (mouse) Fc domain from 1 MS/MS experiment. The dark lysines indicate the specific conjugation sites. All histidine residues are marked to indicate the metal-coordinating domain. Note that a single additional hit was found on a lysine on the light chain variable region.

Figure 13:
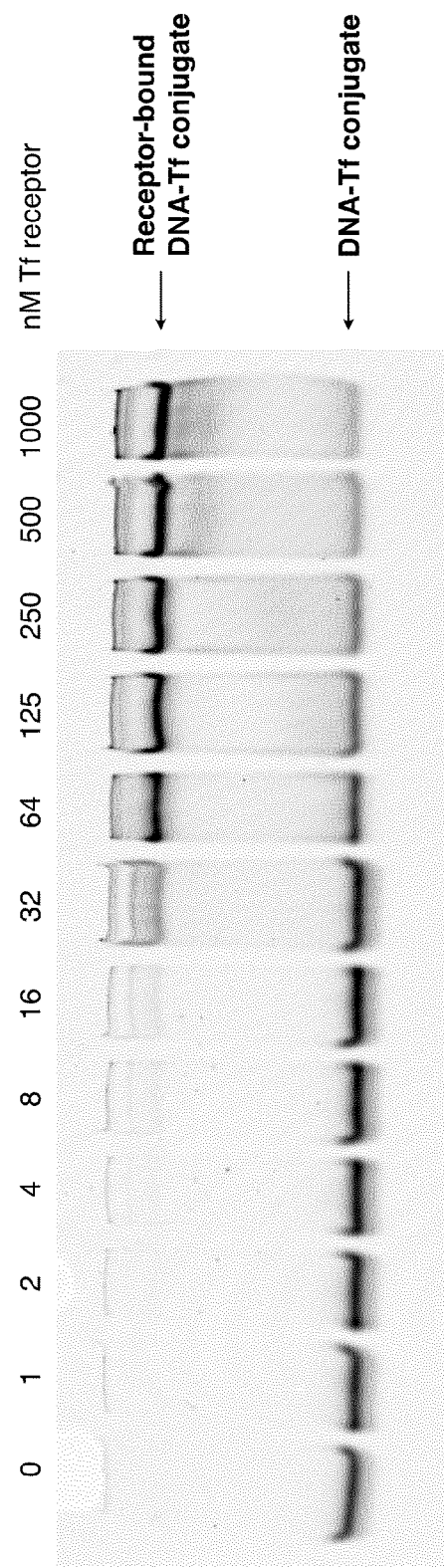

FIG. 13. Tf receptor binding assay. Representative data used for the plot in FIG. 8b. PAGE (6%, tris-borate) showing the increased formation of a conjugate-receptor complex as more Tf receptor is added to the DNA-Tf conjugate. The DNA-Tf conjugate is hybridized to a complementary Cy5-labeled ON prior to the receptor binding titration analysis. The gel bands are visualized from Cy5 fluorescence. In FIG. 3b the percentage reduction in the DNA-Tf conjugate band (fastest migrating band) was plotted as a function of added Tf receptor. By fitting to a modified Hill equation Kd could be estimated to ~75 nM. The experiment was performed 3 times to give the error bars in FIG. 8b.

Figure 14:
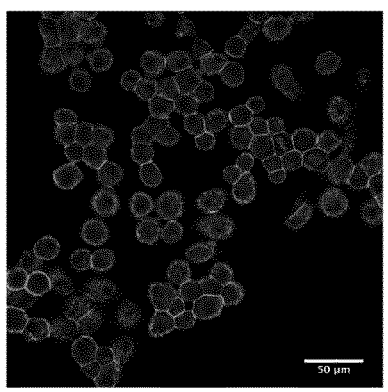
Figure 14:
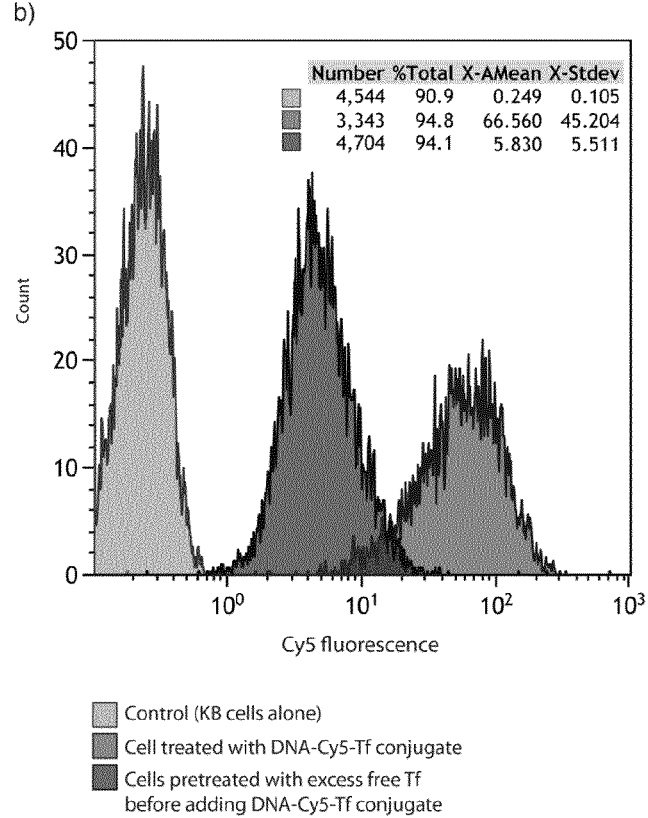

FIG. 14. Cellular uptake of DNA-Cy5-Tf conjugate. a, Similar to FIG. 8c. (top) KB cells incubated with Cy5-DNA-hybrid Tf conjugate, (bottom) same experiment but with a tenfold excess of native Tf. b, flow cytometry experiment confirming that the cellular uptake of Cy5-DNA-Tf conjugate is receptor mediated. When KB cells are pretreated with excess native Tf the Cy5-DNA conjugate uptake is significantly reduced.

Figure 15:
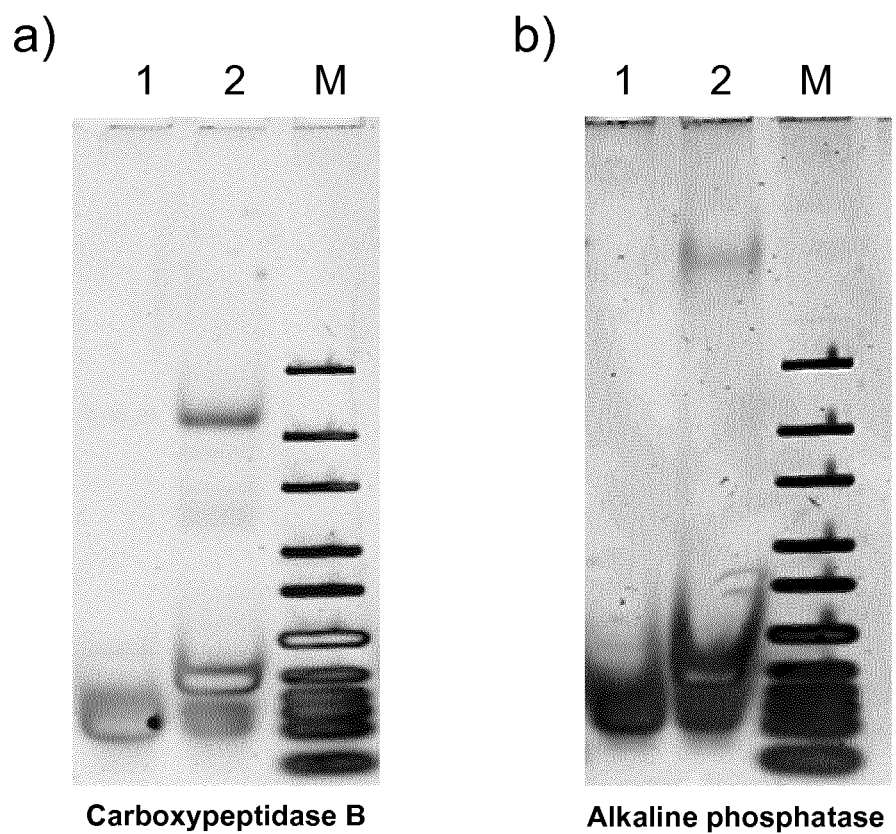

FIG. 15. Non-denaturing 4% PAGE analysis showing DNA templated labeling of metalloenzymes. a, Templated labeling of carboxypeptidase B (CPB) enzyme. b, Templated labeling of alkaline phosphatase (AP) enzyme. a-b, Lane (1) enzyme, Reacting ON and 3 eq. Cu(NO3)2, (2) enzyme, Reacting ON and Guiding ON in the presence of 3 eq. Cu(NO3)2, (M) DNA O'GeneRuler™ Ultra Low Range marker (Fermentas). The gels are stained for nucleic acids with SYBR® Gold.

CPB-DNA and AP-DNA conjugates were purified from large-scale reactions and isolated in 20% and 11% yields, respectively.

Figure 16:
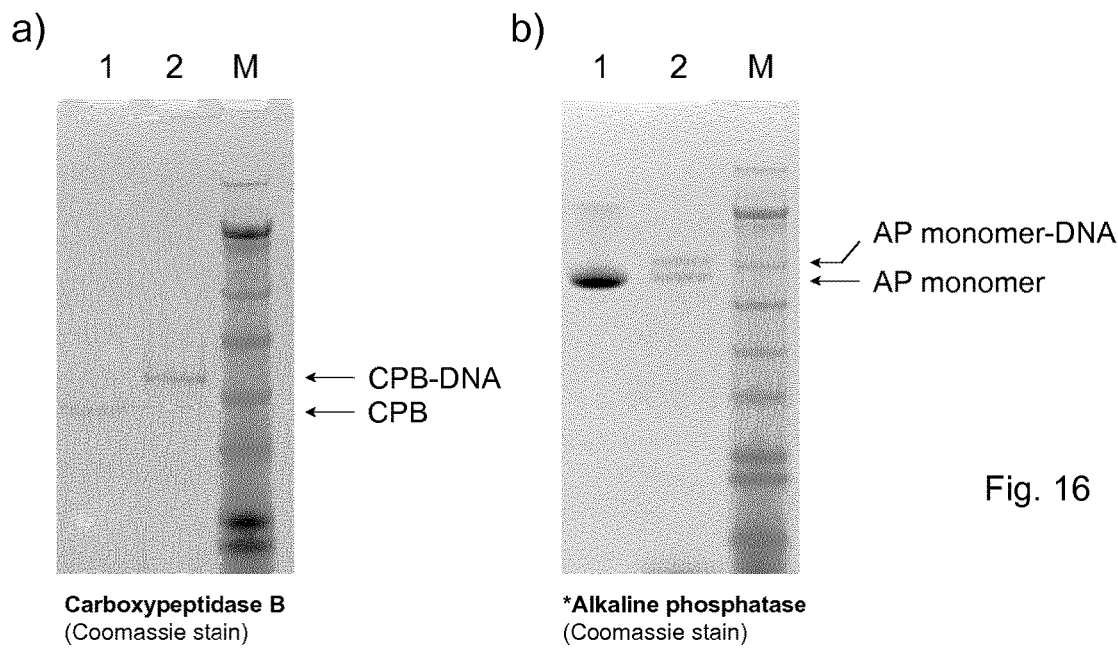

FIG. 16. SDS-PAGE analysis of DNA-enzyme conjugates produced by DTPC. a, SDS-PAGE (4-12%) analysis of purified carboxypeptidase B (CPB) conjugate. Lane (1) CPB, (2) purified CPB-DNA conjugate, (M) SeeBlue® Plus2 Prestained protein marker (Life Technologies). b, SDS-PAGE (4-12%) analysis of purified alkaline phosphatase (AP) conjugate. Lane (1) AP, (2) purified AP-DNA conjugate, (M) SeeBlue® Plus2 Prestained protein marker (Life Technologies).

N.B. Enzyme-DNA conjugates were visualized by Coomassie staining, which does not provide a quantitative readout (see FIG. 20). Because AP is a dimeric structure and has a single ON attached a 1:1 ratio between non-labeled monomer and DNA-conjugated monomer should be expected (Lane 2). Again, this was indeed observed when taking into account the ~32% reduced staining efficiency of the DNA-protein conjugate, observed from the results in FIG. 24. AP-DNA band intensity/AP band intensity=0.7.

Figure 17:
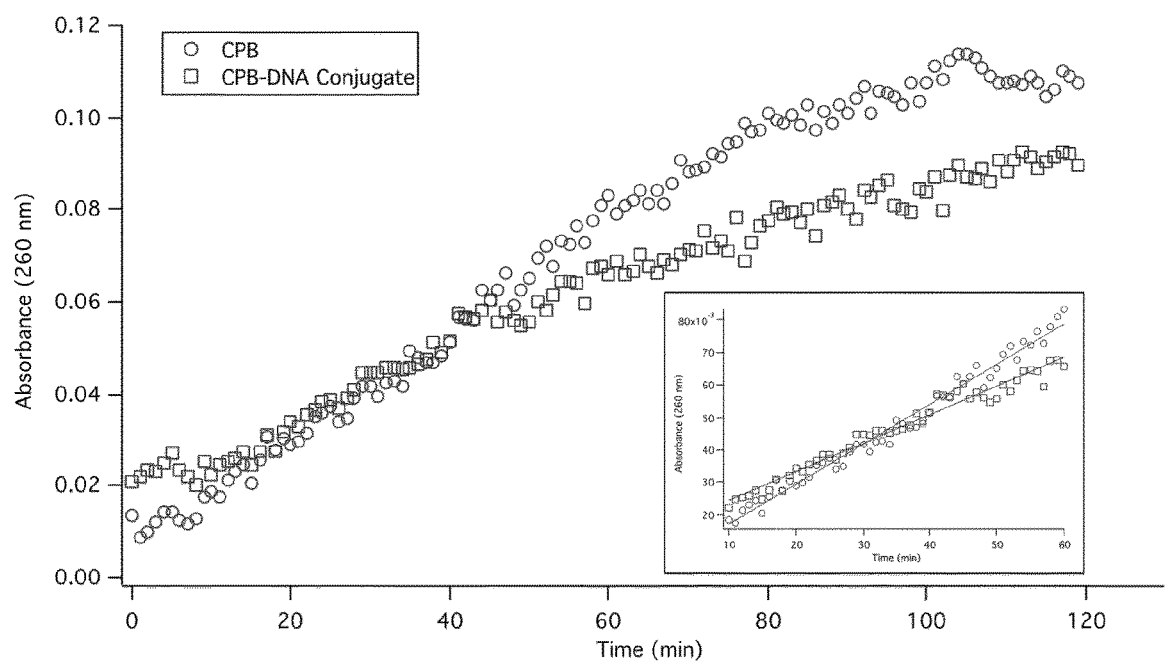

FIG. 17. Enzymatic assay of carboxypeptidase B (CPB)-DNA conjugate. Spectrophotometric assay of purified CPB conjugate after templated single-ON attachment produced by DTPC. This shows a retained biological activity of >75% of the purified conjugate (calculated by comparison of slopes from linear curve segments, see insert).

Figure 18:
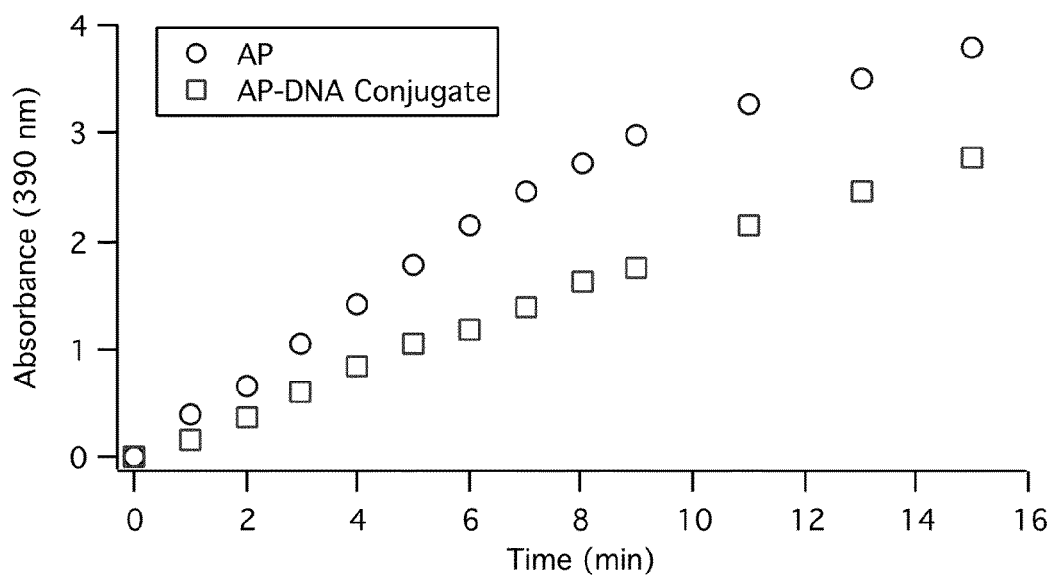

FIG. 18. Enzymatic assay of alkaline phosphatase (AP)-DNA conjugate. Colorimetric assay of purified AP conjugate after templated single-ON attachment produced by DTPC. This shows a retained biological activity of approximately 60% of the purified conjugate compared to the non-labeled enzyme (calculated by comparison of slopes from linear curve segments).

Figure 19:
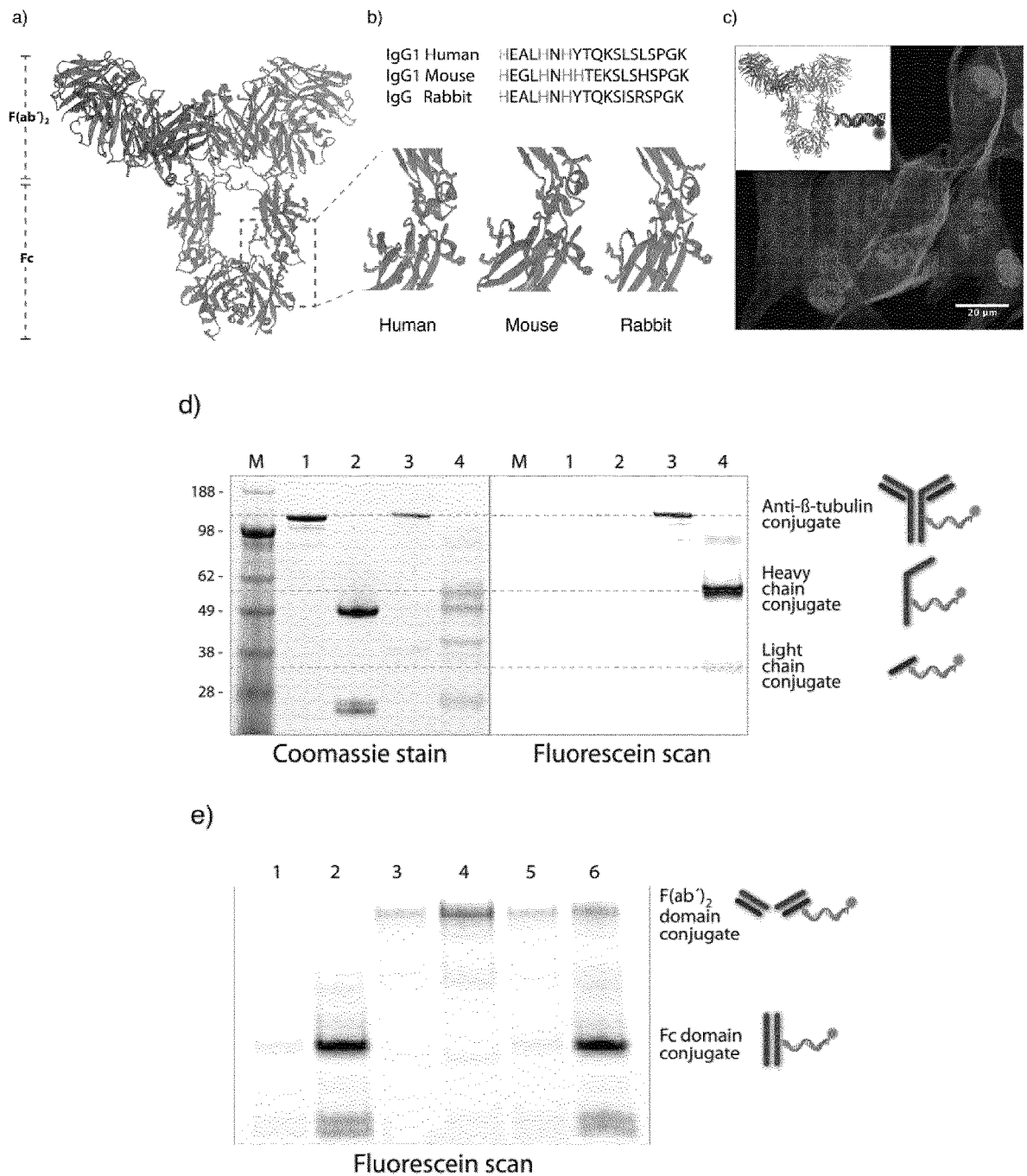

FIG. 19. Targeting the Fc domain histidine cluster of IgG1 antibodies. a, Structure of a human IgG1 (PDB entry 1HZH) containing histidines (thick lines) and lysines (thin lines). The rectangle is highlighting the histidine cluster of the constant Fc domain. b, Comparison of the histidine cluster present on IgG1 from human (PDB entry 3DNK) (SEQ ID NO:5) and mouse (PDB entry 3HKF) (SEQ ID NO:6) and IgG from rabbit (PDB entry 2VUO) (SEQ ID NO:7). BLAST alignment and crystal structures show conservation of the histidine cluster. c, 3-tubulin in fixed U-87 MG cells stained with anti-β-tubulin conjugate-Cy5 (red sphere) DNA duplex using the DTPC method. Cell nuclei were stained with DAPI. d, SDS-PAGE (4-12%) analysis of purified anti-β-tubulin conjugates containing a fluorescein-labeled ON, either non-reducing or reducing (DTT) conditions. The fluorescein label allows direct relative quantification of DNA attachment to heavy versus light chain. (left) Gel stained with Coomassie to visualize protein bands. Lane M SeeBlue® Plus2 Prestained protein marker; 1 anti-β-tubulin; 2 reduced anti-β-tubulin; 3 purified anti-β-tubulin conjugate; 4 purified and reduced anti-β-tubulin conjugate. (right) Same gel visualized by fluorescein fluorescence scan, showing that ON is preferentially conjugated to the heavy chain. e, SDS-PAGE (4-12%) analysis of templated versus non-templated DNA conjugation to the mouse Fc and F(ab')2 domains. Lane 1 Fc domain, Reacting ON and Cu(NO3)2; 2 Fc domain, Reacting ON, Guiding ON and Cu(NO3)2; 3 F(ab')2 domain, Reacting ON and Cu(NO3)2; 4 F(ab')2 domain, Reacting ON, Guiding ON and Cu(NO3)2; 5 Fc domain, F(ab')2 domain, Reacting ON and Cu(NO3)2; 6 Fc domain, F(ab')2 domain, Reacting ON, Guiding ON and Cu(NO3)2. DNA conjugation is predominantly directed towards the Fc domain.

Figure 20:
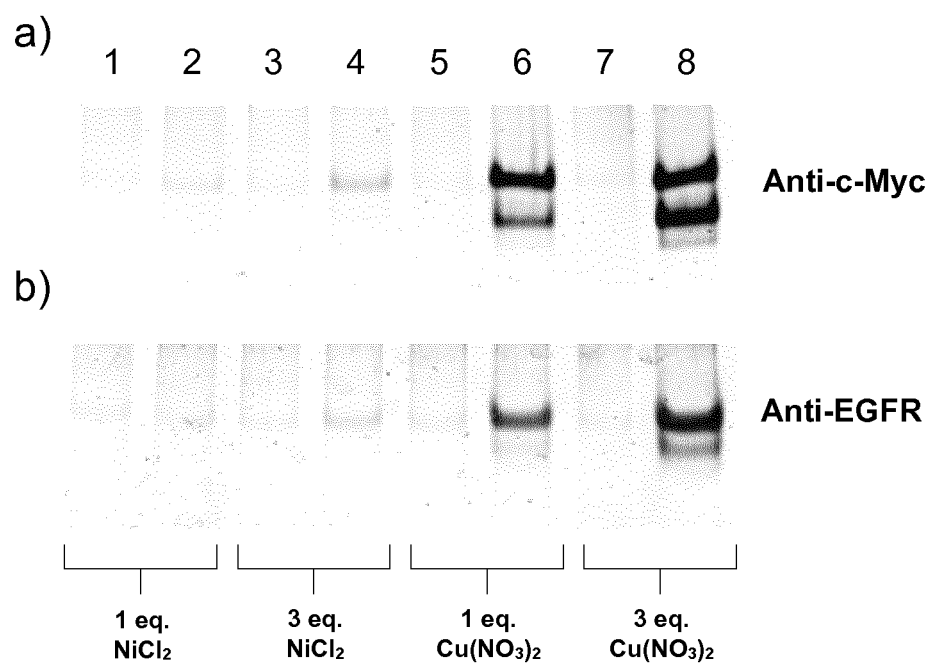

FIG. 20. Comparison of mAb-conjugate formation obtained by DTPC using different equivalents of NiCl2 and Cu(NO$_3$)$_2$. a, Non-denaturing PAGE (4%) analysis of DTPC performed on anti-c-Myc showing that more conjugation products as well as increased yields are obtained from increasing concentration of copper(II) compared to nickel (II). For all reactions 600 mM NaCl was used. b, Same experiment performed on anti-EGFR. a-b, Lane (1) mAb, Reacting ON and 1 eq. NiCl$_2$, (2) mAb, Reacting ON and Guiding ON in the presence of 1 eq. NiCl$_2$, (3) mAb, Reacting ON and 3 eq. NiCl$_2$, (4) mAb, Reacting ON and Guiding ON in the presence of 3 eq. NiCl$_2$, (5) mAb, Reacting ON and 1 eq. Cu(NO$_3$)$_2$, (6) mAb, Reacting ON and Guiding ON in the presence of 1 eq. Cu(NO$_3$)$_2$, (7) mAb, Reacting ON and 3 eq. Cu(NO$_3$)$_2$, (8) mAb, Reacting ON and Guiding ON in the presence of 3 eq. Cu(NO$_3$)$_2$. The gels are stained for nucleic acids with SYBR® Gold.

Figure 21:
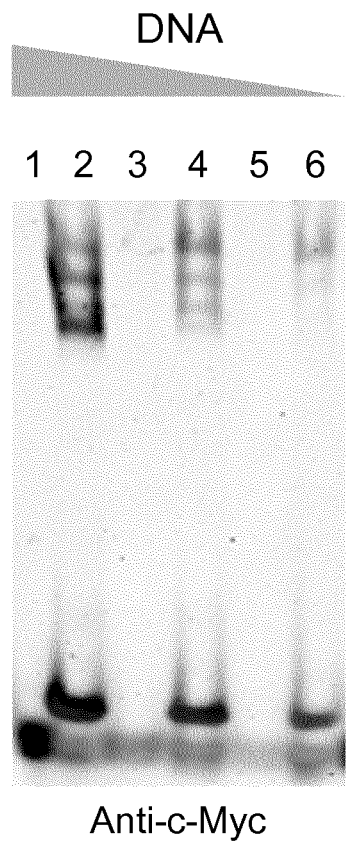

FIG. 21. Conjugation of more ONs onto monoclonal anti-c-Myc using DTPC. Non-denaturing PAGE (4%) analysis showing that more ONs are conjugated to anti-c-Myc when using increasing amounts of DNA and 3 eq. of Cu(NO$_3$)$_2$ compared to protein. For all reactions 400 mM NaCl was used. Lane (1) anti-c-Myc 1 eq., Reacting ON 1 eq., (2) anti-c-Myc 1 eq., Reacting ON 1 eq., Guiding ON 1 eq., (3) anti-c-Myc 1 eq., Reacting ON 0.5 eq., (4) anti-c-Myc 1 eq., Reacting ON 0.5 eq., Guiding ON 0.5 eq., (5) anti-c-Myc 1 eq., Reacting ON 0.25 eq., (6) anti-c-Myc 1 eq., Reacting ON 0.25 eq., Guiding ON 0.25 eq.

Figure 22:
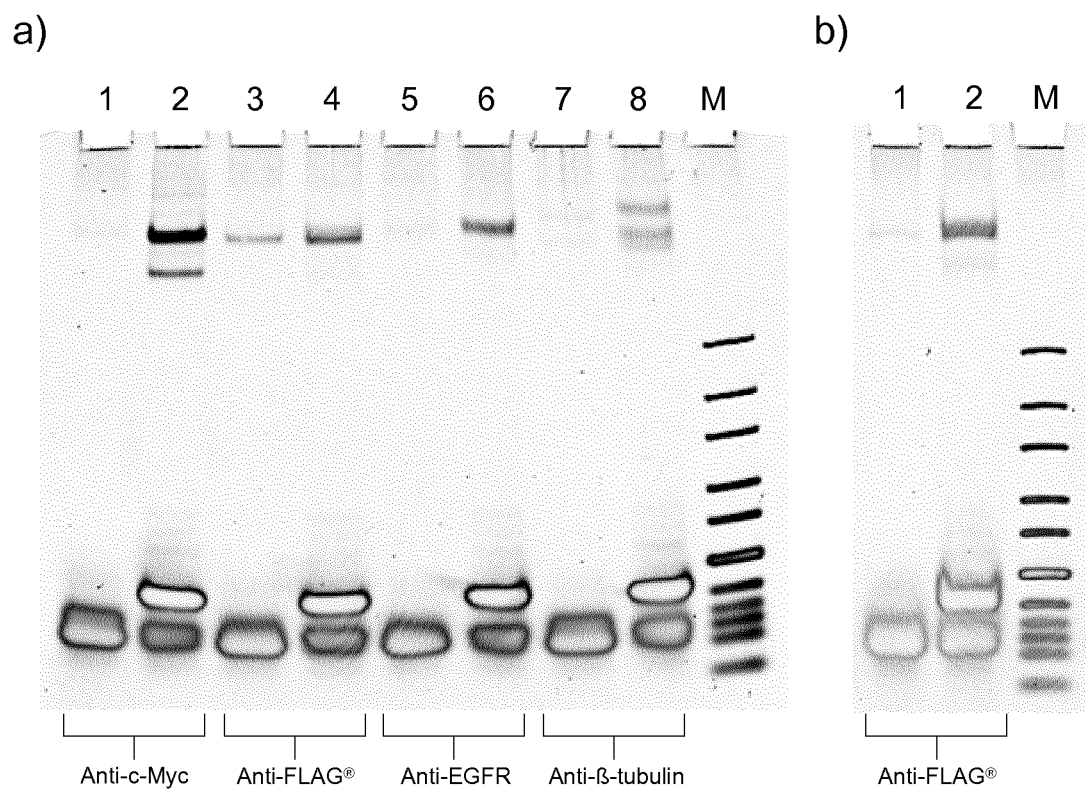

FIG. 22. Non-denaturing PAGE (4%) analysis of monoclonal DNA-antibody conjugates produced by DNA templated protein conjugation. a, Lane (1) anti-c-Myc, Reacting ON and Cu(NO$_3$)$_2$, (2) anti-c-Myc, Reacting ON and Guiding ON in the presence of Cu(NO$_3$)$_2$, (3) anti-FLAG®, Reacting ON and Cu(NO$_3$)$_2$, (4) anti-FLAG®, Reacting ON and Guiding ON in the presence of Cu(NO$_3$)$_2$, (5) anti-EGFR, Reacting ON and Cu(NO$_3$)$_2$, (6) anti-EGFR, Reacting ON and Guiding ON in the presence of Cu(NO$_3$)$_2$, (7) anti-β-tubulin, Reacting ON and Cu(NO$_3$)$_2$, (8) anti-I-tubulin, Reacting ON and Guiding ON in the presence of Cu(NO$_3$)$_2$, (M) DNA O'GeneRuler™ Ultra Low Range marker (Fermentas). Faster migrating product band (lane 2 and 8) originates from two ONs attached to the same mAb as validated from ESI mass spectrometry of purified anti-c-Myc conjugates (see FIG. 23). b, Optimization of DTPC on anti-FLAG® to diminish non-templated reaction by reducing the protein concentration approx. 30% (to make 1:1 DNA:protein). (1) anti-FLAG®, Reacting ON and Cu(NO$_3$)$_2$, (2) anti-FLAG®, Reacting ON and Guiding ON in the presence of Cu(NO$_3$)$_2$, (M) DNA O'GeneRuler™ Ultra Low Range marker (Fermentas).

Figure 23:
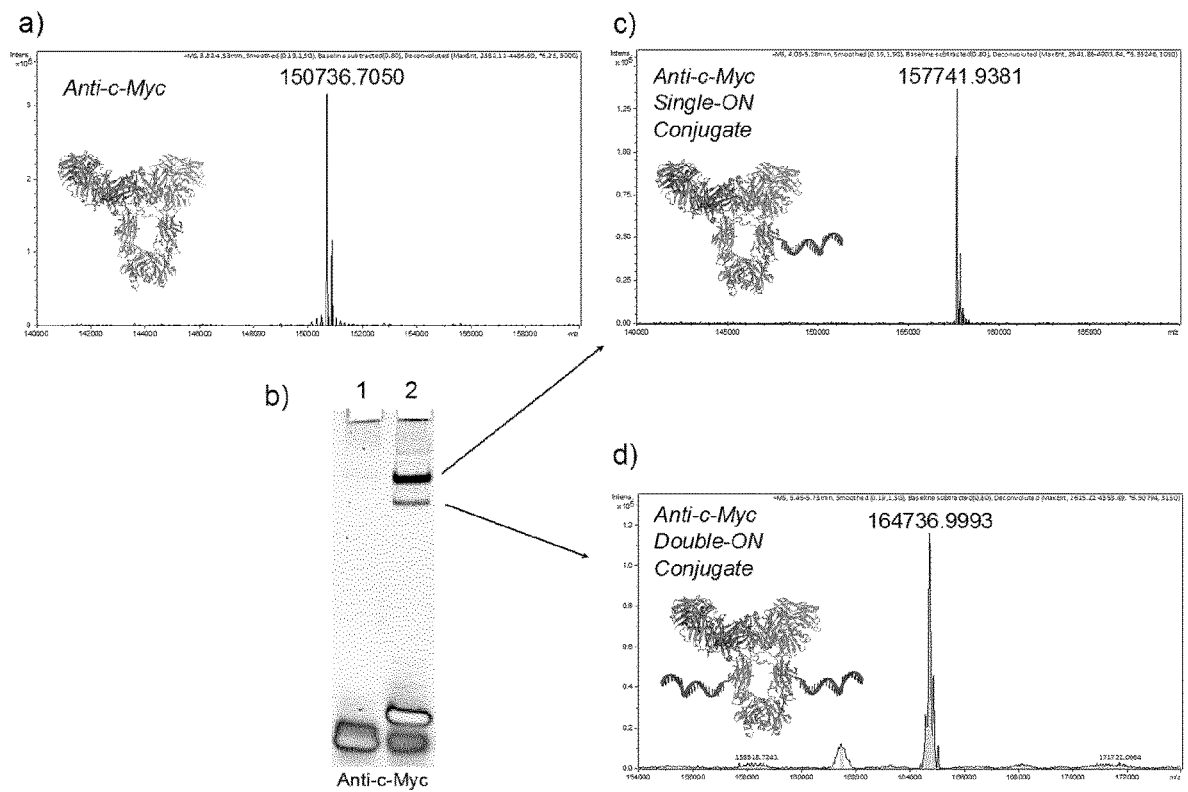

FIG. 23. Mass Spectrometry data on purified anti-c-Myc conjugates produced by DTPC. a, Electrospray ionization mass spectrometry data (deconvoluted) for anti-c-Myc. b, Site-selective conjugation of ON to anti-c-Myc (cut-out from Supplementary FIG. 18). Lane (1) anti-c-Myc, Reacting ON and Cu(NO3)2, (2) anti-c-Myc, Reacting ON and Guiding ON in the presence of Cu(NO3)2. c, Mass spectrometry (ESI) analysis of the slow migrating major product band revealing single-ON labeling. d, ESI analysis of the faster migrating minor product band showing that two ONs are attached to the same antibody. The added molecular weight of a single DNA strand is 7000 Da (calc.).

Δmass Anti-c-Myc Single-ON (found)=157742 Da−150737 Da=7005 Da

Δmass Anti-c-Myc Double-ON (found)=164737 Da−150737 Da=14000 Da

Figure 24:
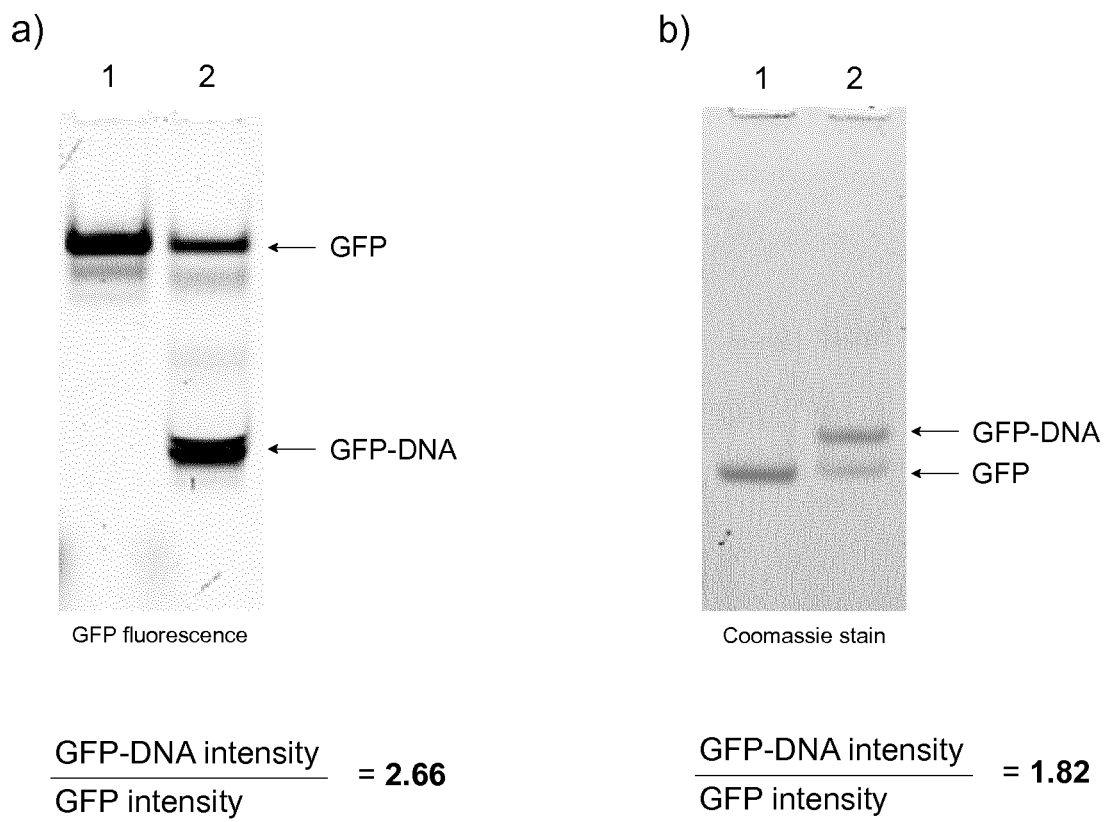

FIG. 24. Correlation of reduced Coomassie staining sensitivity between non-conjugated and DNA-conjugated proteins. a, Non-denaturing PAGE (6%) analysis of crude (incomplete conversion) reaction mixture after applying DTPC to his6-tagged GFP. The gel shows a ratio of band intensities between GFP-DNA and non-conjugated GFP of 2.66 based on GFP fluorescence. b, Same crude reaction mixture analyzed by SDS-PAGE (4-12%) showing a ~32% reduction in conjugation product band intensity based on Coomassie staining ((2.66-1.82)/2.66.100=32%).

Figure 25:
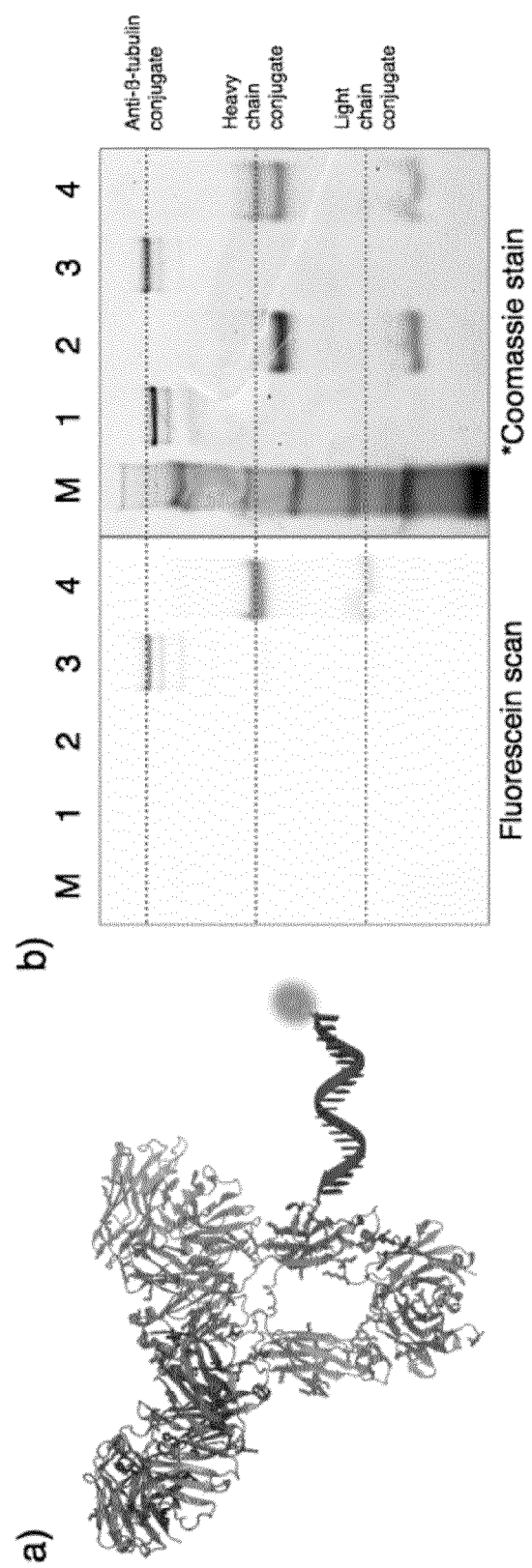

FIG. 25. SDS-PAGE analysis of reduced anti-c-Myc conjugate labeled with DNA-fluorescein. a, Illustration showing the DNA-Flc-conjugate used for the reduction experiments. b, SDS-PAGE (4-12%) analysis of the reduced (in 10 mM DTT) conjugates to evaluate the templated ON attachment sites obtained by DTPC. The experiment shows that the templated conjugation is significantly favored towards the heavy chain. Lane (M) SeeBlue® Plus2 Prestained protein marker (Life Technologies), (1) anti-c-Myc, (2) reduced anti-c-Myc, (3) purified anti-c-Myc DNA-conjugate, (4) purified and reduced anti-c-Myc DNA-conjugate.

Proteins were visualized by Coomassie staining, which does not provide a quantitative readout, since the DNA conjugate does not stain as efficiently as proteins alone (see FIG. 24). Since the antibody is a dimeric structure and has a single ON attached (preferentially at the heavy chain) there should be approximately a 1:1 ratio between non-labeled heavy chain and the heavy chain conjugate (Lane 4, Coomassie stained gel). This was indeed observed when accounting for the ~32% reduced staining efficiency of the DNA-protein conjugate, achieved from the results in FIG. 24. Heavy chain conjugate band intensity/non-labeled heavy chain band intensity=0.7.

Figure 26:
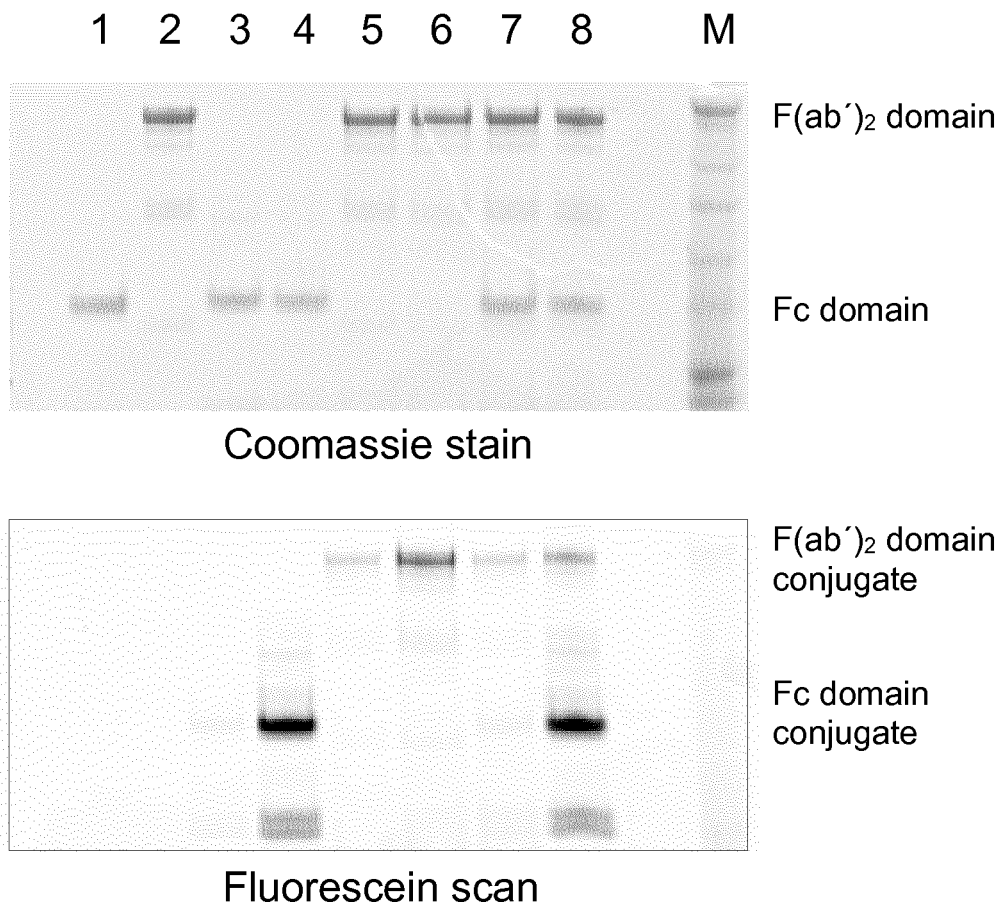

FIG. 26. Coomassie stain of FIG. 19e showing that equimolar amounts of Fc and F(ab')2 was used. SDS-PAGE (4-12%) analysis of DTPC performed on Fc and F(ab')2 domains. This shows that ON is predominantly directed to the Fc domain. (top) The F(ab')2 domain is approx. two times larger than the Fc domain and does therefore stain twice as intensive with Coomassie showing that equimolar proteins have been used, (bottom) fluorescein scan showing that the ON is directed to the constant Fc domain (similar to FIG. 19e). Lane (1) Fc domain, (2) F(ab')2 domain, (3) Fc domain, Reacting ON and Cu(NO$_3$)$_2$, (4) Fc domain, Reacting ON, Guiding ON and Cu(NO$_3$)$_2$, (5) F(ab')2 domain, Reacting ON and Cu(NO$_3$)$_2$, (6) F(ab')2 domain, Reacting ON, Guiding ON and Cu(NO$_3$)$_2$, (7) Fc domain, F(ab')2 domain, Reacting ON and Cu(NO$_3$)$_2$, (8) Fc domain, F(ab')2 domain, Reacting ON, Guiding ON and Cu(NO$_3$)$_2$, (M) SeeBlue® Plus2 Prestained protein marker (Life Technologies).

Figure 27:
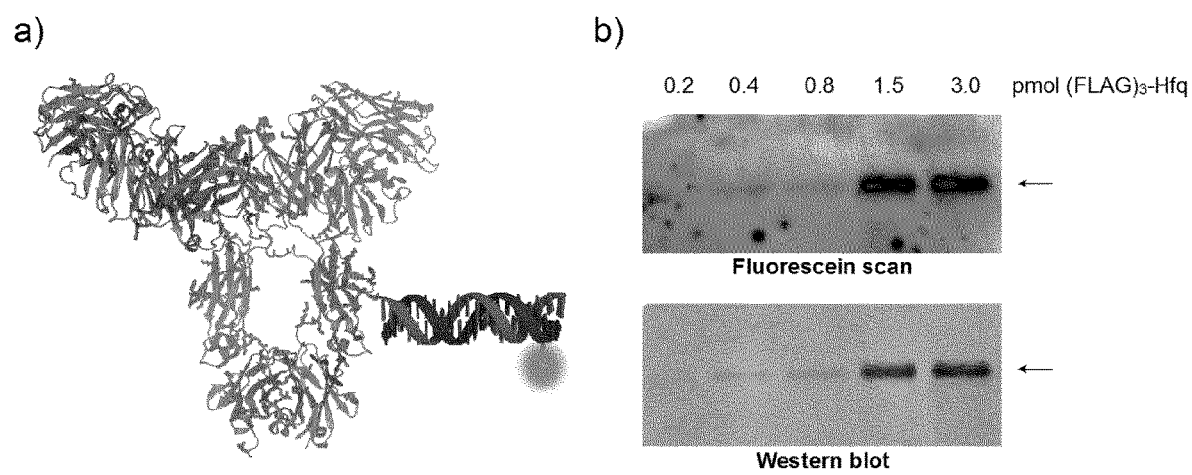

FIG. 27. Western blotting using anti-FLAG® conjugate produced by DTPC. a, Illustration showing the DNA-Flc-conjugate (anti-FLAG®) used for the Western blotting experiments. b, (top) fluorescein scan of DNA-antibody conjugate against varies concentrations of (FLAG)3-tagged Hfq protein, (bottom) Subsequent Western blotting of the anti-FLAG® conjugate using a secondary mouse-antibody containing horseradish peroxidase reporter enzyme.

Figure 28:
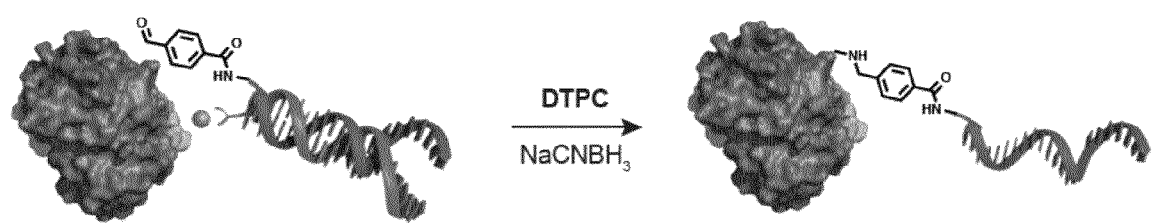

FIG. 28. DNA-templated protein conjugation using reductive amination as described in Example 7.

Figure 29:
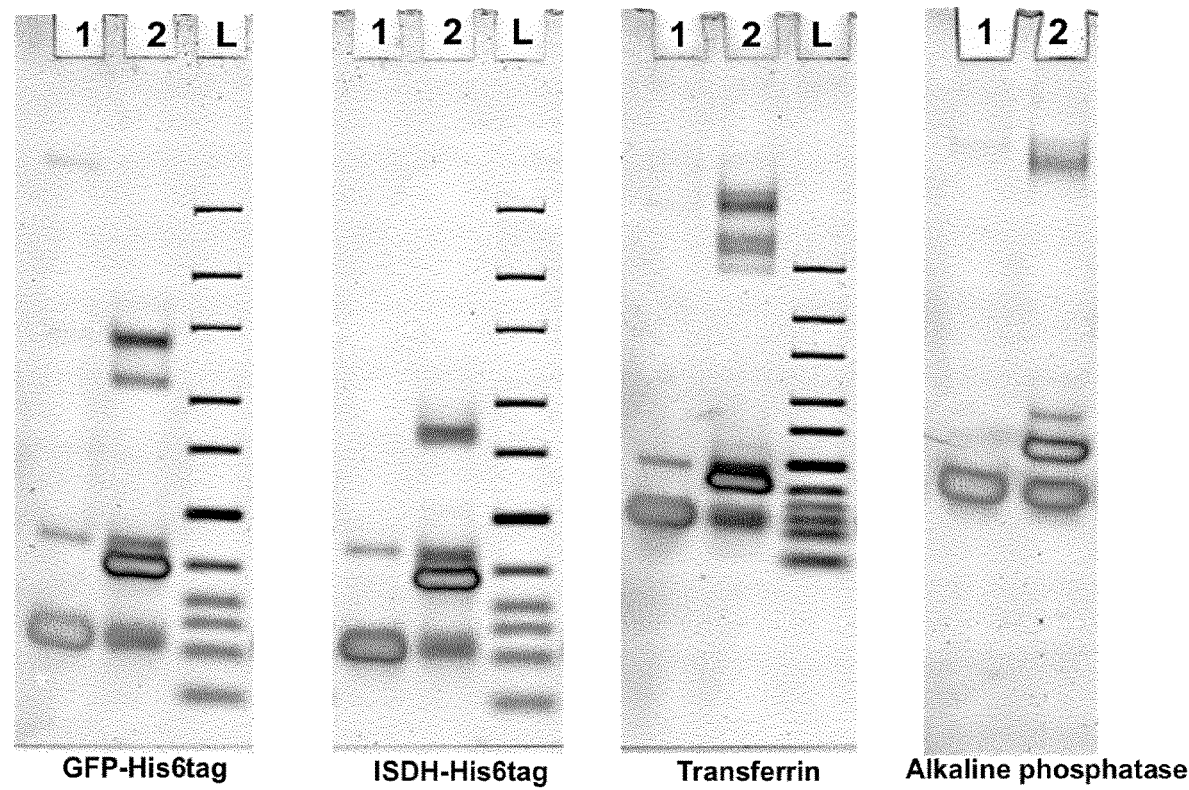

FIG. 29. PAGE (5%, native) analysis of reductive amination protein conjugation reactions to GFP, ISDH, Transferrin and alkaline phosphatase. Each gel shows selective coupling in the presence of the Guiding ON. In each gel: Lane 1: Reacting aldehyde ON, Cu(NO$_3$)$_2$ and POI (protein of interest). Lane 2: Reacting aldehyde ON, Guiding ON, Cu(NO$_3$)$_2$ and POI.

Ladder: O'gene ruler.

Figure 30:
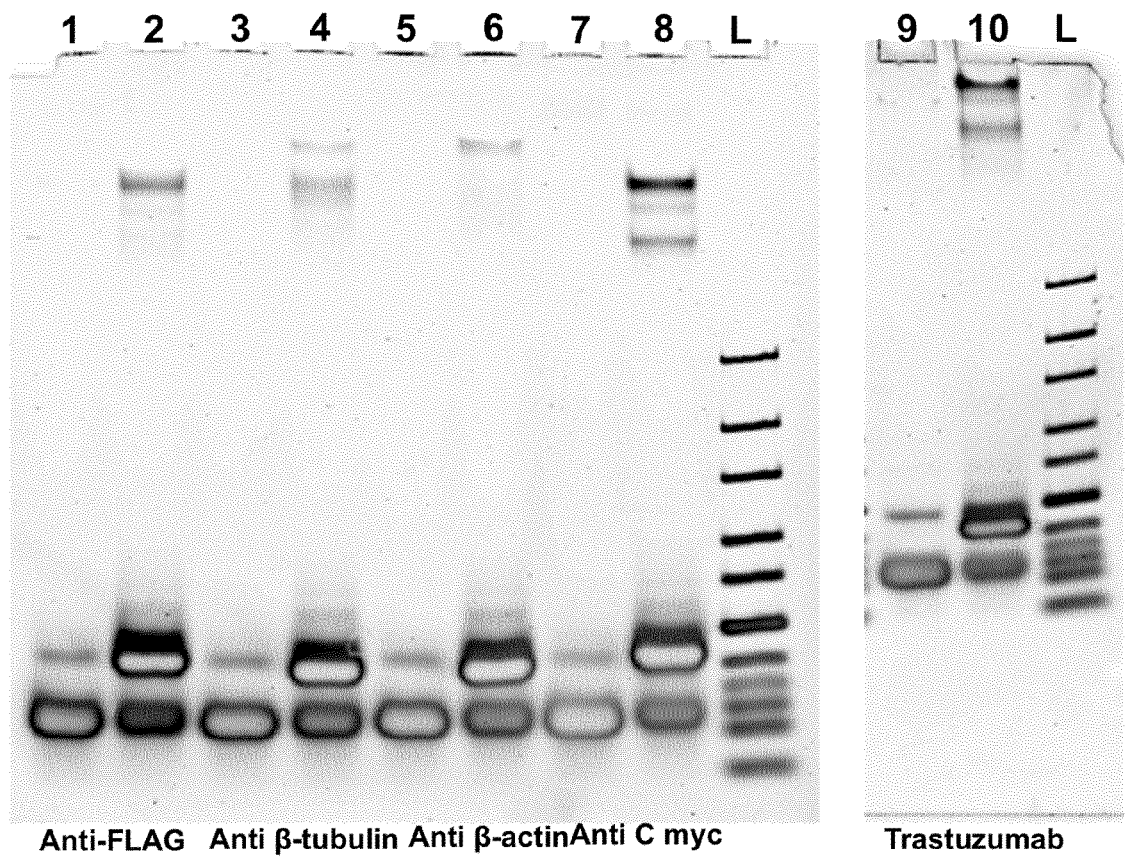

FIG. 30. PAGE (4% native) analysis of protein conjugation reactions to Anti-FLAG, Anti beta-tubulin, Anti beta-actin, Anti C myc and Trastuzumab. Lane 1, 3, 5, 7, 9: Reacting aldehyde ON, Cu(NO$_3$)$_2$ and POI. Lane 2, 4, 6, 8, 10: Reacting aldehyde ON, Guiding ON, Cu(NO$_3$)$_2$ and POI. Ladder: O'gene ruler.

Figure 31:
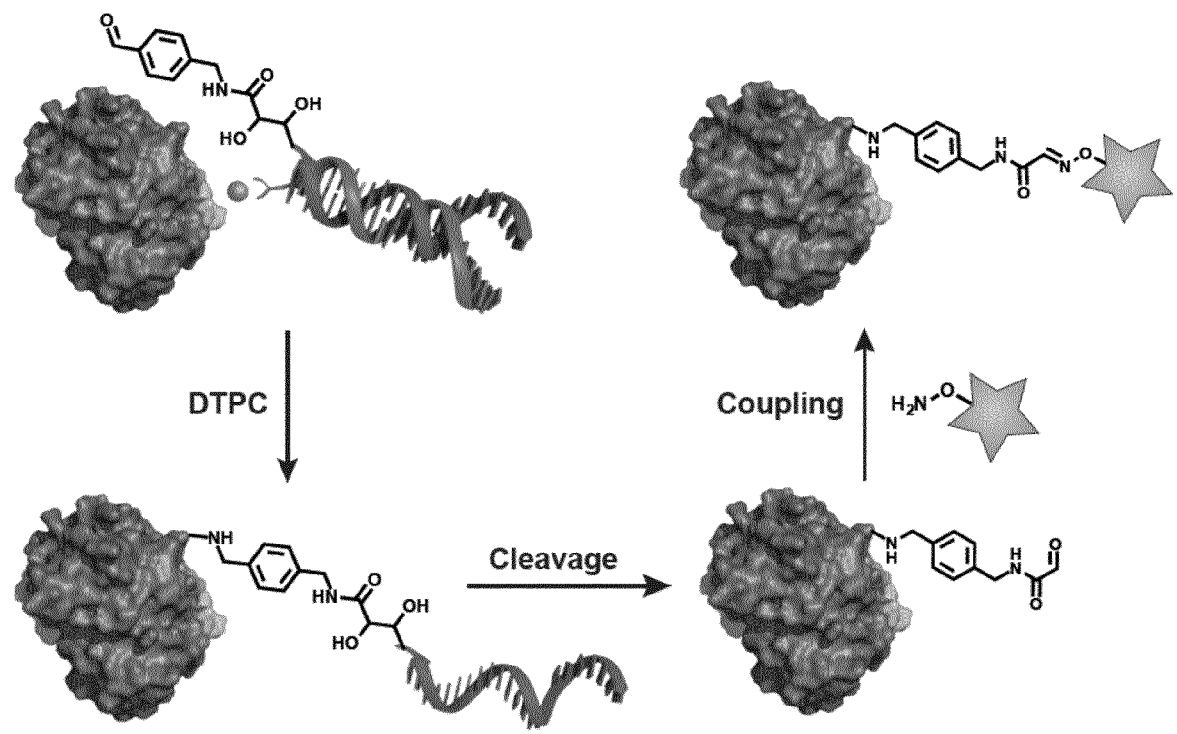

FIG. 31. DNA-templated protein conjugation using reductive amination, cleavage and coupling of amino-oxy functionalized molecules.

Figure 32:
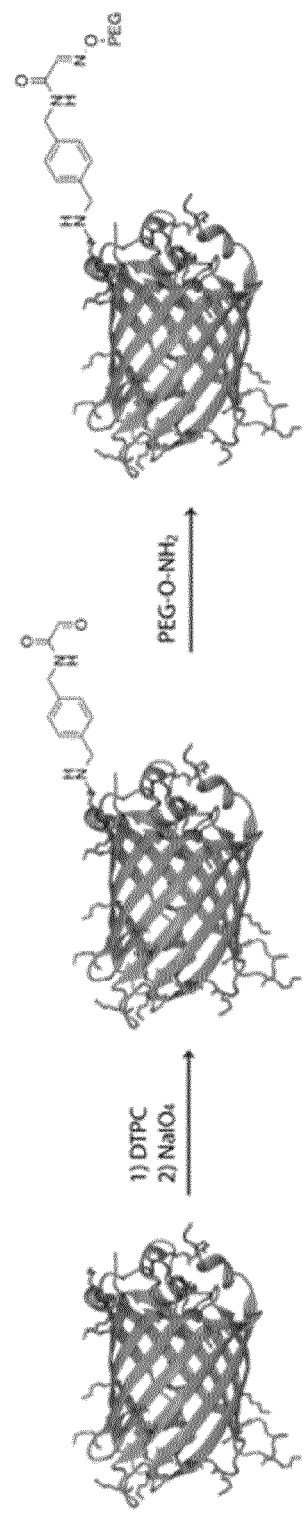

FIG. 32. Reaction scheme showing 1) DNA-templated protein conjugation with reductive amination on his-tagged GFP followed by 2) removal of DNA by NaIO$_4$ cleavage of diol linker and lastly coupling with aminooxy-PEG.

Figure 33:
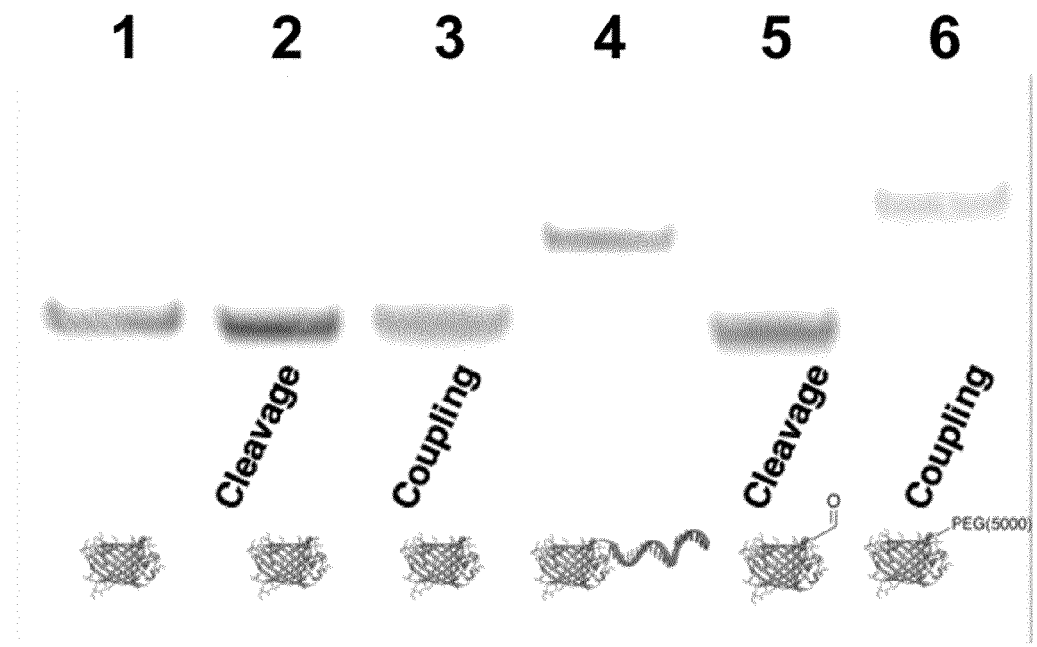

FIG. 33. SDS PAGE analysis of reaction scheme, showing no reaction for uncoupled GFP, however DNA cleavage from GFP-DNA conjugate and further coupling of the aldehyde with PEG-ONH$_2$. Lane 1: GFP Lane 2: GFP, NaIO$_4$ and NaOAc (pH 5.5, 100 mM, 0.02% Tween 20) Lane 3: As lane 2 but with PEG(5000)-ONH2 and Phosphate buffer (pH 6.5, 50 mM, 0.02% Tween 20) Lane 4: GFP-DNA conjugate Lane 5: GFP-DNA conjugate, NaIO$_4$ and NaOAc (pH 5.5, 100 mM, 0.02% Tween 20) Lane 6: As lane 5 but with PEG(5000)-ONH2 and Phosphate buffer (pH 6.5, 50 mM, 0.02% Tween 20).

Figure 34:
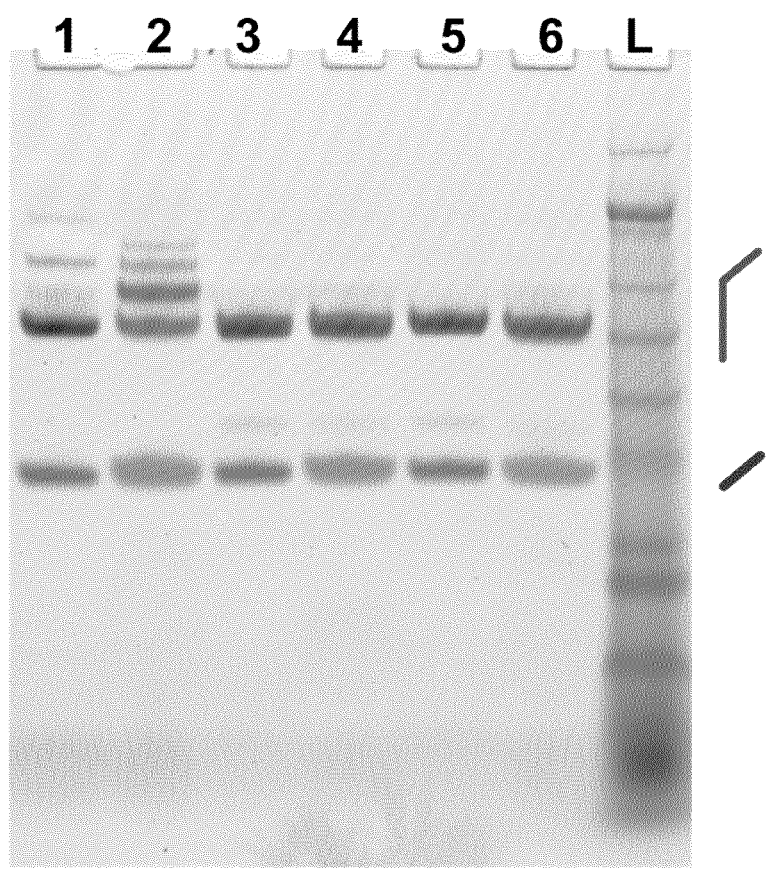

FIG. 34. SDS PAGE of PEG-ONH$_2$ coupling to glycosylated (lane 1 and 2) or deglycosylated Trastuzumab (lane 3-6). Lane 1, 3, 5: Trastuzumab. Lane 2, 4, 6: Trastuzumab, NaIO$_4$ treatment followed by coupling to PEG-ONH$_2$.

Figure 35:
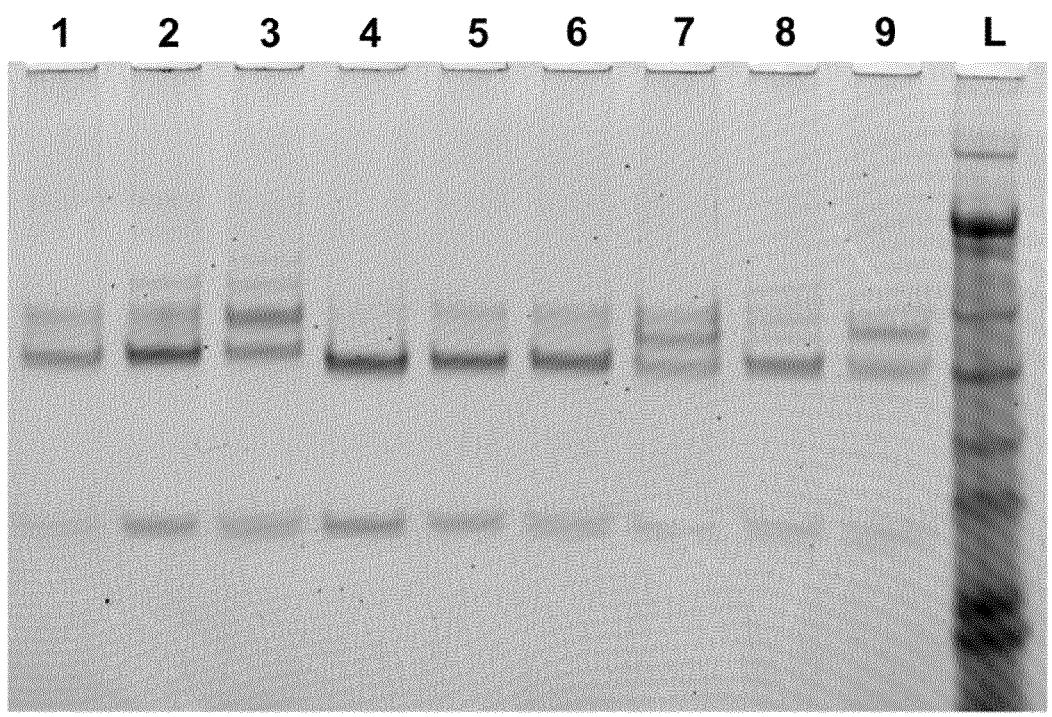

FIG. 35. SDS PAGE analysis of reaction scheme, showing selective introduction of single aldehyde in deglycosylated Anti-C-myc and coupling with PEG-ONH$_2$. All antibodies were reduced with DTT (50 mM) before SDS PAGE. Lane 1: Anti C-myc, lane 2: Anti C-myc, NaIO$_4$, lane 3: Anti C-myc, NaIO$_4$, PEG-ONH$_2$, lane 4: Deglycosylated Anti C-myc, lane 5: Deglycosylated Anti C-myc, NaIO$_4$, lane 6: Deglycosylated Anti C-myc, NaIO$_4$, PEG-ONH$_2$ lane 7: Deglycosylated Anti C-myc-DNA conjugate, lane 8: Deglycosylated Anti C-myc-DNA conjugate, NaIO$_4$, lane 9: Deglycosylated Anti C-myc-DNA conjugate, NaIO$_4$, PEG-ONH$_2$, lane L: SeeBlue Plus2 Prestained ladder.

Figure 36:
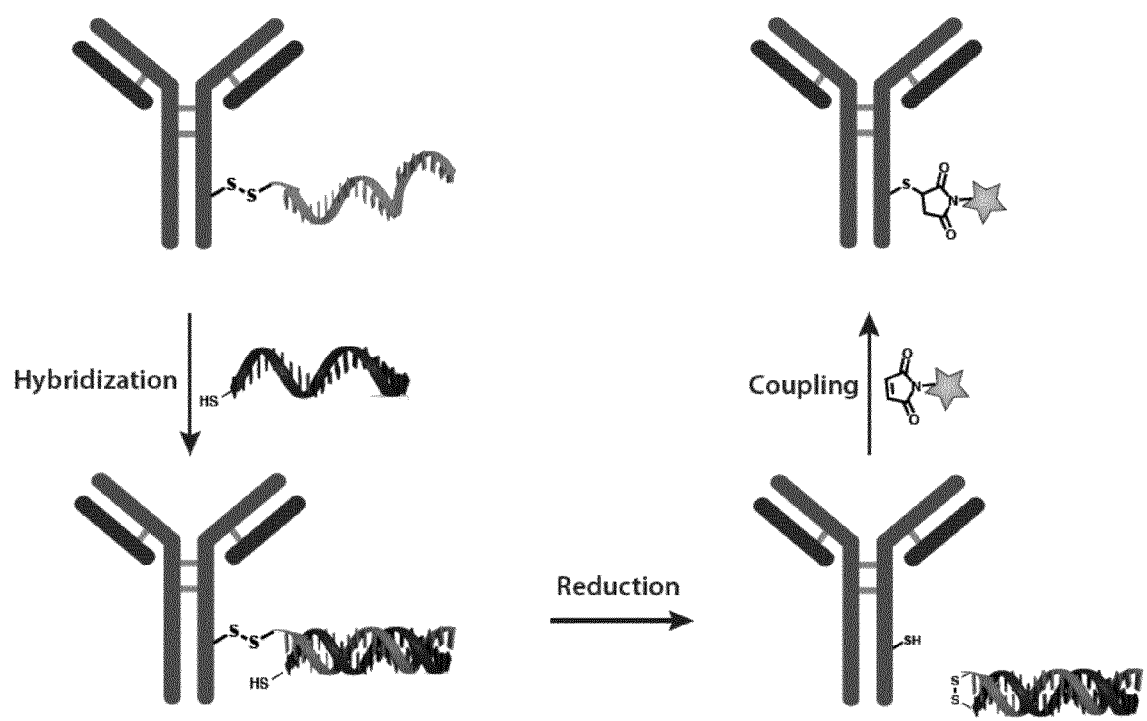

FIG. 36. DNA-templated selective disulphide cleavage. By the addition of a thiol containing DNA strand fully complementary to the Reacting ON disulphide exchange occurs ultimately facilitating cleavage of DNA from the protein. Only the oligonucleotide disulphide bridge will be cleaved by this method. The resulting free thiol can furthermore be used for further conjugations with thiol reacting groups like maleimides.

Figure 37:
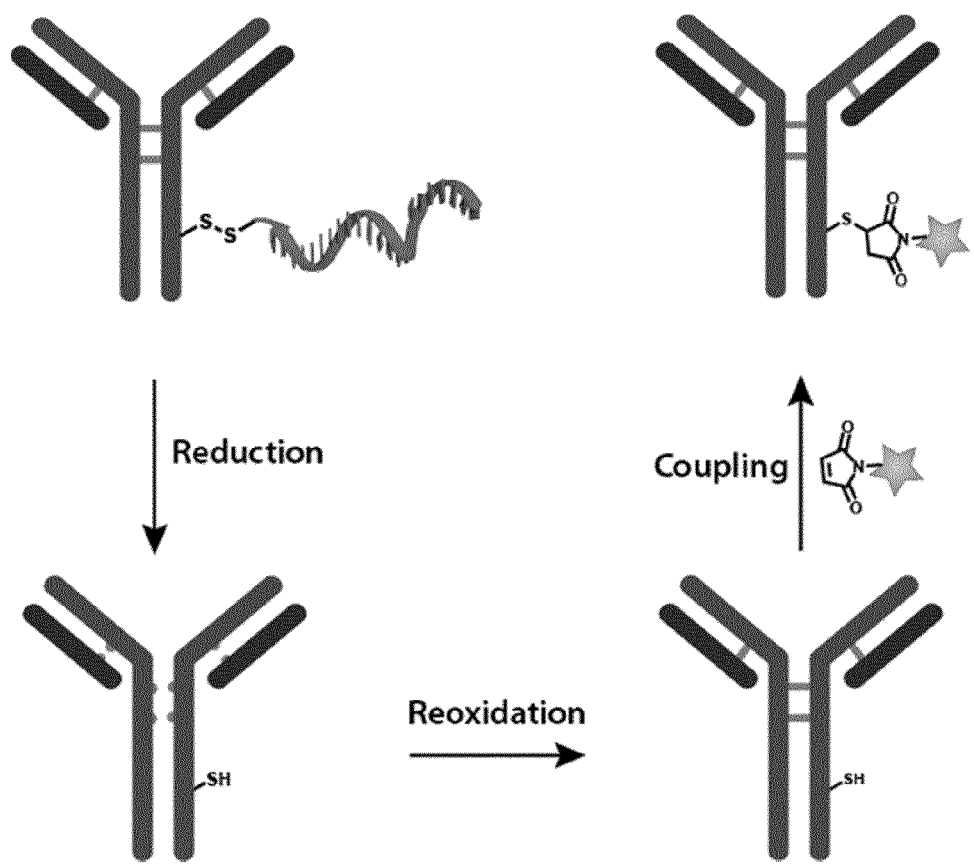

FIG. 37. Installation of single thiol on antibodies using a reduction, reoxidation strategy. By mild reduction of the DNA-antibody conjugate containing a disulphide linker, the linker and interchain disulphides are reduced without braking the overall morphology of the antibody. The interchain thiols can be reoxidized to reform the interchain bridges leaving a newly installed free thiol, which can be used for further conjugation with e.g. maleimides.

Figure 38:
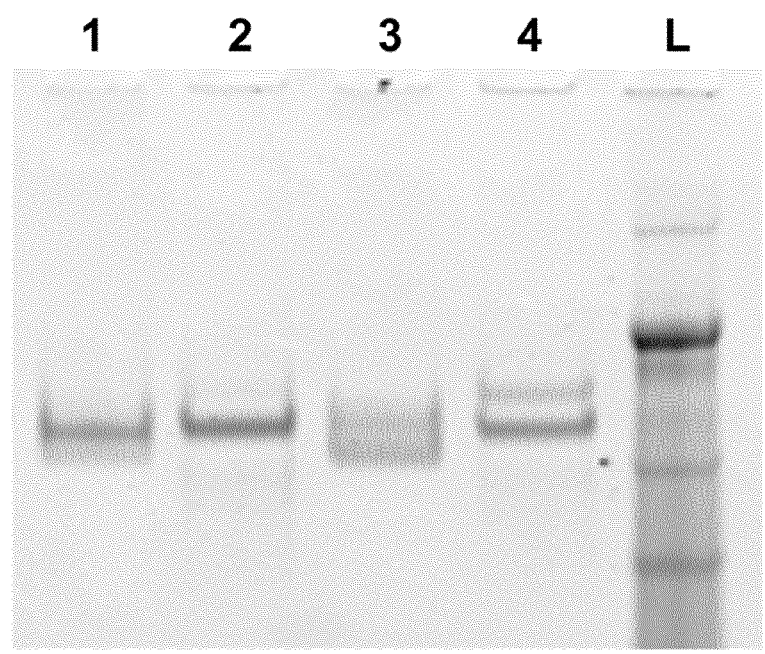

FIG. 38. SDS PAGE analysis of DNA-templated disulphide cleavage and coupling. Lane 1: Trasferrin-LDSP-DNA conjugate, lane 2: Trasferrin-LDSP-DNA conjugate and PEG-maleimide, lane 3: Trasferrin-LDSP-DNA conjugate, compl. DNA thiol, lane 4: Transferrin-LDSP-DNA conjugate, compl. DNA thiol and PEG-maleimide, lane L: SeeBlue plus2 prestained.

Figure 39:
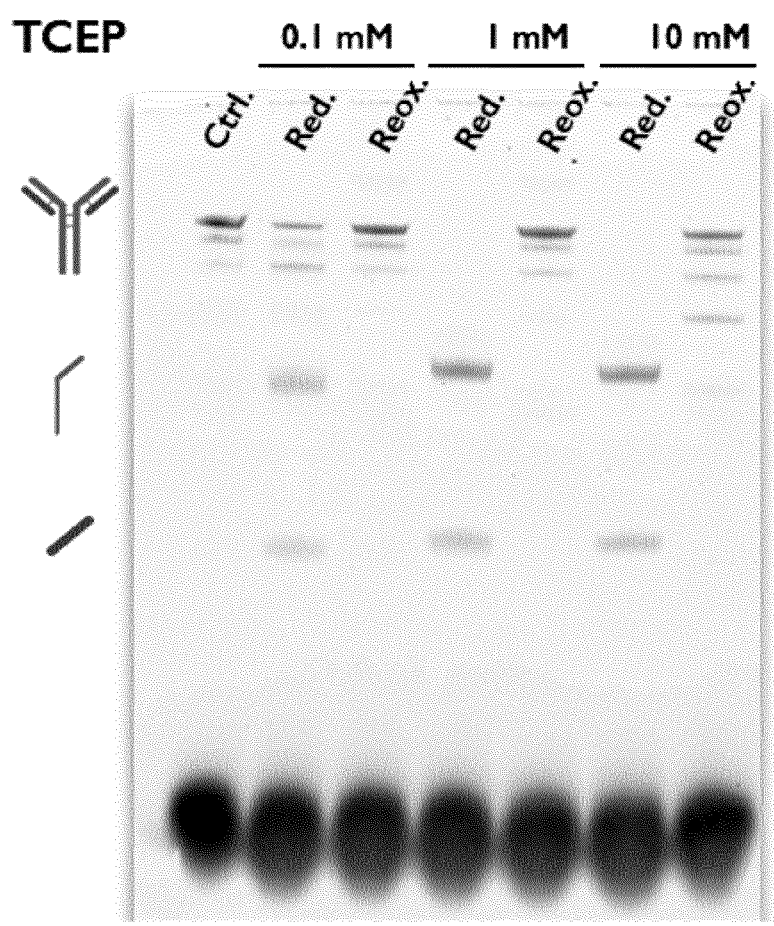

FIG. 39. SDS PAGE gel showing Anti C-myc reduction to heavy and light chain and reoxidation back to the full antibody. Anti C-myc is reduced using different amounts of TCEP and reoxidized with Cu(II).

Figure 40:
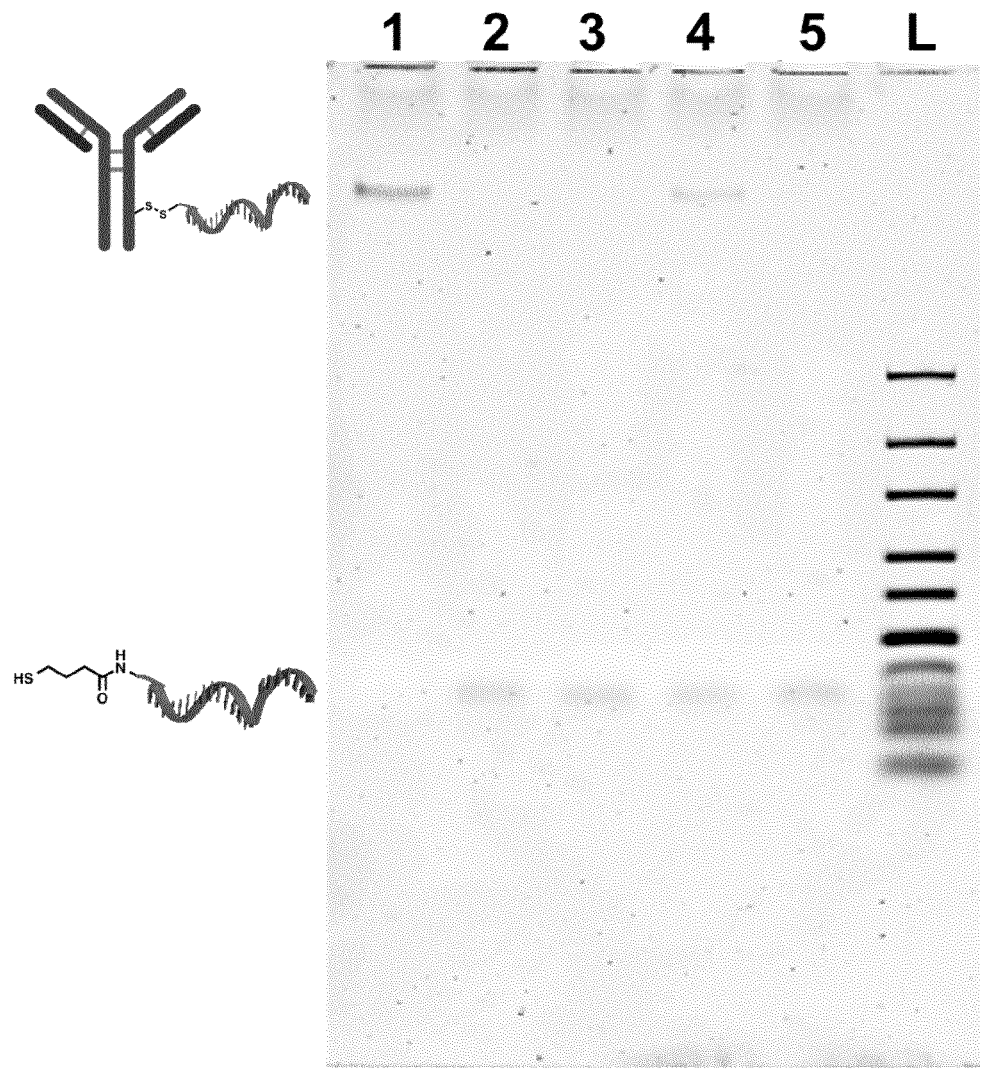

FIG. 40. Native PAGE (4%) analysis of TCEP cleavage of Anti C-myc-DNA conjugate with LDSP cleavable linker. Lane 1: Anti-C-myc DNA conjugate, lane 2: Anti-C-myc DNA conjugate, TCEP (1 mM), lane 3: Anti-C-myc DNA conjugate, TCEP (3 mM), lane 4: Anti-C-myc DNA conjugate, TCEP (5 mM), lane 5: Anti-C-myc DNA conjugate, TCEP (7 mM), lane L: Ladder, O'gene ruler.

Figure 41:
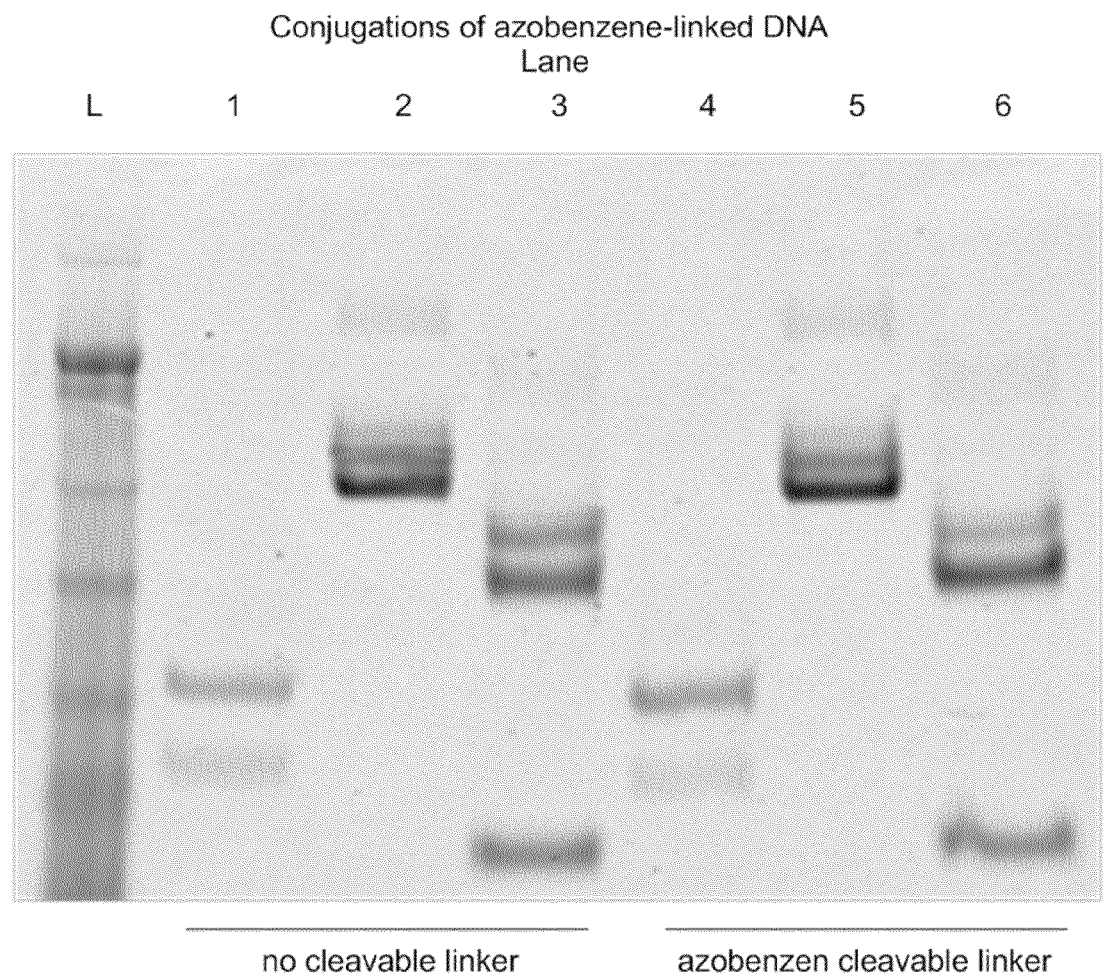

FIG. 41: SDS-PAGE analysis of a comparison of protein conjugation reactions between aldehyde modified DNA with or without the azobenzene cleavable linker. The conjugation reactions were performed using reductive amination on the proteins his$_6$-tagged GFP, Tf and Cmyc. L: SeeBlue® Plus2 Pre-stained Protein Standard. Lane 1: GFP, aldehyde-modified DNA, Cu(NO$_3$)$_2$, tris-NTA modified DNA. Lane 2: Tf, aldehyde-modified DNA, Cu(NO$_3$)$_2$, tris-NTA modified DNA. Lane 3: Cmyc, aldehyde-modified DNA, Cu(NO$_3$)$_2$, tris-NTA modified DNA. Lane 4: GFP, aldehyde-azobenzene-modified DNA, Cu(NO$_3$)$_2$, tris-NTA modified DNA. Lane 5: Tf, aldehyde-azobenzene-modified DNA, Cu(NO$_3$)$_2$, tris-NTA modified DNA. Lane 6: Cmyc, aldehyde-azobenzene-modified DNA, Cu(NO$_3$)$_2$, tris-NTA modified DNA.

Figure 42:
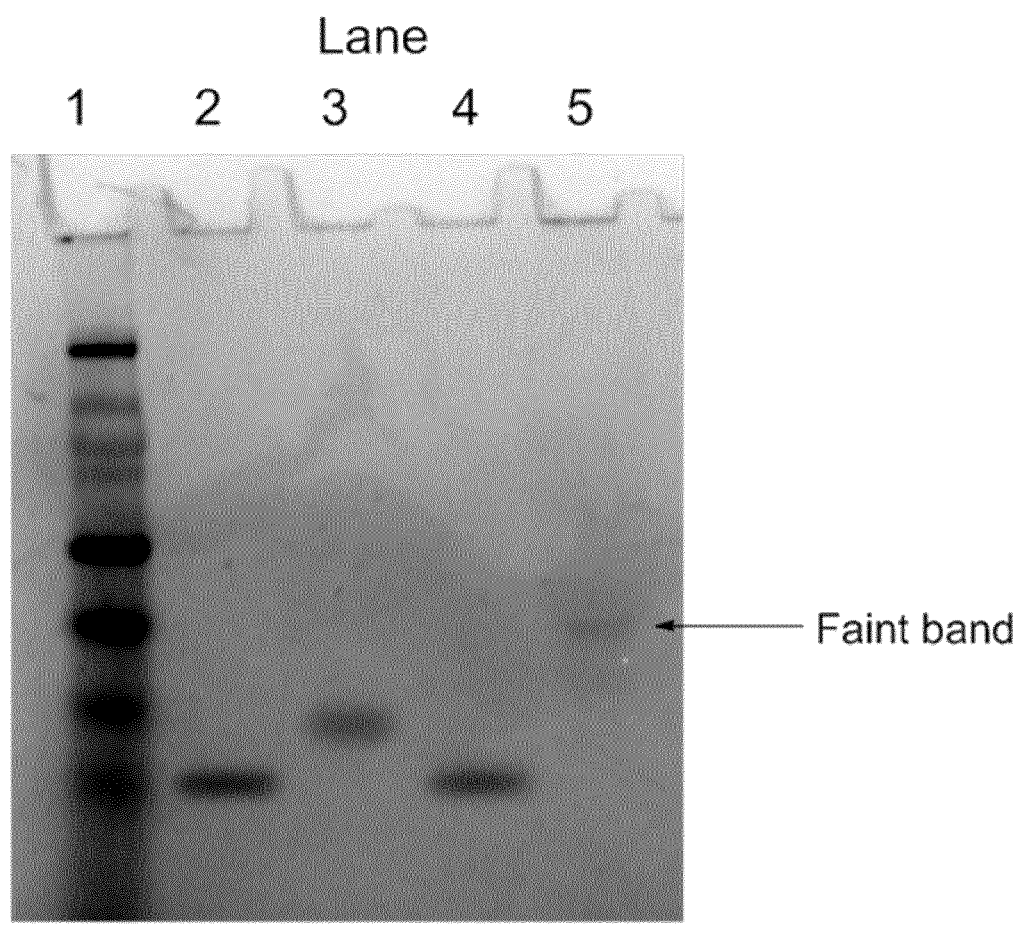

FIG. 42: SDS-PAGE analysis of reactions using the azobenzene cleavable linker. The coupling of the DNA to the GFP was performed followed by cleavage of the linker using Na$_2$S$_2$O$_4$ forming an aniline modified GFP. PEG10,000 was coupled to the aniline modified GFP. Lane 1: Molecular weight ladder Lane 2: GFP Lane 3: purified GFP-Azobenzene linked DNA conjugated Lane 4: GFP-Azobenzene linked DNA, Na$_2$S$_2$O$_4$, Phosphate buffer (pH=6.5) 5: As lane 4 but with o-aminophenol-PEG10,000 and K$_3$Fe(CN)$_6$.

Figure 43:
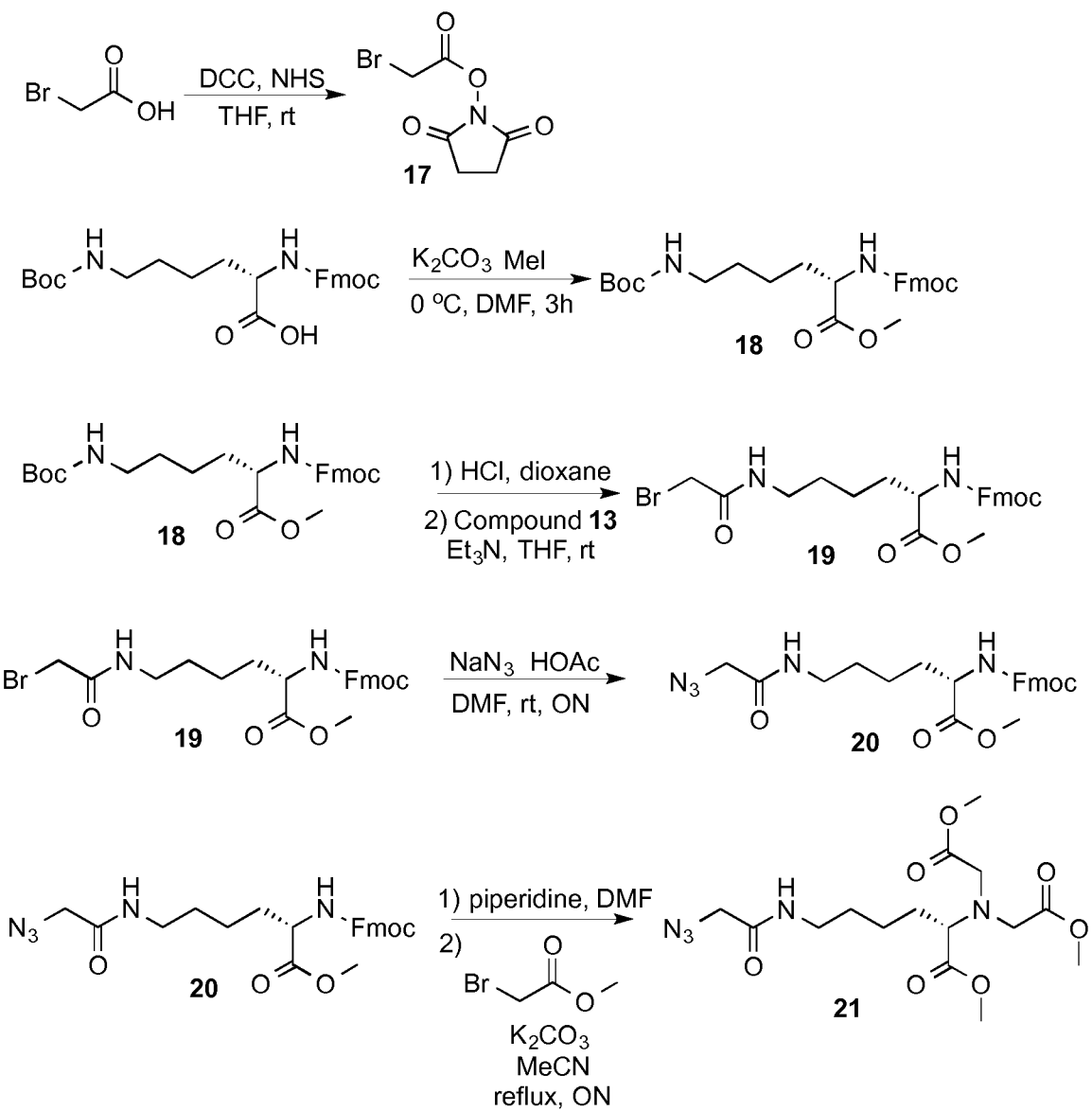

FIG. 43. Scheme showing synthesis towards Formula 19.

Figure 44:
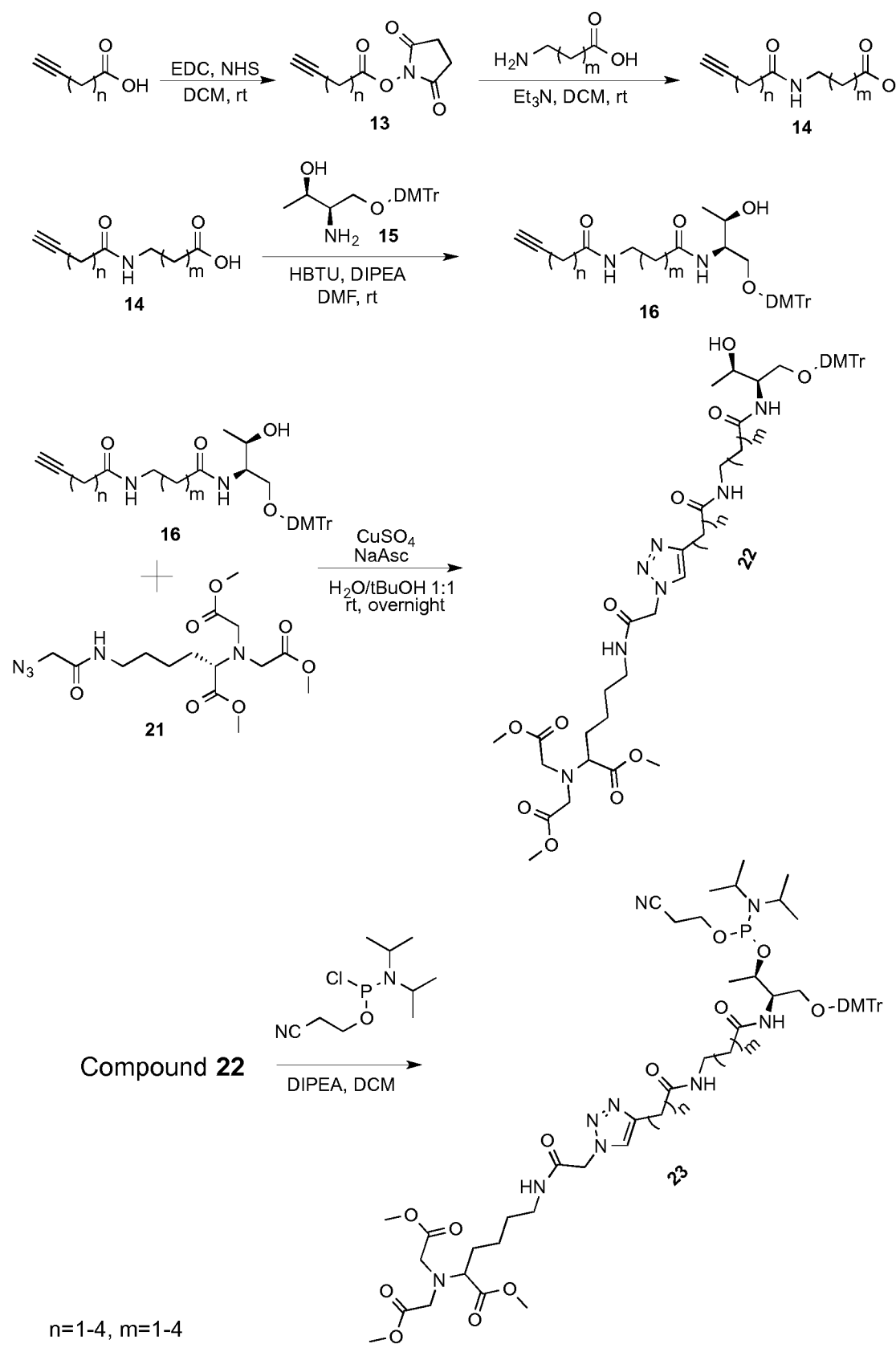

FIG. 44. Scheme showing synthesis towards Formula 19. Compound numbers match n=2, m=4.

Figure 45:
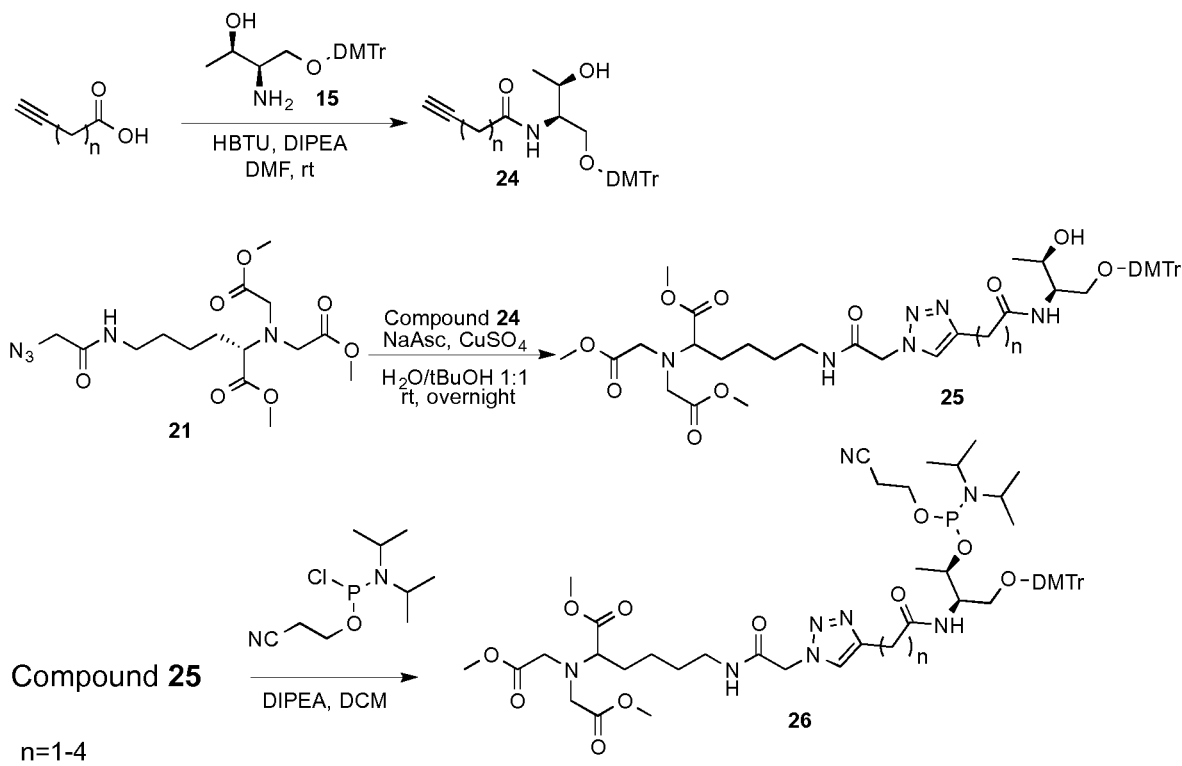

FIG. 45. Scheme showing synthesis towards Formula 19.

Figure 46:
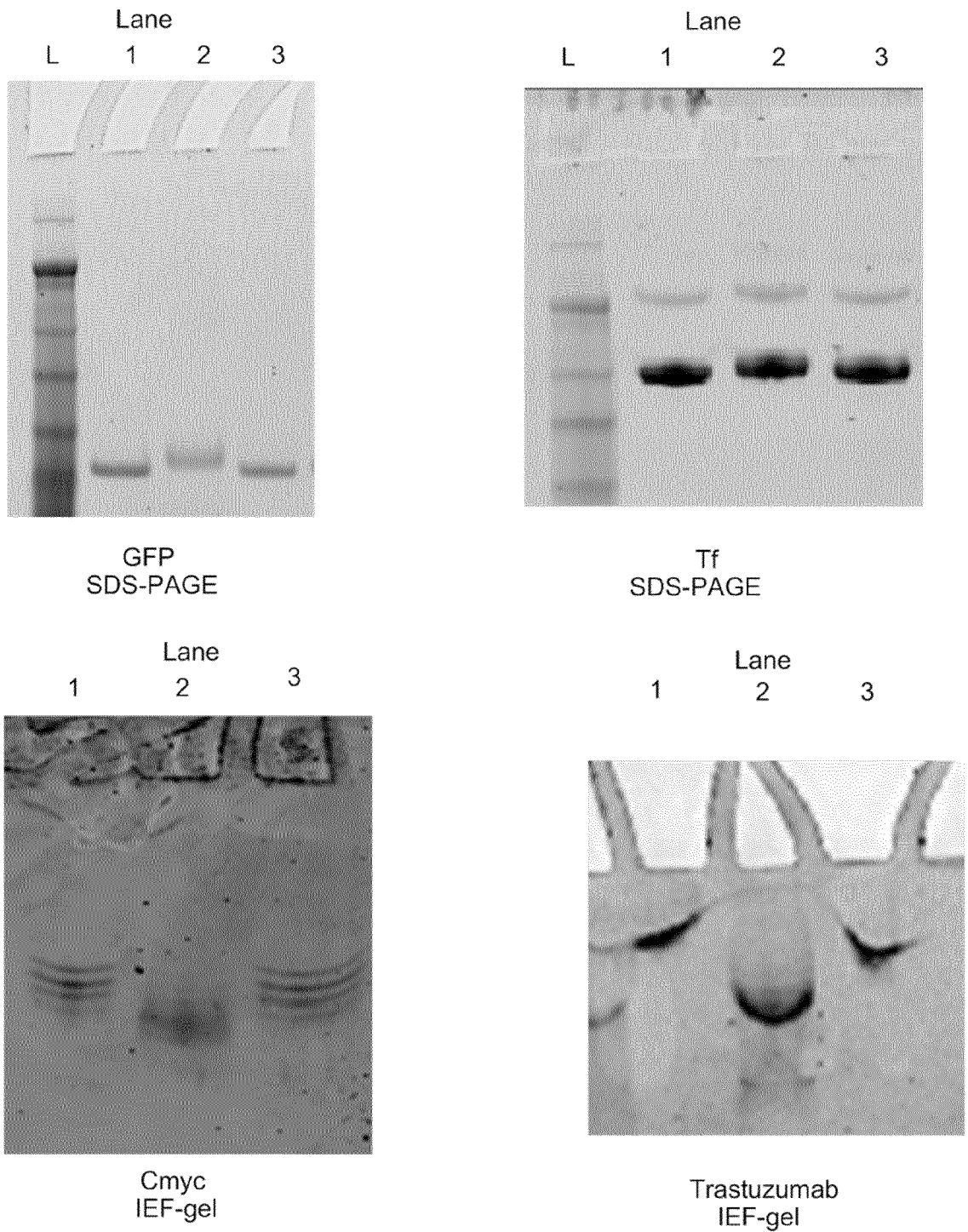

FIG. 46: SDS-PAGE (NuPAGE 4-12% bistris gel) or IEF-gel (Novex® pH 3-7 IEF Protein Gel, LifeTechnologies) for analysis of metal directed conjugation of small molecules (37 or 38) (Example 12). Each gel show selective coupling in the presence of a directing metal in this case CuSO$_4$. In each gel Lane 1: Protein of interest (POI). Lane 2: POI, Small molecule, CuSO$_4$. Lane 3: POI, Small molecule, EDTA. L: SeeBlue® Plus2 Pre-stained Protein Standard.

Figure 47:
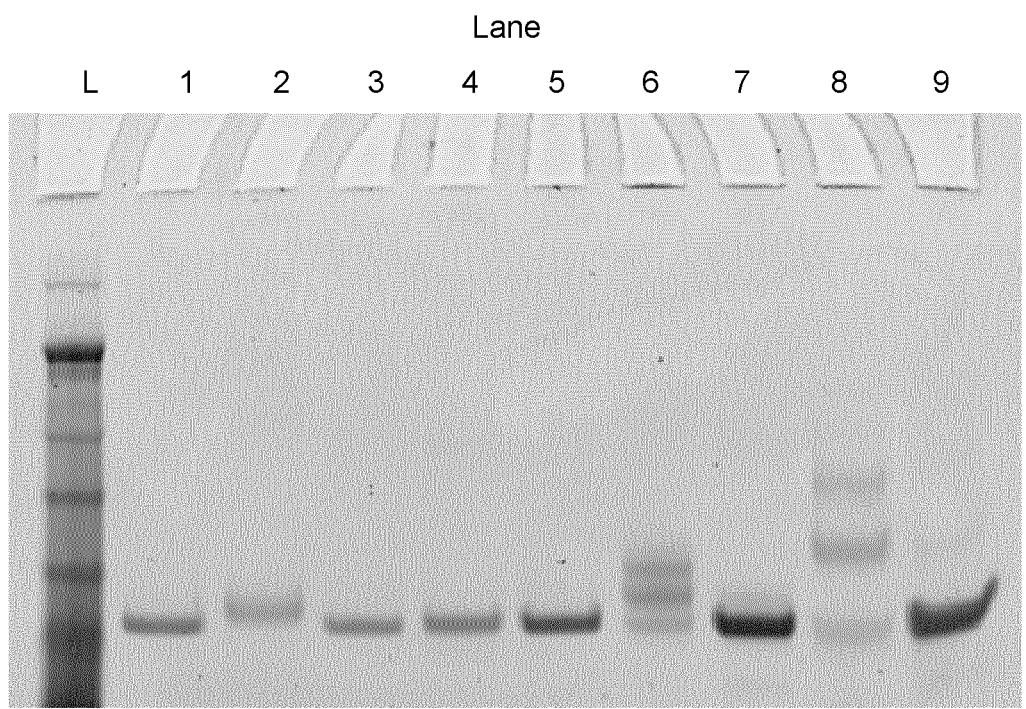

FIG. 47: SDS PAGE analysis of the small molecule reaction sequence of conjugation, cleavage of the dihydroxy linker and coupling to the remaining aldehyde (Example 13). No reaction is seen for in the conjugation reaction when the direction metal was omitted, and the protein lacking the first conjugation reaction does not react further in the sequence. L: SeeBlue® Plus2 Pre-stained Protein Standard. Lane 1: GFP. Lane 2: GFP, small molecule 37, CuSO$_4$. Lane 3: GFP, small molecule 37, EDTA. Lane 4: As lane 2 but with NaIO$_4$ and NaOAc buffer (100 mM, pH 5.5, 0.02% tween 20). Lane 5: As lane 3 but with NaIO$_4$ and NaOAc buffer (100 mM, pH 5.5, 0.02% tween 20). Lane 6: As lane 4 but with PEG(2000)-ONH$_2$ and Phosphate buffer (50 mM, pH 6.5, 0.02% tween 20). Lane 7: As lane 5 but with PEG(2000)-ONH$_2$ and Phosphate buffer (50 mM, pH 6.5, 0.02% tween 20). Lane 8: As lane 4 but with PEG(5000)-ONH$_2$ and Phosphate buffer (50 mM, pH 6.5, 0.02% tween 20). Lane 9: As lane 5 but with PEG(5000)-ONH$_2$ and Phosphate buffer (50 mM, pH 6.5, 0.02% tween 20).

Figure 48:
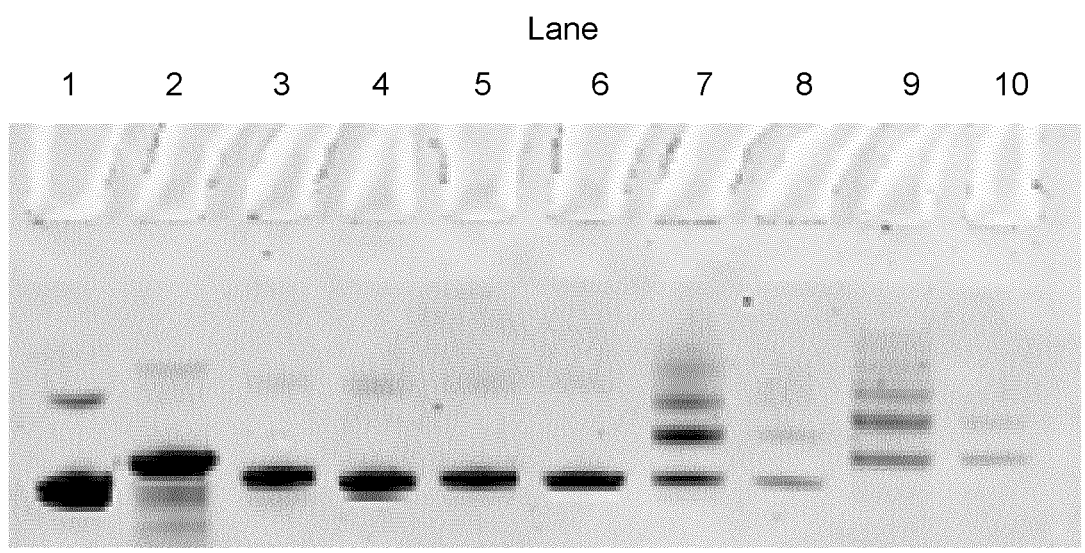

FIG. 48: SDS PAGE analysis of the small molecule reaction sequence of conjugation, cleavage of the azobenzene linker and coupling to the remaining aniline (Example 13). No reaction is seen for in the conjugation reaction when the direction metal was omitted, and the protein lacking the first conjugation reaction does not react further in the sequence. Lane 1: Tf. Lane 2: Tf reduced by DTT. Lane 3: Tf, small molecule 38, CuSO4. Lane 4: Tf, small molecule 38, EDTA. Lane 5: As lane 3 but with $NaS_2O_4$ and Phosphate buffer (25 mM, pH 6.5). Lane 6: As lane 4 but with $Na_2S_2O_4$ and Phosphate buffer (25 mM, pH 6.5). Lane 7: As lane 5 but with o-aminophenol-PEG(10.000), $K_3Fe(CN)_6$ and Phosphate buffer (25 mM, pH 6.5). Lane 8: As lane 6 but with o-aminophenol-PEG(10.000), $K_3Fe(CN)_6$ and Phosphate buffer (25 mM, pH 6.5). Lane 9: As lane 7 but DTT is added to reduce the protein prior to loading the gel. Lane 10: As lane 8 but DTT is added to reduce the protein prior to loading the gel.

Figure 49:
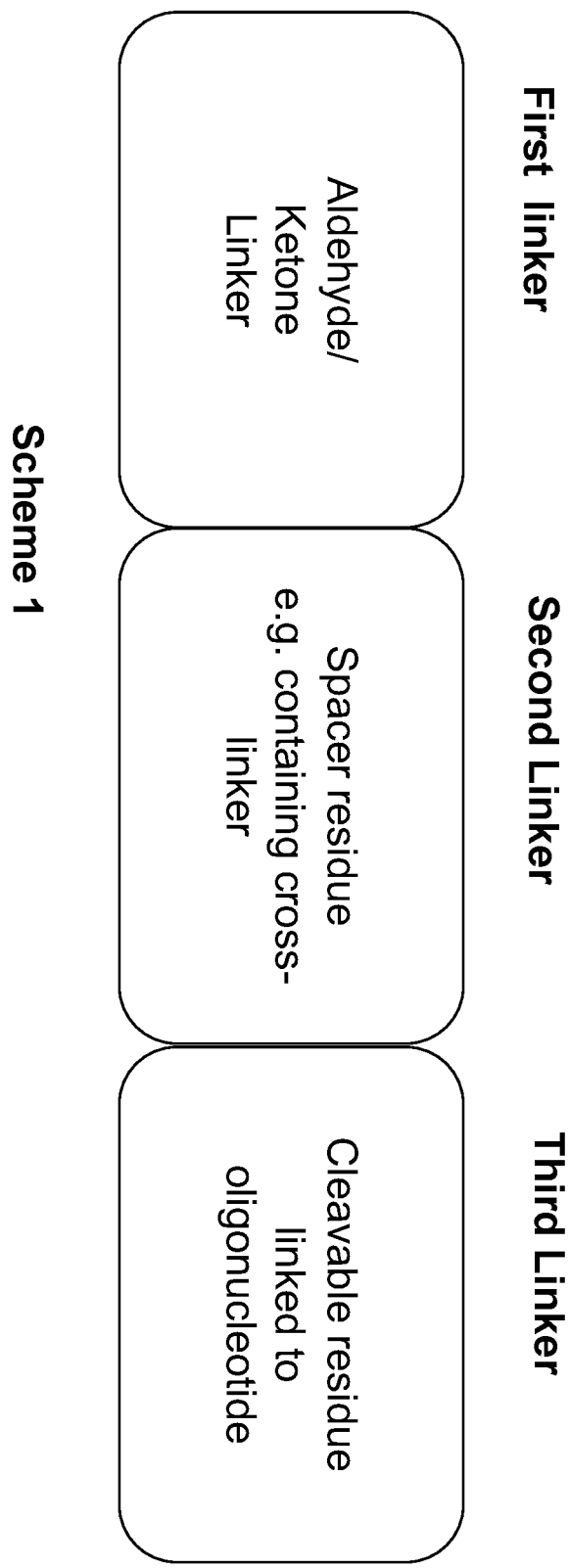
Figure 50:
Figure 51:
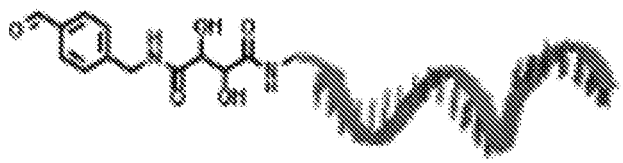
Figure 52:
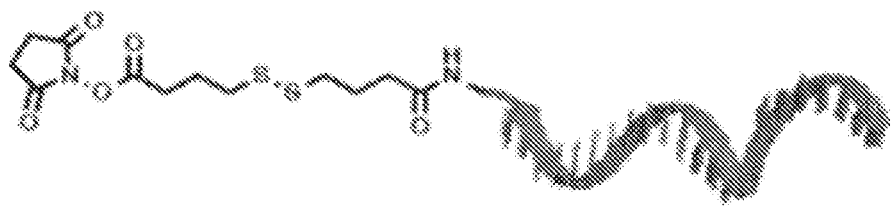
Figure 53:
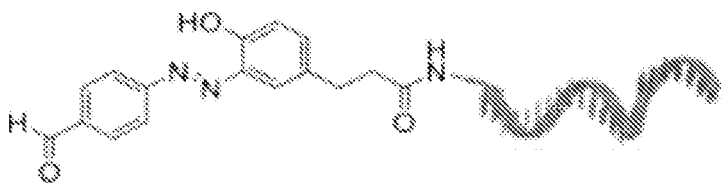

FIG. 49: shows Scheme 1.
FIG. 50 shows compound 3.
FIG. 51 shows compound 7.
FIG. 52 shows compound 9.
FIG. 53 shows compound 12.

DETAILED DESCRIPTION OF THE INVENTION

Definitions

The expression "$C_{1-100}$-alk(en/yn)yl" means $C_{1-100}$-alkyl, $C_{2-100}$-alkenyl or $C_{2-10}$-alkynyl; wherein:

The term "$C_{1-100}$-alkyl" refers to a branched or unbranched alkyl group having from one to 100 carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, [rho]ent-2-yl, pent-3-yl, hex-1-yl, hex-2-yl, hex-3-yl, 2-methyl-4,4-dimethyl-pent-1-yl and hept-1-yl;

The term "$C_{2-100}$-alkenyl" refers to a branched or unbranched alkenyl group having from two to 100 carbon atoms and one double bond, including but not limited to ethenyl, propenyl, and butenyl; and The term "$C_{2-100}$-alkynyl" refers to a branched or unbranched alkynyl group having from two to 100 carbon atoms and one triple bond, including but not limited to ethynyl, propynyl and butynyl.

The expression "$C_{1-10}$ alkylene" refers to a linear or branched alkylene containing 1 to 10 carbon atoms.

The term "$C_{1-8}$-alkyl" refers to a branched or unbranched alkyl group having from one to 8 carbon atoms including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, [rho]ent-2-yl, pent-3-yl, hex-1-yl, hex-2-yl and hex-3-yl.

The term "$C_{3-8}$ carbocycle" refers to a saturated or unsaturated non-aromatic carbocyclic ring having from one to 8 carbon atoms including but not limited to -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_{3-8}$ carbocycle group can be unsubstituted or substituted with one or more groups including, but not limited to, —$C_{1-8}$ alkyl, —O—($C_{1-8}$ alkyl), -aryl, —C(O)R', —OC(O)R', —C(O)OR', —C(O)NH$_2$, —C(O)NHR', —C(O)N(R')2, —NHC(O)R', —S(O)2R', —S(O)R', —OH, -halogen, —N$_3$, —NH$_2$, —NH(R'), —N(R')$_2$ and —CN; where each R' is independently selected from H, —$C_{1-8}$ alkyl and aryl. The term "$C_{3-8}$ carbocyclo" refers to a $C_{3-8}$ carbocycle group defined above wherein one of the carbocycle groups' hydrogen atoms is replaced with a bond.

The term "$C_{3-8}$ heterocycle" refers to an aromatic or non-aromatic $C_{3-8}$ carbocycle in which one to four of the ring carbon atoms are independently replaced with a heteroatom from the group consisting of O, S and N. Representative examples of a $C_{3-8}$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_{3-8}$ heterocycle can be unsubstituted or substituted with up to seven groups including, but not limited to, —$C_{1-8}$ alkyl, —O—($C_{3-8}$ alkyl), -aryl, —C(O)R', —OC(O)R', —C(O)OR', —C(O)NH$_2$, —C(O)NHR', —C(O)N(R')2, —NHC(O)R', —S(O)2R', —S(O)R', —OH, -halogen, —N$_3$, —NH$_2$, —NH(R'), —N(R')$_2$ and —CN; wherein each R' is independently selected from H, —$C_{1-8}$ alkyl and aryl. "$C_{3-8}$ heterocyclo" refers to a $C_{3-8}$ heterocycle group defined above wherein one of the heterocycle group's hydrogen atoms is replaced with a bond. A $C_{3-8}$ heterocyclo can be unsubstituted or substituted with up to six groups including, but not limited to, —$C_{1-8}$ alkyl, —O—(Cl-Cg alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_{1-8}$ alkyl and aryl.

The term "endogenous protein" as used herein means proteins that originate from within an organism, tissue, or cell. The endogenous protein is encoded by an endogenous gene. The endogenous gene can be either a mutant or a wild type endogenous gene.

The term "histidine cluster" as used herein refers to a region or a center, such as the metal binding site, of the metal binding protein that comprises two or more histidine residues. The histidine residues are involved in coordinating a metal ion.

The term "linker" as used herein refers to a chemical compound that is bound directly or indirectly to an oligonucleotide or to the molecule according to formula 11. The linker can be bound indirectly to the oligonucleotide or to the molecule according to formula 11 via another linker or via another chemical compound. The linker can for example be used as a "spacer" between chemical groups. In one embodiment the linker is a cleavable linker.

Conjugation of an Oligonucleotide to a Metal Binding Protein

One object of the present invention is to provide a method for site selective conjugation of DNA conjugates to metal binding proteins. The method presented herein can be used to conjugate DNA and small molecules site-selectively to endogenous metal binding proteins or recombinant proteins carrying a histidine tag.

A first aspect of the present invention thus relates to a method for site selective conjugation of an oligonucleotide conjugate to a metal binding protein comprising a metal binding site as defined above.

In a preferred embodiment, after conjugation of the first oligonucleotide to the metal binding protein, the second oligonucleotide is released from the first oligonucleotide and the protein by toehold mediated strand displacement, using a third oligonucleotide that is complementary to the second oligonucleotide and EDTA to complex the metal ion.

The Metal Binding Protein

The term "metal binding protein" as used herein is a protein or a metalloprotein that can bind a metal ion. The term "metal binding protein" may be used interchangeably with the term "metalloprotein". In metal binding protein or metalloproteins, metal ions are coordinated at the metal binding site. The metal ion coordinated by the metal binding protein can for example be selected from the group consisting of Fe(II), Fe(III), Cu(II), Cu(I), Zn(II), Mg(II), Ca(II), V(III), Co(II), Co(III), Ni(II), Ni(III), Cd(I), Cd(II), Mo(IV), Mo(VI), Sn(II) and Sn(IV). In a preferred embodiment the metal ion is selected from the group consisting of Fe(III), Cu(II) and Ni(II).

The metal binding protein comprises a metal binding site. The metal binding site is usually nitrogen, oxygen or sulfur centers belonging to amino acid residues of the protein. Virtually all amino acid residues can participate in coordinating the metal ion. However, in a preferred embodiment the metal binding site is a histidine cluster. The histidine cluster may comprise at least 2 histidine residues, such as for example at least 3 histidine residues, such as at least 4 histidine residues or such as for example at least 5 histidine residues. It is preferred that the metal binding site is naturally occurring in the metal binding protein, wherein the metal binding protein can be either a mutant or a wild type protein. Thus, it is preferred that the metal binding site is not comprised in or a part of an artificial amino acid sequence that has been fused to the protein by recombinant DNA technology, such as for example a tag or a histidine tag that has been fused to the protein. It is preferred that the metal binding site is encoded by a gene sequence that is found in the genome or is encoded by an endogenous gene sequence. In a preferred embodiment the metal binding site is endogenous.

In another preferred embodiment the metal binding protein is encoded by a gene sequence that is found in the genome or is encoded by an endogenous gene sequence. In a preferred embodiment the metal binding protein is endogenous. It is preferred that the protein is not a recombinant protein. In a preferred embodiment the protein does not comprise a histidine tag, such as a histidine tag that has been fused to the protein by recombinant DNA technology.

The metal binding protein can be selected from the group consisting of metalloenzymes and signal-transduction metalloproteins. In one embodiment the metal binding protein is a metal binding glycoprotein such as for example transferrin. In a preferred embodiment the metal binding protein is an antibody. It is preferred that the antibody comprises a histidine cluster. In a particular embodiment the metal binding protein is an IgG antibody comprising a histidine cluster. It is appreciated that the histidine cluster is in the Fc region of the IgG antibody. In a specific embodiment the IgG antibody, is an IgG1 antibody. In one embodiment is preferred that the antibody is endogenous. In another preferred embodiment the antibody does not comprise a histidine tag, such as a histidine tag that has been fused to the protein by recombinant DNA technology.

In the method according to the present invention, the first oligonucleotide conjugate comprises a reactive chemical group capable of reacting with a nucleophilic amino acid residue in the vicinity of said metal binding site.

The nucleophilic amino acid residue may for example be located in a radius of at most 10 nanometers (nm) from the metal binding site of the metal binding protein, such as for example at most 8 nm from the metal binding site, at most 6 nm from the metal binding site, such as for example at most 5 nm from the metal binding site, at most 4 nm from the metal binding site, such as for example at most 3 nm from the metal binding site or at most 2 nm from the metal binding site. In a preferred embodiment the nucleophilic amino acid residue is located within a radius of at most 1 nm from the metal binding site.

In a preferred embodiment the nucleophilic amino acid residue is a lysine or a cysteine. In a specific embodiment the nucleophilic amino acid residue is a lysine. In another specific embodiment the nucleophilic amino acid residue is a cysteine. In a further embodiment the nucleophilic amino acid residue is a tyrosine.

The First Oligonucleotide Conjugate

The method according to the first aspect of the present invention comprises providing a first oligonucleotide conjugate. Said first oligonucleotide conjugate comprises a reactive chemical group capable of reacting with a nucleophilic amino acid residue in the vicinity of the metal binding site of the metal binding protein.

The oligonucleotide conjugate comprises or consists of an oligonucleotide which is conjugated to a compound or a linker comprising a reactive chemical group.

It is preferred that the oligonucleotide of the first oligonucleotide conjugate comprises at least 7 bases, such as at least 8 bases, at least 9 bases, such as at least 10 bases, at least 11 bases, such as at least 12 bases, at least 13 bases, such as at least 14 bases, at least 15 bases, such as at least 16 bases, at least 17 bases, such as at least 18 bases, at least 19 bases or such as for example at least 20 bases, e.g. at least 21 or 22 bases, for example 22 or 23 bases. The oligonucleotide is in one embodiment an RNA strand. In a preferred embodiment the oligonucleotide is a DNA strand.

Referring to the explanation above regarding the nucleophilic amino acid residue, it follows that the first oligonucleotide conjugate may be conjugated to the protein within a radius of at most 10 nm from the metal binding site of the metal binding protein, such as at most 8 nm, at most 6 nm, at most 5 nm, at most 4 nm, at most 3 nm or at most 2 nm from the metal binding site of the metal binding protein. In one embodiment, the first oligonucleotide conjugate is conjugated to the protein within a radius of at most 1 nm from the metal binding site of the metal binding protein.

The oligonucleotide of the first oligonucleotide conjugate comprises a sequence that is complementary the oligonucleotide of the second oligonucleotide thereby allowing hybridization between the two oligonucleotides. In a specific embodiment the oligonucleotide of the first oligonucleotide conjugate has the sequence 5'-ACATACAGCCTCGCAT-GAGCCC-3' (SEQ ID NO: 1). In yet another embodiment the oligonucleotides are selected from the group consisting of PNA, LNA, xylo-LNA-, phosphorothioate-, 2'-methoxy-, 2'-methoxyethoxy-, morpholino- and phosphoramidate-containing molecules or the like.

The reactive chemical group of the compound that is conjugated to the oligonucleotide is capable of reacting with a nucleophilic amino acid residue. Thus, it is appreciated that the reactive chemical group comprises an electrophile. When the reactive group is brought into proximity with a nucleophilic amino acid residue of the metal binding protein, the nucleophile of the nucleophilic amino acid residue attacks an electrophile of the reactive chemical group thereby forming a new bond between the oligonucleotide conjugate and the metal binding protein. Such a nucleophilic substitution reaction is exemplified in FIG. 2A.

In one embodiment of the present invention the compound comprising the reactive chemical group of the first oligonucleotide conjugate is selected from the group consisting of reactive esters, N-hydroxysulfosuccinimide esters, N-hydroxyphthalimide esters, tetrafluorophenyl esters, p-nitrophenyl esters, thio-esters, phosphate esters, maleimides, Isocyanates, isothiocyanates, acyl fluoride, imidoesters, aldehydes, ketones and 1-fluoro-2-nitrobenzenes.

In a preferred embodiment the compound comprising the reactive chemical group of the first oligonucleotide conjugate is N-hydroxysuccinimide. In a more specific embodiment the compound comprising N-hydroxysuccinimide comprises or consists of the structure of Formula 2:

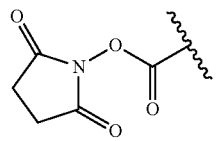

Formula 2

In another preferred embodiment the compound comprising the reactive chemical group of the first oligonucleotide conjugate is an aldehyde or a ketone. Specifically, the compound comprising the reactive chemical group of the first oligonucleotide conjugate is an aldehyde or a ketone in combination with a reducing agent. The reducing agent may for example be selected from the group consisting of sodium borohydride, sodium cyanoborohydride, sodium triacetoxyborohydride and decaborane.

In a specific embodiment the compound comprising the reactive chemical group of the first oligonucleotide conjugate is a phosphate ester group comprising or consisting of the structure of formula 3, or a salt or hydrate thereof:

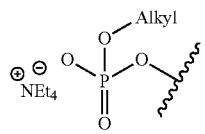

Formula 3

In a preferred embodiment the compound comprising the reactive chemical group is conjugated via a linker attached the first oligonucleotide conjugate. The linker can be attached to either the 3' end or the 5' end of the oligonucleotide.

In a preferred embodiment the linker is an amine linker. In one embodiment the amine linker comprises the structure of Formula 4:

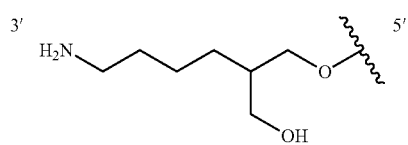

Formula 4

In one embodiment the compound comprising the reactive chemical group is a homo-bifunctional linker that is linked to the oligonucleotide via an amine linker as described above. The homo-bifunctional linker is a linker or a chemical compound comprising two identical functional groups; one of the functional groups can be conjugated to the amine linked oligonucleotide conjugate and the other functional group can be conjugated to the protein.

In one embodiment said homo-bifunctional linker comprises or consists of the structure of Formula 5 or Formula 6:

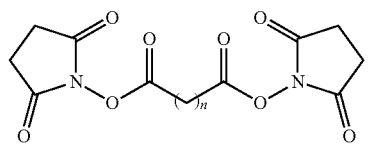

Formula 5 n = 1-10

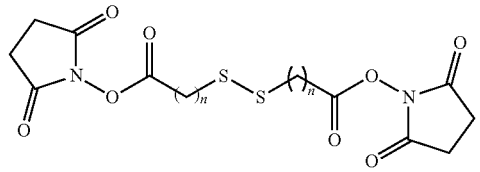

Formula 6 n = 1-10

In another embodiment the homo-bifunctional linker is selected from the group consisting of dimethyl adipimidate.2 HCl, dimethyl pimelimidate.2 HCl, dimethyl suberimidate.2 HCl, dimethyl 3,3'-dithiobispropionimidate.2 HCl, bis(succinimidyl) penta(ethylene glycol), bis(succinimidyl) nona(ethylene glycol), bis(sulfosuccinimidyl) suberate, Bis[2-(succinimidooxycarbonyloxy)ethyl]sulfone, disuccinimidyl glutarate, disuccinimidyl tartarate, 3,3'-dithiobis[sulfosuccinimidylpropionate], 4,4'-dithiobis[sulfosuccinimidylbutenoate], ethylene glycol bis[succinimidylsuccinate], tris-succinimidyl aminotriacetate, and 1,5-difluoro-2,4-dinitrobenzene.

In another embodiment of the present invention the compound comprising the reactive chemical group is a hetero-bifunctional linker that is linked to the oligonucleotide via an amine linker as described above. The hetero-bifunctional linker is a linker or a chemical compound comprising two different functional groups; one of the functional groups can be conjugated to the amine linked oligonucleotide conjugate and the other functional group can be conjugated to the protein.

In one embodiment said hetero-bifunctional linker is selected from the group consisting of sulfosuccinimidyl (4-iodoacetyl) aminobenzoate, succinimidyl (4-iodoacetyl) aminobenzoate, succinimidyl 3-(bromoacetamido)propionate, succinimidyl iodoacetate, sulfosuccinimidyl 4-(N-maleimidomethyl)cyclohexane-1-carboxylate, 2-unit ethyleneglycol functionalized with succinimidyl and maleimido ends, 4-unit ethyleneglycol functionalized with succinimidyl and maleimido ends, 6-unit ethyleneglycol functionalized with succinimidyl and maleimido ends, 8-unit ethyleneglycol functionalized with succinimidyl and maleimido ends, 12-unit ethyleneglycol functionalized with succinimidyl and maleimido ends, 24-unit ethyleneglycol functionalized with succinimidyl and maleimido ends, succinimidyl 4-(N-maleimidomethyl)cyclohexane-1-carboxylate, succinimidyl 4-(N-maleimidomethyl)cyclohexane-1-carboxy-(6-amidocaproate), N-epsilon-maleimidocaproyl-oxysulfosuccinimide ester, N-epsilon-malemidocaproyl-oxysuccinimide ester, N-gamma-maleimidobutyryl-oxysulfosuccinimide ester, N-gamma-maleimidobutyryl-oxysuccinimide ester, N-kappa-maleimidoundecanoyl-oxysulfosuccinimide ester, m-maleimidobenzoyl-N-hydroxysulfosuccinimide ester, m-maleimidobenzoyl-N-hydroxysuccinimide ester, sulfosuccinimidyl 4-(p-maleimidophenyl)butyrate, succinimidyl 4-(p-maleimidophenyl)butyrate, N-alpha-maleimidoacetoxysuccinimide ester, N-beta meleimidopropyl-oxysuccinimide ester and succinimidyl 6-[(beta-maleimidopropionamido)hexanoate].

In one embodiment the homo-bifunctional linker and/or the hetero-bifunctional linker is cleaved photochemically, by reduction, by oxidation, by bases, by acids, enzymatically and/or by fluoride.

In one embodiment of the present invention the first oligonucleotide conjugate comprises
- a first linker comprising the reactive group, said reactive group being an aldehyde or a ketone
- a second linker selected from the group consisting of $C_{1-20}$-alkane, $PEG_{1-20}$, compounds comprising a phenyl group and compounds comprising an aryl group and,
- a third linker which is a cleavable linker located between the second linker and the oligonucleotide of the first oligonucleotide conjugate wherein said first linker, said second linker and said third linker are covalently linked.

A schematic presentation of the first oligonucleotide comprising three linkers are shown in FIG. 49.

Scheme 1

| First linker | Second linker | Third linker |
|---|---|---|
| Aldehyde Ketone linker | Spacer residue e.g. containing cross linker | Cleavable residue linked to oligonucleotide |

The first linker comprises the reactive group which in this case is and aldehyde or a ketone. The aldehyde or the ketone comprising the reactive group is capable of reacting with a nucleophilic amino acid residue on the metal binding protein. The aldehyde or ketone of the first linker can react with an amine on the metal binding protein by reductive amination thereby linking the reactive group to the metal binding protein. The first linker is covalently linked to the second linker.

The second linker is located between the first linker and the third linker. It is preferred that the second linker is covalently bound directly to the first linker and the third linker. Thus, the second linker functions as a spacer between the first and the third linker. In a preferred embodiment the second linker comprises a functional chemical group selected from the group consisting of alkynes, azides, acetals, ketals, tetrazines and alkenes. In a preferred embodiment the linker may contain a functional group that can be used to form a covalent bond to another compound such as for example a drug molecule or a cytotoxic agent.

The third linker is a cleavable linker located between the second linker and the oligonucleotide of the first oligonucleotide conjugate. The third linker is covalently linked to the second linker.

In one embodiment the third linker is cleaved photochemically, by reduction, by oxidation, by bases, by acids, enzymatically and/or by fluoride.

The third linker is in one embodiment selected from the group consisting of dialkyl dialkoxysilane, cyanoethyl, sulfone, ethylene glycolyl disuccinate, 2-N-acyl nitrobenzenesulfonamide, α-thiophenylester, unsaturated vinyl sulfide, sulfonamide, malondialdehyde (MDA)-indole derivative, levulinoyl ester, hydrazone, acylhydrazone, alkyl thioester, azo compounds, 2-nitrobenzyl derivatives, phenacyl ester, 8-quinolinyl benzenesulfonate, coumarin, phosphotriester, bis-arylhydrazone, bimane bi-thiopropionic acid derivative" paramethoxybenzyl derivative, tert-butylcarbamate analogues, dialkyl or diaryl dialkoxysilane, orthoester, acetal, aconityl, hydrazone, β-thiopropionate, phosphoramidate, imine, trityl, vinyl ether, polyketal, alkyl 2-(diphenylphosphino)benzoate derivatives, allyl ester, 8-hydroxyquinoline ester, picolinate ester, vicinal diols and selenium compounds.

In another embodiment said third linker is an oxidatively cleavable linker. The oxidatively cleavable linker may for example comprise the structure of Formula 7 or 8:

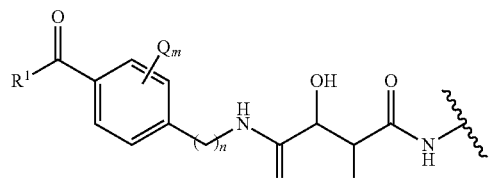

Formula 7

Formula 8 wherein
n is 1, 2, 3, 4, 5, 6, 7, 8, 9, 10, 11 or 12
m is 0, 1, 2, 3 or 4
$R^1$ is selected from the group consisting of —H, trifluoromethyl, aldehyde, —$C_{1-100}$-alk(en/yn)yl, —$C_{1-100}$-alkoxy, -acyloxy, -sulfhydryl, -nitro and -azide
Q is selected from the group consisting of —$C_{1-100}$-alk(en/yn)yl, —$C_{1-100}$-alkoxy, -acyloxy, -halogen, -cyano, -nitro, -carboxy, -acyl, -amino, -hydroxyl, -acyloxy, -amide, -sulfhydryl, -sulfoxide, -sulfone, -sulfonyl and -azide.

In a further embodiment the linker is a reducible cleavable linker comprising or consisting of the structure of Formula 9 or 10:

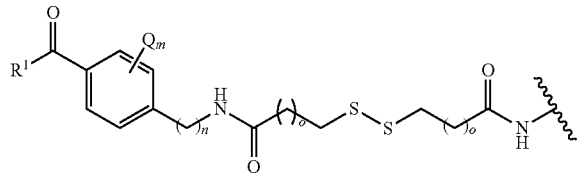

Formula 9

Formula 10 wherein
n is 1,2, 3, 4, 5, 6, 7, 8, 9, 10, 11 or 12
m is 0, 1,2, 3 or 4 o is 1,2, 3, 4, 5, 6, 7, 8, 9 or 10

$R^1$ is selected from the group consisting of —$C_{1-100}$-alk(en/yn)yl, —$C_{1-100}$-alkoxy, -sulfhydryl, -nitro and -azide Q is selected from the group consisting —$C_{1-100}$-alk(en/yn)yl, —$C_{1-100}$-alkoxy, -halogen, -cyano, -nitro, -carboxy, -acyl, -amino, -hydroxyl, -acyloxy, -amide, -sulfhydryl, -sulfoxide, -sulfone, -sulfonyl and -azide.

When the first oligonucleotide conjugate comprising a cleavable linker has been conjugated to the metal binding protein, the linker can be cleaved thereby leading to dissociation of the oligonucleotide from the protein while a part of the linker will still be conjugated to the protein.

The cleavable linker can be any of the cleavable linkers described herein. It is preferred that the compound which is conjugated to the protein after cleavage of the linker comprises a functional chemical group to which another chemical compound, such as for example a cytotoxic compound, can be conjugated. For example, upon cleavage of the third linker as described above, a part of the linker will be attached or conjugated to the protein. This part of the linker may comprise a functional chemical group, such as for example an aldehyde, that can be applied for subsequent linking of a drug molecule derivative. The linker may also be any cleavable linker that can be cleaved under conditions that are compatible with the chemistry of the protein.

This can be exemplified by an oligonucleotide which is conjugated to the protein via a dihydroxy-linker, such as for example the linker according Formula 7 or 8. The dihydroxy-linker can be cleaved by sodium periodate, thereby leaving a functional chemical group conjugated to the protein.

Thus, in one embodiment the method according to the first aspect of the present invention comprises a further step of cleaving a cleavable linker of the first oligonucleotide conjugate thereby leading to dissociation of the oligonucleotide of the first oligonucleotide conjugate from the protein. In a preferred embodiment a functional chemical group is conjugated to the metal binding protein after cleavage and dissociation of the oligonucleotide. Thus, in one embodiment the method according to the first aspect of the present invention comprises still a further step of conjugating a chemical compound, such as for example a cytotoxic compound, to the functional chemical group.

The Second Oligonucleotide Conjugate

The method according to the first aspect of the present invention comprises providing a second oligonucleotide conjugate capable of hybridizing to the first oligonucleotide conjugate and wherein said second oligonucleotide is conjugated to at least one ligand capable of binding a metal at the metal binding site of the metal binding protein.

It is preferred that the oligonucleotide of the second oligonucleotide conjugate comprises at least 7 bases, such as at least 8 bases, at least 9 bases, such as at least 10 bases, at least 11 bases, such as at least 12 bases, at least 13 bases, such as at least 14 bases, at least 15 bases, such as at least 16 bases, at least 17 bases, such as at least 18 bases, at least 19 bases or such as for example at least 20 bases, e.g. at least 21, 22, 23 or 24 bases, such as 22 or 23 bases. The oligonucleotide is in one embodiment an RNA strand. In a preferred embodiment the oligonucleotide is a DNA strand. In a specific embodiment the oligonucleotide of the second oligonucleotide conjugate has the sequence 5'-GGGCT-CATGCGAGGCTTACGAAC-3' (SEQ ID NO: 2).

The oligonucleotide of the second oligonucleotide conjugate comprises a sequence that is complementary or, typically, partially complementary to the oligonucleotide of the first oligonucleotide thereby allowing hybridization between the two oligonucleotides. In a specific embodiment the oligonucleotide of the first oligonucleotide conjugate has the sequence 5'-ACATACAGCCTCGCATGAGCCC-3' (SEQ ID NO: 1).

The second oligonucleotide conjugate comprises or consists of an oligonucleotide which is conjugated to a ligand capable of binding a metal at the metal binding site of the metal binding protein.

In one embodiment the ligand comprises or consists of at least one of the molecules selected from the group consisting of iminodiacetic acid, pentetic acid, diethylene triamine pentaacetic acid (DPTA), ethylenediaminetetraacetic acid (EDTA), aminosalicyclic derivatives, 8-hydroxyquinoline, carboxymethylated amino acids, terpyridine and bis(2-pyridylmethyl) amine derivatives.

In one embodiment the ligand comprises or consists of at least one nitrilotriacetic acid (NTA) moiety. In a preferred embodiment the ligand comprises or consists of at least two NTA moieties. In another embodiment the ligand comprises or consists of at least three NTA moieties, such as for example at least 4 NTA moieties, such as at least 5 NTA moieties or such as for example at least 6 NTA moieties. It is appreciated that increasing the number of NTA moieties increases the affinity between ligand and the metal binding site of the protein.

The ligand can be conjugated to either the 5' end of the oligonucleotide of the second oligonucleotide conjugate or it can be conjugated to the 3' end of the oligonucleotide of the second oligonucleotide conjugate.

In one embodiment of the present invention the ligand is conjugated via a linker to the second oligonucleotide. In a preferred embodiment said linker is an amine linker.

In an embodiment the amine linker may comprise or consist of the structure of Formula 11:

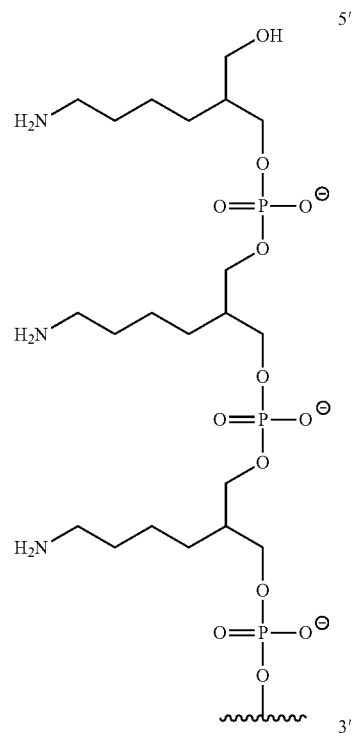

Formula 11

In a second embodiment the second oligonucleotide conjugate is synthesized via solid-phase oligonucleotide synthesis with a ligand-phosphoramidite.

The ligand-phosphoramidite can be conjugated to either the 5' end of the oligonucleotide of the second oligonucleotide conjugate or it can be conjugated to the 3' end of the oligonucleotide of the second oligonucleotide conjugate.

In an embodiment the ligand-phosphoramidite comprises or consists of the ligand part, a linker region and a phosphoramidite moiety.

The ligand part should consist or comprise of a protected version of the molecules selected from the group consisting of iminodiacetic acid, pentetic acid, diethylene triamine pentaacetic acid (DPTA), ethylenediaminetetraacetic acid (EDTA), aminosalicyclic derivatives, 8-hydroxyquinoline, carboxymethylated amino acids, nitrilotriacetic acid (NTA) and bis(2-pyridylmethyl) amine derivatives in order not to interfere with the oligonucleotide synthesis.

In an embodiment the ligand is deprotected during the cleavage and deprotection step after the oligonucleotide synthesis.

In a preferred embodiment the ligand-phosphoramidite is a protected-NTA phosphoramidite.

In one embodiment the linker region is selected from the group consisting of —$C_{1-10}$ alkylene-, —$C_{3-8}$ carbocyclo-, —O—($C_{1-8}$ alkyl)-, -arylene-, —$C_{1-10}$ alkylene-arylene-, -arylene-$C_{1-10}$ alkylene-, —$C_{1-10}$ alkylene-($C_3$-$C_8$ carbocyclo)-, —($C_{3-8}$ carbocyclo)-$C_1$-$C_{10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, —($CH_2CH_2O$)r-, and —($CH_2CH_2O$)r-$CH_2$—, —($C_{1-10}$—CONH—$C_{1-10}$)r-; wherein r is an integer ranging from 1-10, or a combination thereof.

In an embodiment the phosphoramidite moiety is based upon the backbone structure of acyclic (L)-threoninol nucleic acid (aTNA).

In an embodiment the protected-NTA phosphoramidite may comprise or consist of the structure of Formula 12, 13, 14 or 15:

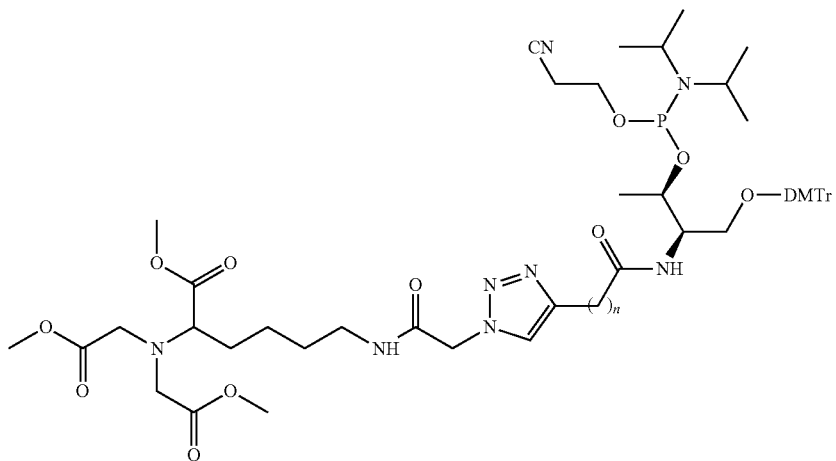

Formula 12

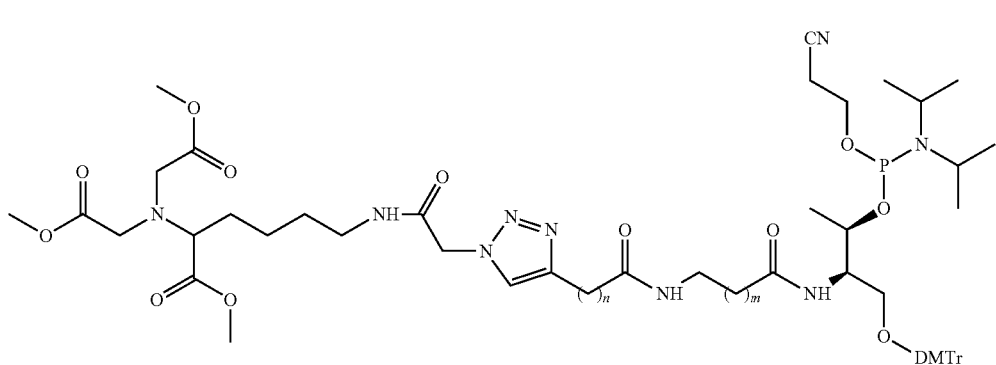

Formula 13

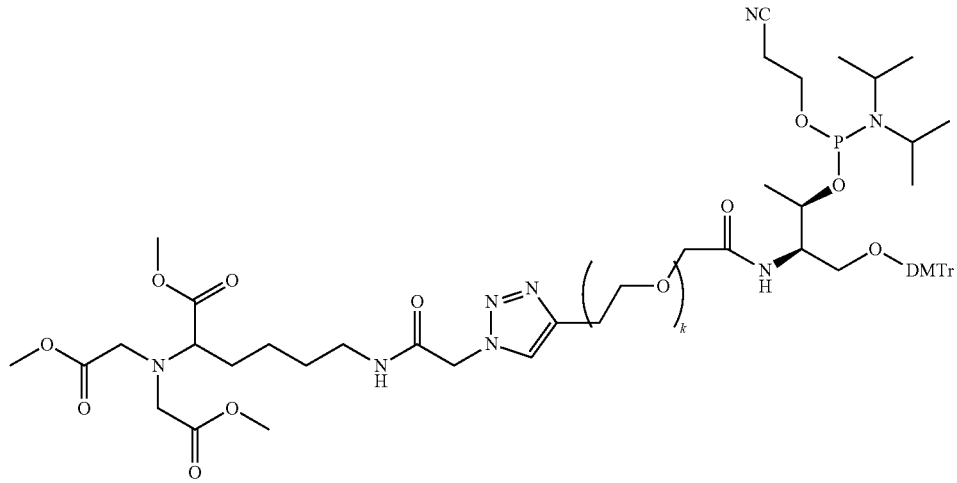

Formula 14

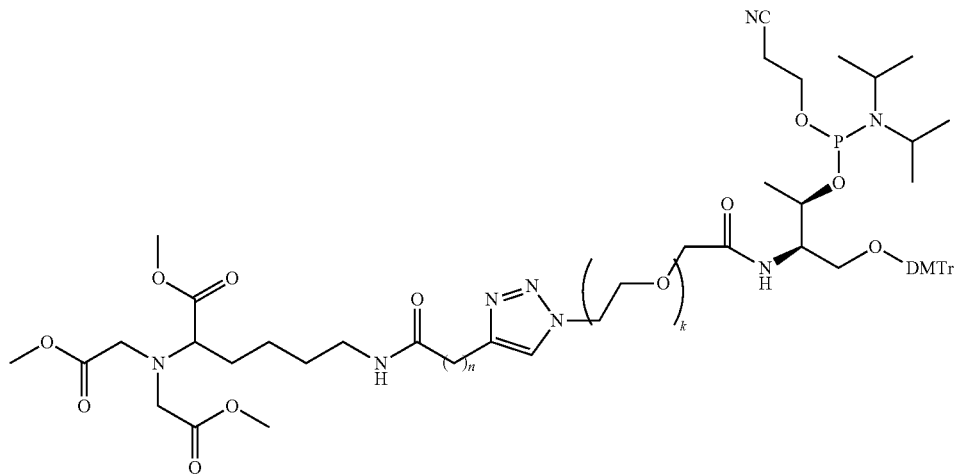

Formula 15 wherein:
n is 1, 2, 3 or 4
m is 1, 2, 3 or 4
k is 1, 2, 3, 4 or 5.

In a preferred embodiment said metal binding site is a histidine cluster. It is also preferred that the metal binding protein is an IgG antibody comprising a histidine cluster. In a specific embodiment the histidine cluster is located in the Fc region of the IgG antibody.

In one embodiment, the nucleophilic amino acid residue is a lysine, cysteine or tyrosine, preferably lysine.

The ligand may in one embodiment comprise or consist of at least one of the molecules selected from the group consisting of iminodiacetic acid, pentetic acid, diethylene triamine pentaacetic acid (DPTA), ethylenediaminetetraacetic acid (EDTA), aminosalicyclic derivatives, 8-hydroxyquinoline, carboxymethylated amino acids, terpyridines and bis(2-pyridylmethyl) amine derivatives.

In a preferred embodiment the ligand comprises or consists of at least one nitrilotriacetic acid (NTA) moiety. In another preferred embodiment the ligand comprises or consists of two or three nitrilotriacetic acid (NTA) moieties.

Conjugation of a Small Molecule Conjugation Compound to an Antibody

A second aspect of the present invention relates to a method for site selective conjugation of a small molecule conjugation compound (SMCoC) to an antibody comprising a metal binding site as defined above using a small molecule conjugation compound (SMCoC) comprising or consisting of the following structure:

Formula 1

The antibody used in this aspect of the invention is as defined elsewhere herein. Thus, in a preferred embodiment the metal-binding site is a histidine cluster, in particular where the antibody is an IgG antibody comprising a histidine cluster. In a particular embodiment, the histidine cluster is located in the Fc region of the IgG antibody. In another preferred embodiment the nucleophilic amino acid residue is a lysine, tyrosine or a cysteine, preferably a lysine.

In one embodiment the electrophile E comprises a chemical group selected from aldehydes, ketones, isocyanates, isothiocyanates, diazirines, arylazides, benzophenones, NHS-esters, N-hydroxsulfosuccinimide esters, N-hydroxysuccimide esters, N-hydroxyphtalimide esters, pentafluorophenyl esters, p-nitrophenyl esters, thio-ester, phosphate esters, maleimides, acyl fluorides, imidoesters, and 1-fluoro-2-nitrobenzene. Non-limiting examples of such groups include those shown below: E:

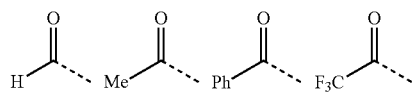

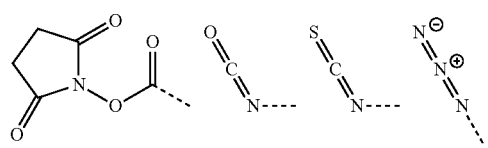

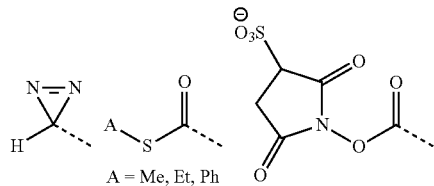

-continued

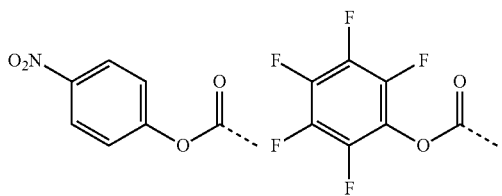

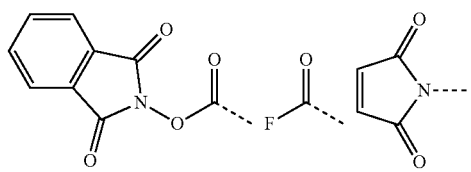

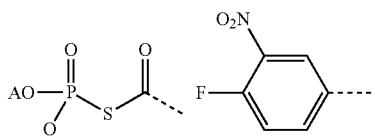

A = Me, Et, Ph

In one embodiment, E is a carbonyl or an acyl group.

If E is an aldehyde or ketone, a reductant such as $NaBH_3CN$ or $NaB(OAc)_3$ is typically added to provide coupling by reductive amination.

In one preferred embodiment the SMCoC is selected from molecules having the structure shown below (Formula 16):

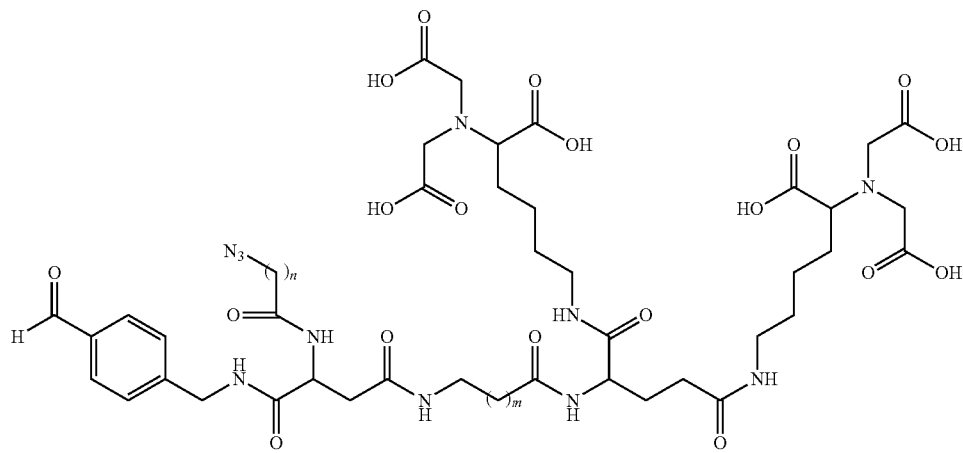

n = 1-10, m = 0-16

In one embodiment, Z is selected from phenyl, aryl, heteroaryl, alkyl, alkyl amide, and alkyl amine. As it will be apparent from the definition of the SMCoC of formula 1 above, R, $S^2$ and/or Z may be omitted. Examples below include structures where $S^2$ are omitted:
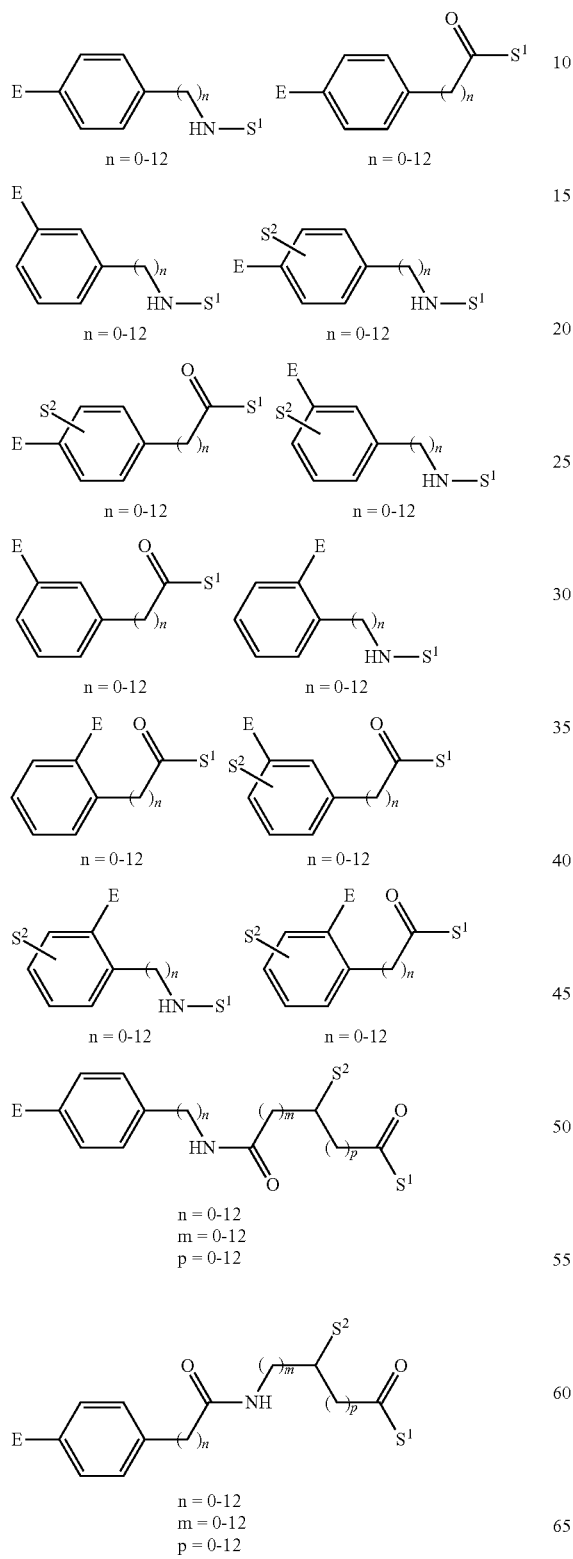
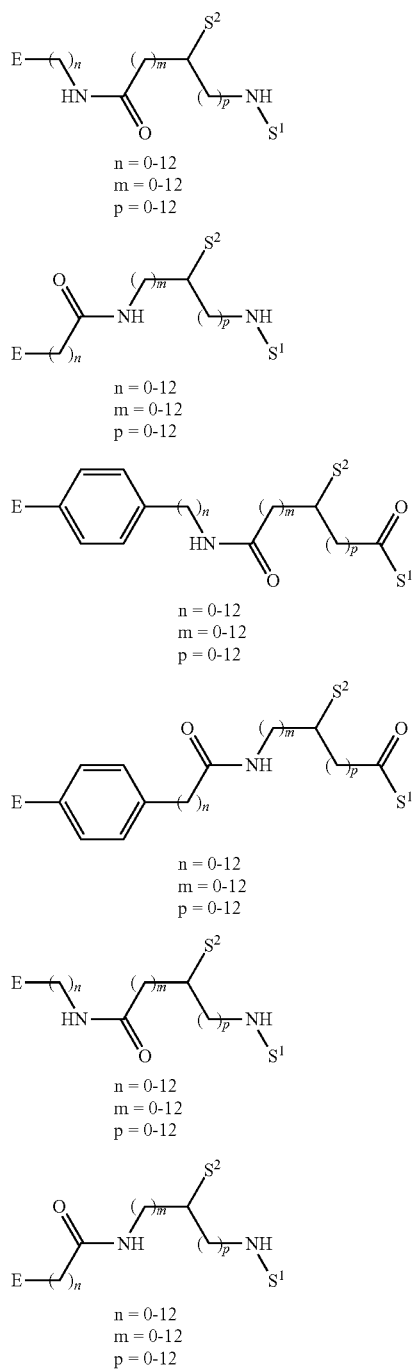
In one embodiment $S^2$ is selected from the compounds illustrated below:
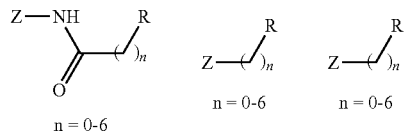

-continued

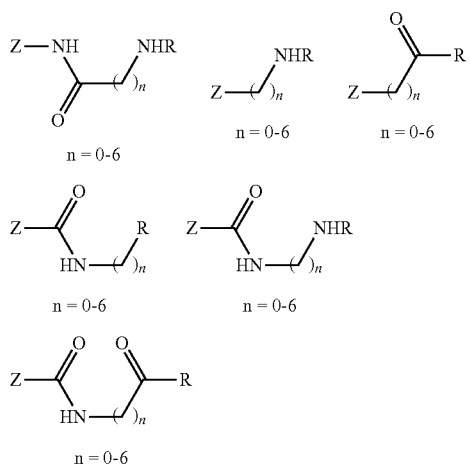

n = 0-6

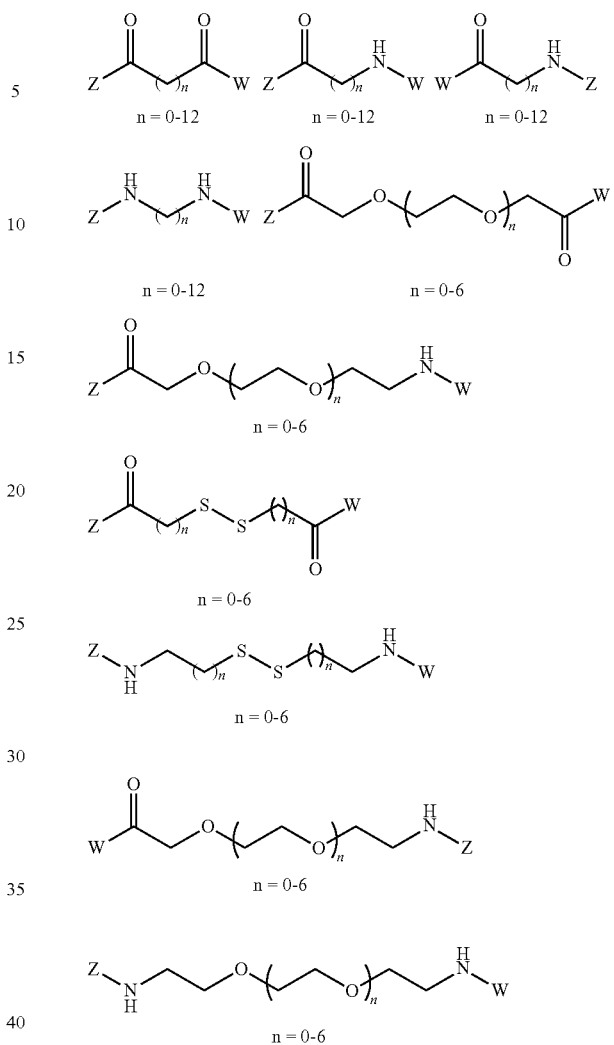

In another embodiment $S^2$ comprises a linker that can be cleaved in vivo and release R, such as a disulfide, a hydrazone, cis-aconityl, p-amidobenzyl ethers or β-glycoronic acid.

In one embodiment R comprises a moiety containing a chemical group such as an azide, an alkyne, a diene or a tetrazine to which another chemical compound can be conjugated. Non-limiting examples of such R groups include those shown below:

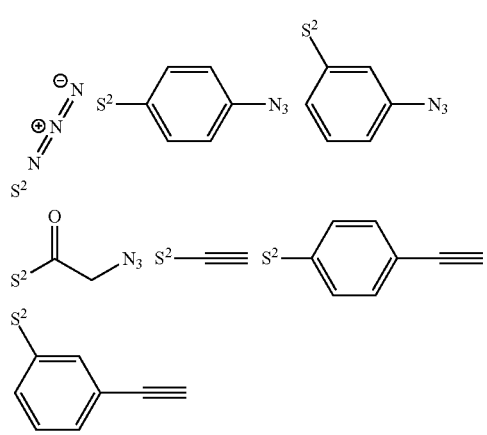

In another embodiment, the compound reacting with R may contain a moiety selected from an alkyne, an alkene, an azide, a diene or a tetrazine.

In one embodiment $S^2$ is omitted and R is linked directly to Z.

In a specific embodiment R further comprises a functional group that can be used to form a covalent bond to another compound. Thus, in one embodiment the method according to the second aspect of the present invention further comprises a step of conjugating a chemical compound to R.

In one embodiment said compound conjugated to R is selected from the group consisting of drugs, dyes and fluorophores.

In one embodiment $S^1$ is selected from the group consisting of:

In another embodiment $S^1$ is selected from the group consisting of —$C_{1-10}$ alkylene-, —$C_{3-8}$ carbocyclo-, —O—($C_{1-8}$ alkyl)-, -arylene-, —$C_{1-10}$ alkylene-arylene-, -arylene-$C_{1-10}$ alkylene-, —$C_{1-10}$ alkylene-($C_3$-$C_8$ carbocyclo)-, —($C_{3-8}$ carbocyclo)-$C_1$-$C_{10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, —(CH$_2$CH$_2$O)r-, and —(CH$_2$CH$_2$O)r-CH$_2$—; wherein r is an integer ranging from 1-10.

In another embodiment $S^1$ is selected from the group consisting of cleavable linkers cleaved photochemically or by oxidation, reduction, acid, base, enzymatically or fluoride.

In one embodiment the ligand W comprises or consists of at least one of the ligands L selected from the group consisting of nitrilotriacetic acid (NTA), iminodiacetic acid, pentetic acid, diethylene triamine pentaacetic acid (DPTA), 1,4,7,10-tetra-azacylcododecane-N,N',N'',N'''-tetraacetic acid (DOTA), ethylenediaminetetraacetic acid (EDTA), aminosalicyclic derivatives, 8-hydroxyquinoline, carboxymethylated amino acids and bis(2-pyridylmethyl) amine derivatives. Non-limiting examples of such ligands L include those shown below:

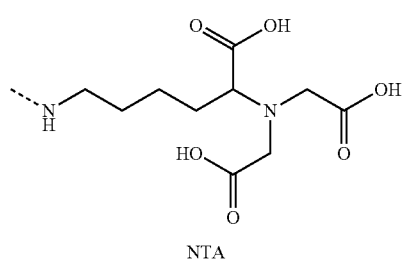

NTA

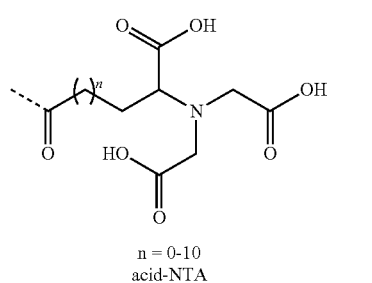

n = 0-10
acid-NTA

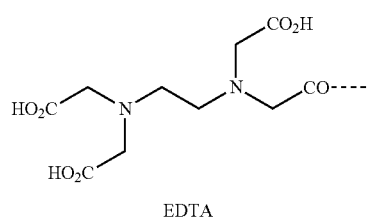

EDTA

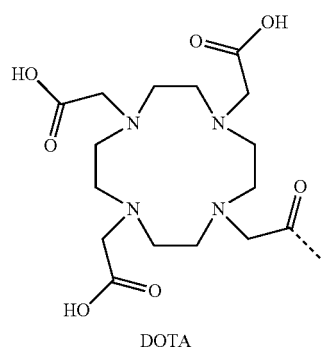

DOTA

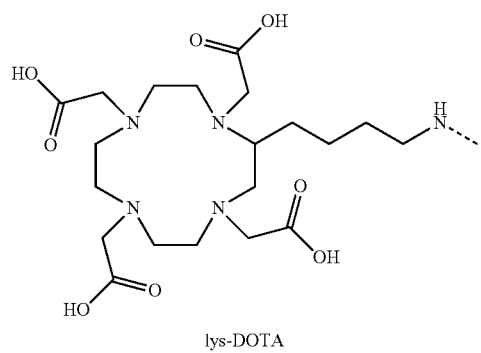

lys-DOTA

-continued

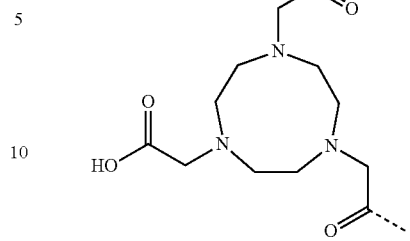

NONA

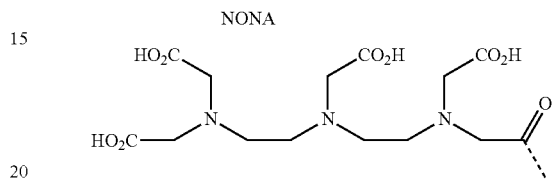

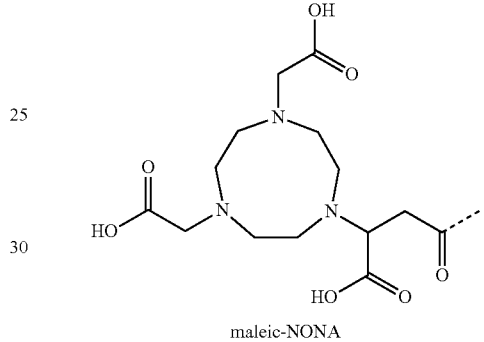

maleic-NONA

The invention also embodies ligands L shown above where the ligand is extended via the dotted line to a diamine of the form —HN(CH$_2$)$_n$NH— (n=2-10).

In another embodiment W comprises a two, three or four way branching unit B linked to the ligands L mentioned above in the format W=BL$_2$, BL$_3$, or BL$_4$. Examples of such branching moieties are shown below:

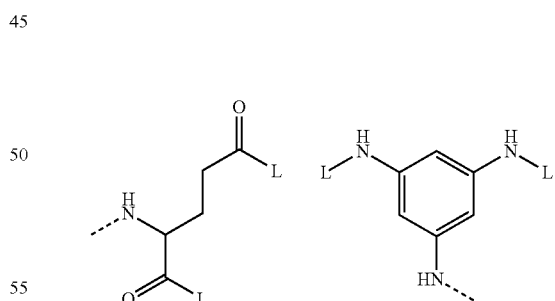

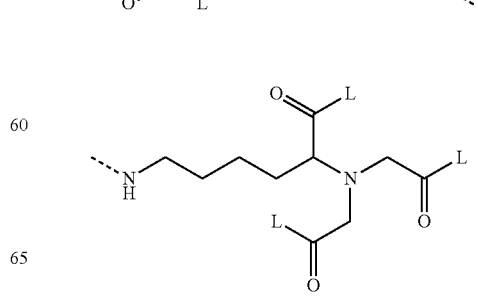

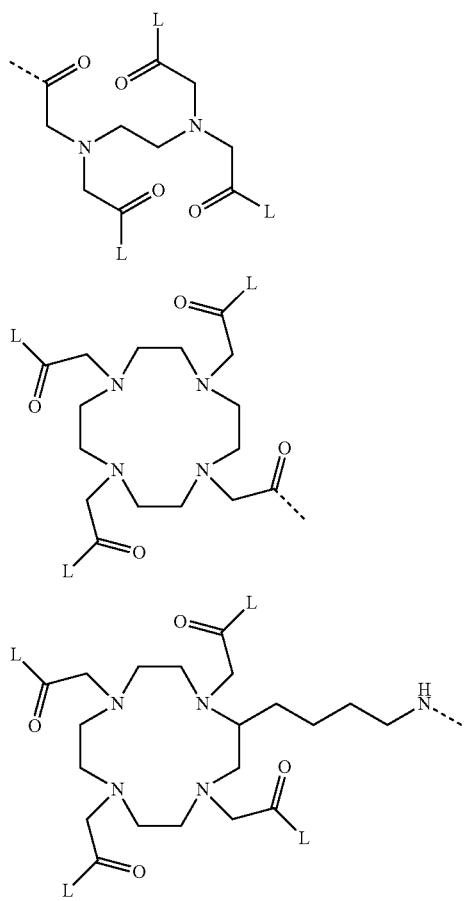

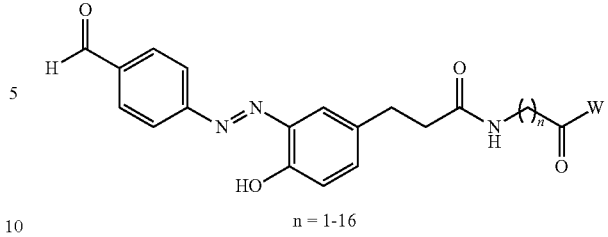

n = 1-16

In a preferred embodiment the compound conjugated to R is biotin or a fluorescent compound selected from a group consisting of xanthenes, cyanines, squaraines, naphtalenes, coumarins, oxadiazoles, antracenes, pyrenes, oxazines, acridines, arylmethines and tetrapyrroles.

In a preferred embodiment the compound conjugated to R is a cytotoxic agent. The cytotoxic agent is in one embodiment selected from the group consisting of toxins, antibiotics, radioactive isotopes and nucleolytic enzymes. In one embodiment thereof, the cytotoxic agent is a toxin selected from the group consisting of doxorubicin derivatives, maytansinoids, auristatins, calicheamicins, CC-1065, duocarmycins and antracyclines.

Metal Binding Protein Conjugates

A third aspect of the present invention relates to a metal binding protein conjugate obtainable by the method according to the first or second aspect of the present invention. This metal binding protein conjugate thus comprises the first oligonucleotide conjugated to a metal binding protein according to the method of the first aspect of the invention, or a small molecule conjugated to an antibody according to the method of the second aspect of the invention.

Oligonucleotide Conjugates

In the case of oligonucleotide conjugates, in a preferred embodiment the metal binding site of the metal binding protein is a histidine cluster. In one embodiment, the metal binding protein is an antibody, preferably an IgG antibody. In a specific embodiment, the histidine cluster is located in the Fc region of the IgG antibody.

In one embodiment the first oligonucleotide conjugate is conjugated to the metal binding protein within a radius of at most 3 nanometers from the metal binding site.

In one embodiment the first oligonucleotide conjugate is conjugated to the protein via a non-cleavable linker. In a preferred embodiment the first oligonucleotide conjugate is conjugated to the protein via a cleavable linker.

In a preferred embodiment the metal binding protein conjugate comprises a functional chemical group to which a cytotoxic agent can be conjugated. Said cytotoxic agent is in one embodiment selected from the group consisting of toxins, antibiotics, radioactive isotopes and nucleolytic enzymes. In a more specific embodiment the cytotoxic agent is a toxin selected from the group consisting of doxorubicin derivatives, maytansinoids, auristatins, calicheamicins, CC-1065, duocarmycins, azonatides, PDB dimers and antracyclines.

In one embodiment the metal binding protein conjugate is conjugated to a cytotoxic agent via a linker that is cleavable under photo, oxidizing, reducing, enzymatic, basic or acidic conditions.

Small Molecule-Antibody Conjugates

In the case of a small molecule conjugated to an antibody, in a preferred embodiment the metal binding site is a In one embodiment the Z, $S^2$ and R groups of SMCoC as shown in Formula 15 are omitted and the SMCoC has the general structure E-$S^1$—W. In this particular embodiment $S^1$ is preferably a cleavable linker that leaves a reactive functional group after cleavage. Examples of such compounds include but are not limited to those shown below:

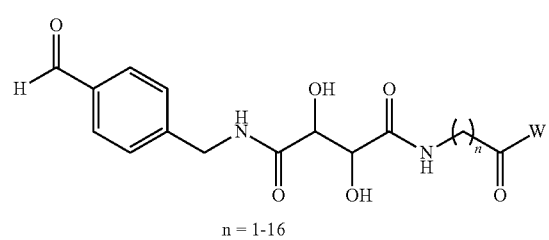

n = 1-16

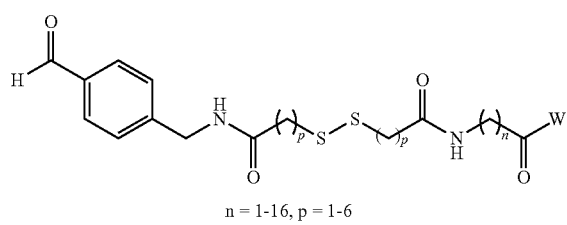

n = 1-16, p = 1-6 histidine cluster. Preferably, the antibody is an IgG antibody comprising a histidine cluster. In a specific embodiment the histidine cluster is located in the Fc region of the IgG antibody.

In one embodiment the reactive group E of the small molecule SMCoC of the general Formula 1 is conjugated to the antibody within a radius of less than 10 nanometers (nm) from the metal binding site of the antibody, such as for example at most 8 nm from the metal binding site, at most 6 nm from the metal binding site, such as for example at most 5 nm from the metal binding site, at most 4 nm from the metal binding site, such as for example at most 3 nm protein, typically an antibody, is removed by a chelating agent, e.g. EDTA, and subsequently replaced by a radioactive metal isotope such as Gallium-68, Copper-64, Copper-67, Yttrium-86, Zirconium-89, Scandium-44, Yttrium-90, Rhenium-188, Lutetium-177, Bismuth-212, Bismuth-213, Astatine-211, Actinium-225, or Thorium-227. In one embodiment the Z, $S^2$ and R groups shown in Formula 1 are omitted, and a small molecule linker is used for linking radioactive metal isotopes to proteins, preferably antibodies. Thus the molecule (formula 1) has the general formula R—$S^1$—W in this case. Non-limiting examples of such molecules are shown below:

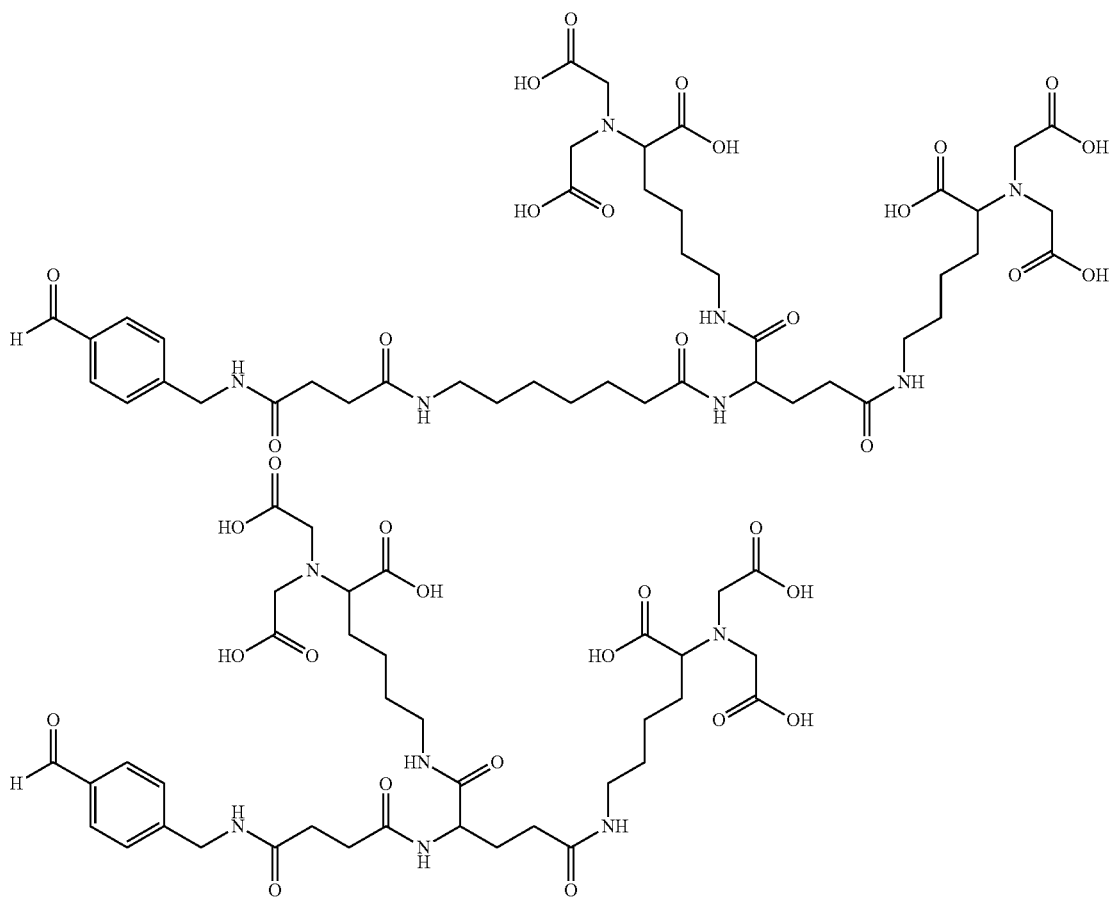

from the metal binding site or such as at most 2 nm from the metal binding site.

It is preferred that the reactive group E of the small molecule SMCoC of the general Formula 1 s conjugated to the protein within a radius of at most 1 nanometer from the metal binding site.

In one embodiment the small molecule SMCoC is conjugated to a cytotoxic agent. Said cytotoxic agent is in one embodiment selected from the group consisting of toxins, antibiotics, and nucleolytic enzymes. In one embodiment thereof, the cytotoxic agent is a toxin selected from the group consisting of doxorubicin derivatives, maytansinoids, auristatins, calicheamicins, CC-1065, duocarmycins and antracyclines.

In one embodiment the metal bound by the ligand(s) W and the histidines at said protein after conjugation to said In one embodiment said metal binding protein is conjugated to a cytotoxic agent via a linker that is cleavable under reducing, enzymatic or acidic conditions.

Uses

A further aspect of the present invention relates to uses of the metal binding protein conjugates of the present invention.

One embodiment relates to the use of metal binding protein conjugates obtainable by the method according to the first aspect of the present invention. In this case the protein conjugates contain an oligonucleotide conjugated to a metal binding protein and can be referred to as protein-oligonucleotide conjugates.

Another embodiment relates to the use of metal binding protein conjugates obtainable by the method according to the second aspect of the present invention. In this case the protein conjugates contain a small molecule conjugated to the metal binding site of an antibody and can be referred to as antibody-small molecule conjugates.

In one embodiment, the invention relates to the use of a metal binding protein conjugate, obtainable by the method according to the first aspect of the present invention, in immuno-PCR, targeted gene silencing, DNA-sensor technology or RNAi delivery.

Another embodiment of the present invention relates to the use of a metal binding protein conjugate in drug delivery. The metal binding protein conjugates obtainable by the methods according to the first and second aspect of the present invention comprise in one embodiment a functional compound that can be conjugated or attached to another compound such as for example a cytotoxic agent or a drug. These metal binding protein conjugates can be used in drug delivery. In one preferred embodiment thereof, the metal binding protein conjugate is an antibody conjugate. Thus, a particular embodiment of the present invention relates to use of antibody conjugates obtainable by the methods as described herein in drug-delivery and/or chemotherapy.

In one embodiment the protein conjugate, in particular an antibody conjugate, is used for chelation to metal radioisotopes. In one particular embodiment said protein-metal radioisotopes, preferably antibody conjugates, are used as a targeting contrast agent in positron emission topography imaging for diagnosis of disease, in particular for imaging of solid tumors. In another particular embodiment said protein-metal radioisotopes, preferably antibody conjugates, are used for treatment of disease, in particular for treatment of cancer by radiotherapy.

EXAMPLES

Experimental Methods

Reactions were monitored by thin-layer chromatography (TLC) analysis on Merck® silica gel 60 F254 TLC plates. All reagents were purchased from Sigma-Aldrich, except EDC.HCl (acquired from Iris Biotech), at the highest commercial quality and used without further purification. All solvents used were purchased as HPLC grade quality and used without further purification. NMR spectra were recorded on a Bruker Ascend™ 400 at 400 MHz ($^1$H NMR) and at 100 MHz ($^{13}$C NMR), and calibrated to the solvent residual peak. The following abbreviations were used for NMR data: s, singlet; d, doublet; t, triplet; m, multiplet. Coupling constant were rounded to nearest 0.5 Hz. All compounds synthesized were determined to be >95% pure by $^1$H NMR.

DNA was purchased from DNA Technology A/S (Risskov, Denmark), Sigma-Aldrich or Integrated DNA Technologies. The oligonucleotides synthesized by solid-phase oligonucleotides synthesis, were synthesized on a Mermade 12 RNA/DNA synthesizer with the final DMTr on. 1000 Å CPG was used as solid-support purchased from Bioautomation. The nucleosides dA, dC, dG and dT were purchased from Link technology. Modified DNA was purified on a RP-HPLC Hewlett Packard Agilent 1100 Series using Phenomenex Clarity 3 µm Oligo-RP 4.6×50 mm columns. All DNA concentrations and yields of ON reactions were determined using a ND-1000 NanoDrop® spectrophotometer. The water used was purified on a Milli-Q Biocell System. SDS-PAGE analysis was performed on precast NuPAGE® Novex 4-12% bis-tris gels according to manufactures protocol and stained with SimplyBlue™ SafeStain (Life Technologies™). Figure illustrations were generated using Visular Molecular Dynamics (VMD) (Humphrey, W., Dalke, A. & Schulten, K. VMD: visual molecular dynamics. J. Molec. Graphics 14, 33-38 (1996)). Electrospray ionization (ESI) mass spectrometry of intact proteins and protein conjugates was performed by Alphalyse A/S (Denmark).

Organic Synthesis

General procedure for the synthesis of linker molecules (compound 1 and 2) To a solution of the di-acid (suberic acid or 3,3'-dithiodipropionic acid) (500 mg, 2.4 mmol) in dry DCM (10 mL) was added EDC.HCl (1.37 g, 7.1 mmol) and N-hydroxysuccinimide (656.8 mg, 5.7 mmol). The mixture was stirred for 2 hours at rt. The organic phase was washed with a 2.5% aqueous solution of NaHSO4 (2×10 mL) and brine (10 mL), dried over anhydrous Na2SO4, filtered and concentrated in vacuo. No further purification was performed. Both compounds 1 and 2 were isolated as white solids with full conversion.

DSS Linker (Disuccinimidyl Suberate) (Compound 1)

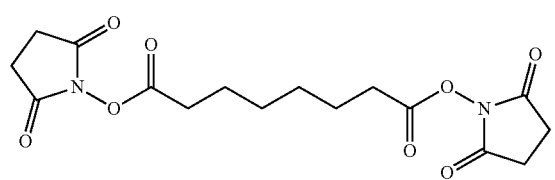 [SMILES: O=C(CCCCCCC(=O)ON1C(=O)CCC1=O)ON1C(=O)CCC1=O]

$^1$H NMR (400 MHz, CDCl$_3$) δ 2.82 (s, 8H), 2.60 (dt, J=2.5, 7.4 Hz, 4H), 1.80-1.71 (m, 4H), 1.48-1.42 (m, 4H). $^{13}$C NMR (100 MHz, CDCl$_3$) δ 169.3, 168.6, 30.9, 28.2, 25.7, 24.4.

DSP Linker (Dithiobis[Succinimidyl Propionate]) (Compound 2)

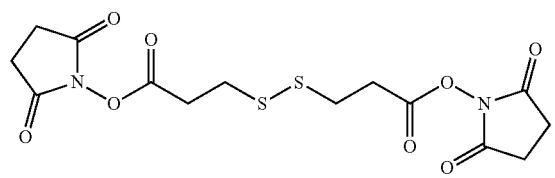 [SMILES: O=C(CCSSCCC(=O)ON1C(=O)CCC1=O)ON1C(=O)CCC1=O]

$^1$H NMR (400 MHz, DMSO-d6) δ 3.11 (t, J=3.0 Hz, 4H), 3.04 (t, J=3.0 Hz, 4H), 2.82 (s, 8H). $^{13}$C NMR (100 MHz, DMSO-d6) δ 170.0, 167.5, 31.9, 30.3, 25.4.

```
DNA sequences
3' amino-modified DNA:
                                  (SEQ ID NO: 1)
5' ACATACAGCCTCGCATGAGCCC-X 3'

5' trisamino-modified DNA:
                                  (SEQ ID NO: 2)
5' YYY-GGGCTCATGCGAGGCTTACGAAC 3'

3' Cy5-modified DNA:
                                  (SEQ ID NO: 3)
5' GGGCTCATGCGAGGCTGTATGT-Cy5 3'

3' fluorescein-modified DNA:
                                  (SEQ ID NO: 3)
5' GGGCTCATGCGAGGCTGTATGT-Flc 3'

3' amino- and 5' fluorescein-
modified DNA:
                                  (SEQ ID NO: 1)
5' Flc-ACATACAGCCTCGCATGAGCCC-X 3'

Tris(NTA) fully complementary DNA:
                                  (SEQ ID NO: 4)
5' GTTCGTAAGCCTCGCATGAGCCC 3'
```

X denotes an amine C7 modification and Y denotes the Unilink™ modification. Trisamine-DNA structure (Formula 11)

Formula 11

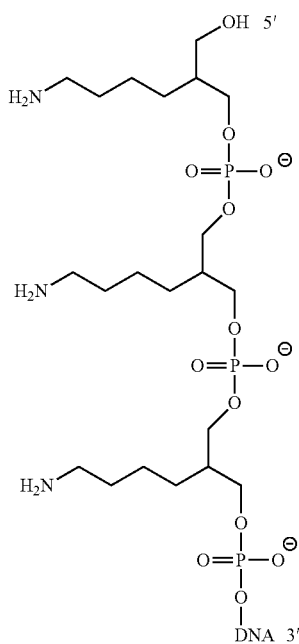

DNA Modification
Synthesis of Tris(NTA) Modified DNA (Guiding ON) (Formula 17)

The tris(NTA) was synthesized from trisamino-modified DNA. Briefly, the trisamino DNA (77.3 µM, 100 µL) was reacted with SPDP in DMF (100 mM, 25 µL) and TEA (0.75 µL) at rt for 1 hour. The solution was then diluted with HEPES (800 µL, 500 mM, pH 7.5) and excess reagents were removed using Amicon Ultra® centrifugal filters (MWCO 3000, 14100 g for 30 min). The retentate was collected and treated with TCEP (150 mM, in 500 µL 500 mM HEPES buffer, pH 7.5) for 15 min at rt. The excess reagents were removed using Amicon Ultra® centrifugal filters (MWCO 3000, 14100 g for 30 min). The retentate was washed twice with HEPES (50 mM, pH 7.5), before reaction with NTA-maleimide (Dojindo Molecular Technologies, 70 mM, in 10 µL 25 mM HEPES, pH 7.5) for 1 hour in a final volume of approx. 40 µL. The DNA was precipitated in an aqueous solution of NaOAc (3 M, 6 µL, pH 5.2), glycogen (20 mg/mL, 1 µL) and cold EtOH (96%, 100 µL) by incubation on dry ice for 15 min followed by centrifugation for 45 min (4° C., 20000 g). The supernatant was discarded and the pellet was allowed to dry, before dissolved in TEAA (195 µl, 0.1 M, pH 7.0). The desired product was collected from RP-HPLC and lyophilized. Rt=5.9 min (67%) MALDI-TOF MS: M; Calc.: 9262 found: 9260.

Formula 17

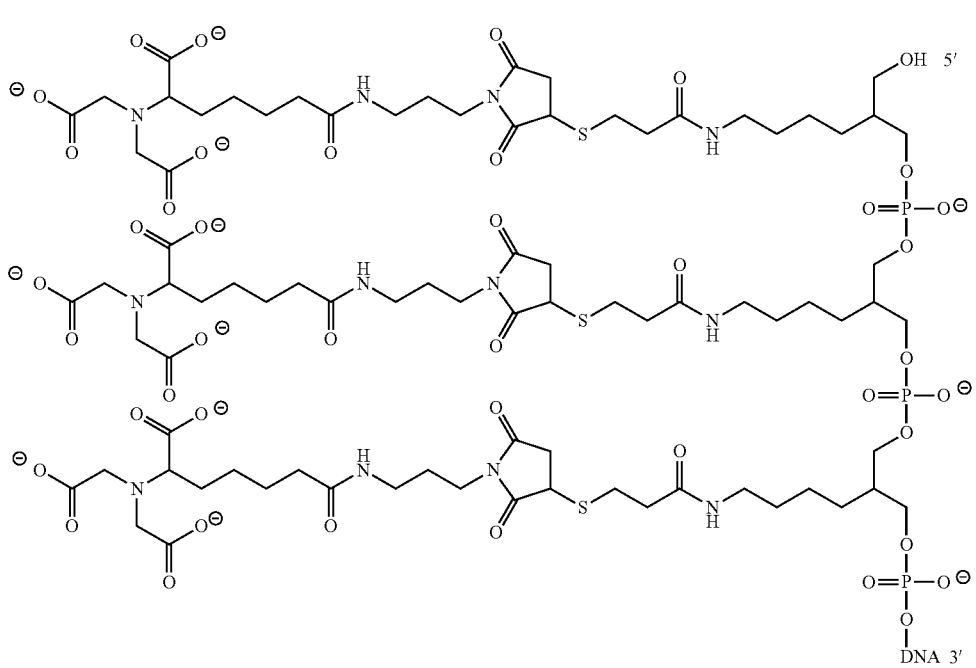

Conjugation of DSS/DSP (Compound1 and 2) Linker to Amino Modified DNA (3' NHS Ester DNA Modification) (Reacting ON) (Formula 18)

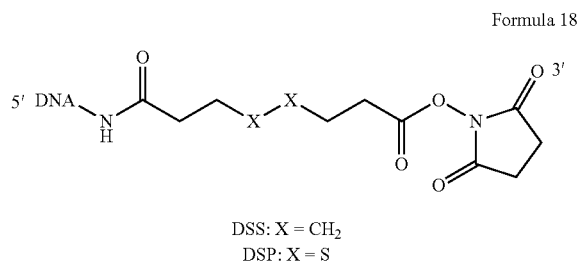

Formula 18

DSS: X = CH₂
DSP: X = S

To a solution of DNA (15 nmol) in water (75 µL) was added DSS/DSP linker in DMF (50 mM, 75 µL), MeCN (75 µL), and TEA (1 µL). The mixture was shaken for 30 min at rt. The DNA was precipitated in an aqueous solution of NaOAc (3 M, 28 µL, pH=5.2), cold EtOH (565 µL), and glycogen (20 mg/mL, 1 µL) by incubation on dry ice for 15 min followed by centrifugation for 1 h (4° C., 20000 g). Immediately hereafter, the supernatant was removed, and the pellet was dissolved in 195 µL TEAA buffer (0.1 M) and purified by RP-HPLC 10-20% MeCN in 0.1 M TEAA over 15 min. Flow=1 mL/min. T=25° C. The product-containing fractions were collected and added to an equivalent amount of a 2% aqueous solution of TFA (resulting in a 1% final TFA concentration to significantly lower the rate of NHS ester hydrolysis). The DNA was distributed equally over 10-20 Eppendorf® tubes (aiming at approx. 200-600 pmol in each tube) and lyophilized. The exact amount in each tube was determined on RP-HPLC by comparison to a known amount of the starting amino-modified DNA, assuming that the conjugation did not affect the extinction coefficient at 260 nm. The degree of NHS-ester hydrolysis observed on RP-HPLC was typically found to be <5% for the DSS linker and 10-20% for the DSP linker, probably due to an inductive effect of the disulfide linkage.

DSS: Rt=11.1 min (36%) MALDI-TOF MS: M; Calc.: 7115 found: 7113.

DSP: Rt=11.2 min (32%) MALDI-TOF MS: M; Calc.: 7151; found: 7163.

DNA-Protein Conjugation Reactions

Nearly identical experimental conditions were used for conjugation reactions to his6-tagged proteins, serotransferrin (Tf), and antibodies. All proteins and antibodies were used without further purification (purchased from Sigma-Aldrich or US Biological). Protein aliquots were made in PBS buffer (0.01 M Na2HPO4, 0.14 M NaCl, pH=7.5, 20% glycerol, 0.02% Tween®-20 detergent) using DNA LoBind Eppendorf® tubes (0.5 mL) to minimize surface adhesion. All antibodies were used directly as purchased. Reactions were carried out in LoBind Eppendorf® (0.2 mL, 0.5 mL or 2 mL) tubes with a final Tween®-20 concentration of 0.02%.

Preparation of the Reacting ON (Neutralization of 3' NHS Ester Functionalized Oligo)

Due to the competing hydrolysis of the NHS ester functionality the Reacting ON was prepared (neutralized) immediately before use.

The 3' NHS ester modified DNA strand (containing either DSS or DSP linker) was dissolved in MES buffer (500 mM, 1 µL, pH=6.0) and water to approximately half the volume required to make a final DNA concentration of 4 µM. The pH of the mixture was adjusted to 5.8-6.0 by adding an aqueous TEA solution (100 mM) and water to reach a final DNA concentration of 4 µM.

DNA templated conjugation reactions on his6-tagged proteins and metalloproteins Reactions were performed by mixing Guiding ON (0.25 µM) with the protein of interest (0.25 µM), NiCl2 (0.75 µM), and Reacting ON (0.25 µM) in EPPS buffer (50 mM, pH 7.7) containing NaCl (400 mM) and Tween®-20 (0.02 v/v %). The mixture was left to react overnight at rt before being analyzed/purified by PAGE. The scale has been varied from 20 µL to 10 ml. Larger reaction volumes were concentrated using Amicon Ultra® centrifugal filters (MWCO 3000, 14100 g for 30 min) and washed with water before PAGE (6%) analysis/purification. Note that for DTPC on Tf a freshly prepared solution was made (Tf dissolved in 1×PBS buffer containing Tween®-20) before each series of experiments. Therefore, minor variations in actual concentration cannot be excluded.

DNA Templated Conjugation on Metal-Dependent Enzymes

Reactions were performed in similar conditions as for conjugation on his6-tagged proteins and Tf, though with the exception of using 3 eq. Cu(NO3)2 instead of NiCl2. All reactions were mixed at rt and then left overnight at 4° C. The conjugation products were purified and isolated from PAGE (4%).

Conjugation Reactions on Monoclonal IgG1 Antibodies (Mouse)

DNA conjugation was performed on anti-c-Myc, anti-FLAG® M2, anti-EGFR and anti-β-tubulin. A similar protocol as for conjugation to his6-tagged proteins was used for antibodies except applying one equivalent of $Cu(NO_3)_2$ instead of three equivalents $NiCl_2$. Additionally, 600 mM NaCl was used instead of 400 mM to prevent non-templated reaction. In the case of conjugating to anti-c-Myc, anti-EGFR and anti-β-tubulin 1.4 equivalents (0.35 µM) of protein was used compared to DNA (relying on the concentration given by supplier). For conjugation to anti-FLAG® M2 one equivalent (0.25 µM) was used to avoid non-templated coupling. An increased amount of DNA resulted in faster migrating bands corresponding to more than one DNA strand on the same antibody. The DNA-antibody conjugates were analyzed and purified using 4% native PAGE. Reactions were performed on 20 µL-4 mL scales.

ON Toehold Replacement of Conjugation Products

After overnight conjugation reaction EDTA (2.5 mM) and an ON complementary to the full sequence of the Guiding ON (2 eq.) was added and left to displace the Reacting ON at room temperature for 30 min before spin filtration of the reaction mixture (3K filters) followed by PAGE purification. This resulted in pure conjugates containing a single stranded ON.

Purification/Isolation of Conjugation Product

Conversion denotes direct in-gel determination of product formation from the crude reaction mixture, whereas yield denotes the purified/isolated amount of single-ON conjugated protein product obtained from gel-extraction.

Gel-Extraction (Yields)

For larger amounts the gel was visualized with SYBR® Gold and imaged on a Safe Imager 2.0. After toehold mediated ON replacement (see above) the product-containing bands were cut from the gel using a scalpel and extracted by passive diffusion in EPPS buffer overnight (1.5-2 ml, 50 mM EPPS, 200 mM NaCl, 0.02% *Tween®-20, pH 7.7). The samples were concentrated using 3K spin filters before analysis by 4% or 6% PAGE. The yields (or conversions) were determined by comparing in-gel SYBR® Gold absorbance of the DNA-protein conjugate to a series of internal DNA standards (0.5-2 pmol of 3' amino-modified DNA strand) using the software ImageQuant. Since the conjugates only contain a single ON (and single stranded) direct comparison to the internal DNA standard is possible. The yields hereby note the percentage of purified/isolated single-ON conjugate compared to the amount of added Reacting ON (1:1 with protein).

N.B. For mass spectrometry samples no detergent was used for extraction.

For purification of enzyme-DNA and DNA-mAb conjugates gel-extraction was performed overnight at 4° C. In the case of gel-extraction of CPB conjugate no detergent was used.

Conjugation Reactions on Fc and F(Ab')2 Fragments (Mouse)

Fc and F(ab')2 fragments were purchased from Jackson ImmunoResearch Laboratories Inc. Conjugation reactions were similar to the procedure for antibodies, with the exception of performing 2× buffer exchange using Illustra™ MicroSpin G-25 columns (GE Healthcare Life Sciences) to end up in PBS buffer (1×) prior to reaction.

Proteins and Metal Ions

When considering metal-binding proteins several distinctions are worth considering. A large subset of all proteins requires the association of very specific metal ions to be functional, examples include iron-dependent oxygenases both heme and non-heme associated, serotransferrin, zinc proteases and so forth. Based on the presented experimental results, it is expected that our method will allow site-selective ON-labeling to a very large number of these. Metal ions situated in e.g. porphyrin structures will not allow coordination to our directing NTA moiety and therefore is beyond the scope of our method.

A considerable subset of all proteins is capable of associating with metal ions, not because it is required for them to function but simply because amino acids on the protein surface comprise an inherent affinity for Lewis acids. This has been known for decades and has been widely used for immobilized metal affinity chromatography (IMAC). Not only for proteins purposely engineered with polyhistidine termini, but also for native (wild-type) proteins such as antibodies. Proteins that are post-translationally phosphorylated can frequently be enriched on titanium dioxide resin or IMAC columns and we therefore foresee that our method could be adapted in labeling these as well.

Tf Receptor Binding Experiments

DNA-Tf conjugate was first saturated with Fe(III) (3 hrs with 10 fold molar excess FeCl3 in 100 mM NaHCO3). For the receptor binding experiments, 100 fmol DNA-Tf conjugate was incubated at 37° C. for 30 minutes with or without purified Tf receptor (Sino Biological, Catalog #11020-H07H) in a total volume of 10 µl binding buffer (100 mM NaHCO3, pH 7.8). Complex formation was monitored using non-denaturing PAGE (6%, Tris-borate). Nucleic acids were stained with SYBR® Gold, visualized using a typhoon scanner and analyzed with ImageQuant software. The amount of unbound DNA-Tf conjugate was plotted as a function of the Tf receptor added.

Reduction of DNA-Antibody Conjugates

The purified anti-β-tubulin conjugates in EPPS buffer (50 mM EPPS, 200 mM NaCl, 0.02% Tween®-20, pH 7.7) were incubated with DTT (10 mM) and LDS sample buffer (4×, NuPAGE® Life Technologies) at 90° C. for 5 min. The resulting protein fragments were analyzed with SDS-PAGE (4-12%) and visualized by either Coomassie staining or fluorescence scanning (Cy5 or fluorescein).

Western Blotting Using Anti-FLAG® Conjugate Produced by DTPC

Different amounts of (FLAG)3-Hfq (0.2-3.0 pmol) were mixed with a sample of total proteins isolated from *E. coli* and loaded on a SDS gel (12%). Proteins were subsequently transferred to an Immobilon P PVDF membrane by semi-dry blotting. The blot was incubated for 2 hrs with the anti-FLAG® conjugate in Tween-TBS. After washing the blot, the bound anti-FLAG® conjugate was visualized by adding a 3' fluorescein labeled antisense ON. The blot was then probed with HRP-conjugated anti-mouse secondary antibody and visualized by chemiluminescence (Pierce ECL Plus substrate).

Gel Analysis

SDS-PAGE Gel Analysis

For SDS-PAGE analysis was used 1.00 mm thick 4-12% NuPAGE® Bis-Tris Precast Gels (Novex® by Life Technologies). As running buffer was used 50 mM MES, 50 mM Tris Base, 0.1% SDS, 1 mM EDTA, pH 7.3. Samples were heated at 90° C. for 5 min in NuPAGE® LDS Sample Buffer (Novex® by Life Technologies) before loading. The gels were run at 200 V for 35 min at 4° C. The protein bands were visualized using SimplyBlue™ SafeStain (Life Technologies).

General for PAGE Analysis

All conjugation reactions were analyzed by PAGE using 17 cm×15.5 cm×1 mm size gels (=40 mL). For PAGE analysis/purification of his6-tagged proteins and Tf, all gels used were 6% acrylamide/bis-acrylamide and run in tricine buffer (50 mM, pH=8.1), whereas 4% gels were used for antibody analysis/purification. DNA visualization was performed by staining with SYBR® Gold in water. Gel bands were processed using a Typhoon scanner (Trio Scanner, GE Healthcare). SYBR® Gold stained nucleic acids were visualized by blue light irradiation (excitation=488 nm) using a 555 nm emission filter while GFP fluorescence was visualized at 488 nm excitation with a 520 nm emission filter.

Denaturing PAGE

After overnight incubation the samples were lyophilized to dryness. The solids were then dissolved in an aqueous EDTA solution (2 mM, 8 µL) and urea loading buffer (10 M, 12 µL) containing Orange G to have a visible reference band during gel running. The mixture was heated to 65° C. for 3 min to assure complete denaturing conditions. The gel was pre-run for 20 min before loading the samples to ensure an equal heat distribution. The gel was then run at 20 watts for 1.5 hours.

Denaturing X % Gel Recipe (to Make 40 mL)

A suspension of urea (16.8 g) in tricine buffer (500 mM, pH=8.1, 4 mL) and formamide (10 mL) was gently heated in microwave to fully dissolve the urea. Then acrylamide/bis-acrylamide (40%, X mL) and APS (10 wt %, 400 µL) was added followed by the immediate addition of water to make a total volume of 40 mL. Finally, TEMED (40 µL) was added and the solution was gently shaken to make a homogenous mixture ready for use.

Non-Denaturing PAGE

After overnight incubation sucrose loading buffer (6×, 8 µL) containing Orange G was added to the sample mixture. The samples were then loaded directly onto the gels, which were then run at 4 watts for 3 hours and 15 min (GFP and Tf, 6% PAGE) or for 2 hours and 15 min (antibodies, 4% PAGE).

Non-Denaturing X % Gel Recipe (to Make 40 mL)

Made according to the procedure for denaturing gels but without the addition of urea and formamide and without heating.

MS/MS Analysis of DNA-Protein Conjugates

Sample Preparation of DNA-Protein Conjugates Prior to MS/MS Analysis

After conjugation reaction the mixtures were concentrated using YM-3 filters. Conjugation products were purified by cutting out the relevant bands from non-denaturing PAGE following the conditions described in the above. The gel piece containing the labeled protein was incubated for 16 hours in 50 mM ammonium bicarbonate with 5 mM DTT. The extracted protein conjugate was lyophilized and dissolved in 6 M urea, 50 mM ammonium bicarbonate and 5 mM DTT and incubated for 1 hour before iodoaceteamide was added to a final concentration of 30 mM. After additional 1 hour of incubation the sample was diluted 4 times and treated with sequence graded trypsin (Sigma-Aldrich) (1:20) for 16 hours at 37° C. The tryptic peptides were micro-purified on C18 StageTips (Thermo Scientific) according to the manufacturer's protocol. The micro-purified peptides were analyzed by LC-MS/MS.

General Procedure for MS/MS Studies nLC-MS/MS analyses were performed on an EASY-nLC II system (Thermo Scientific) connected to a TripleTOF 5600+ mass spectrometer (AB Sciex) equipped with a NanoSpray III source (AB Sciex) operated under Analyst TF 1.5.1 control. The lyophilized samples were suspended in 0.1% formic acid, injected, trapped and desalted isocratically on a Biosphere C18 column (5 µm, 2 cm×100 µm I.D; Nano Separations). Peptides were eluted from the trap column and separated on a self-packed 15-cm analytical column (75 µm i.d.) with RP ReproSil-Pur C18-AQ 3 µm resin in a pulled emitter (Dr. Marisch GmbH, Ammerbuch-Entringen, Germany). Peptides were eluted using 250 nl/min and a 30 min gradient from 5% to 35% phase B (0.1% formic acid and 90% acetonitrile). The collected MS files were converted to Mascot generic format (MGF) using the AB SCIEX MS Data Converter beta 1.1 (AB SCIEX) and the "proteinpilot MGF" parameters. The generated peak lists were searched against an in house database using the Mascot search engine (matrix science). Search parameters were trypsin and allowing 3 missed cleavage sites. Carbamidomethyl was set as fixed modification of cysteine and the alkylated modification added by the chemical labeling was set as a variable modification on Lys residues. Peptide tolerance and MS/MS tolerance were set to 10 ppm and 0.2 Da respectively.

Cell Culture

KB-3-1 cells (ATCC) were maintained in full RPMI-1640 Glutamax medium (Gibco) and U-87 MG cells (ATCC) were maintained in DMEM, low glucose (1 g/L) (Gibco), both supplemented with 10% fetal bovine serum, penicillin (100 U/mL) and streptomycin (50 ug/mL), at 37° C. in humidified air containing 5% CO2.

Tf Uptake Experiments

In a typical experiment 40.000 KB cells/well were seeded in 8-well chamber slides (Sarstedt) and grown overnight in FBS containing RPMI-1640 medium. On the next day the medium was exchanged by washing the cells twice with FBS-free RPM 1-1640 medium, followed by incubation in FBS-free medium for additional 6 hours.

To assess Tf-conjugate uptake using microscopy and flow cytometry a Cy5-labeled ON was hybridized to the DNA-Tf conjugate. The cells were incubated at 37° C. with iron-saturated DNA-Cy5-Tf conjugates at a final concentration of 50 nM. After 15 min incubation, the cells were washed three times with ice-cold PBS to terminate uptake and to remove excess conjugate. To assess the specificity of Cy5-DNA-Tf conjugate uptake, competitive binding assays were performed by pre-treating the cells with 500 nM native holo-Tf 5 min before addition of iron-saturated DNA-Cy5-Tf conjugates. For microscopy the membranes were stained in 5 µg/ml Alexa Fluor® 488 conjugate of WGA (Invitrogen) for 10 min at room temperature. Cells were fixed by incubation with 4% PFA in PBS for 15 min at room temperature followed by three PBS washes. Following fixation the cell slide was dried under a stream of nitrogen and mounted using ProLong Gold antifade reagent. The mounting media was allowed to settle for 24 h before microscopy.

Immunofluorescence Experiments

In a typical experiment 40.000 U-87 MG cells/well were seeded in 8-well chamber slides (Sarstedt) and grown overnight in FBS containing DMEM with low glucose. On the next day the cells were fixed by incubation with 4% PFA in PBS for 15 min and subject to blocking and permeabilization by 1 h incubation with 5% horse serum and 0.3% Triton-X in PBS at room temperature.

The purified anti-β-tubulin-ON conjugate was hybridized to a Cy5-labeled ON before diluted with PBS containing 0.1 Triton-X and 1% BSA to a final concentration of ~3 nM. The antibody-Cy5 conjugate was added to the fixed cells and incubated for 1 h at room temperature in the dark. After incubation the cells were washed 3 times with PBS, dried in a stream of nitrogen and mounted using ProLong Gold antifade reagent. The mounting media was allowed to settle for 24 h before microscopy.

Microscopy

Microscopy was performed on a confocal laser scanning microscope (LSM 700; Zeiss, Jena, Germany) equipped with 4 solid state lasers delivering light at 405, 488, 543, and 633 nm, respectively. Light was collected through 40 1.3 DIC M27 and 63×1.4 DIC M27 oil immersion objectives (Zeiss). DAPI fluorescence was excited with the 405 nm line, while Cy5 fluorescence was excited using a 639 nm line. Digital image recording and image analysis was performed with the ZEN 2011 software, version 7.0.7.0 (Zeiss).

Flow Cytometry

Flow cytometric analysis was performed on a Gallios Flow Cytometer (Beckman Coulter) using the 638 nm laser. FCS files were analyzed using Kaluza.

Example 1

Conjugation of an Oligonucleotide Comprising an NHS Group to Green Fluorescent Protein Comprising an N-Terminal his6-Tag As a model system, the interaction between a recombinant green fluorescent protein (GFP) comprising an N-terminal his6-tag and a Guiding ON (second oligonucleotide modified with a tris(NTA) moiety (FIG. 2) was selected, such that the Guiding ON functions as a guiding oligonucleotide. In the presence of nickel(II) ions, the binding of the tris(NTA) unit to the his6-tag has a dissociation constant in the low nanomolar range (Goodman, R. P. et al. A facile method for reversibly linking a recombinant protein to DNA. ChemBioChem 10, 1551-1557 (2009)). Upon addition of a complementary oligonucleotide (the first oligonucleotide) modified with an activated N-hydroxysuccinimide (NHS) ester (reacting group) a complex was be formed, bringing the activated ester into close proximity with lysines near the his6-tag. The complex facilitated a successful reaction in spite of the low global concentration (nM), making a limited number of sites significantly more likely to react than the rest.

The Reacting ON (first oligonucleotide), carrying an NHS ester, was prepared by reacting an amino-modified oligonucleotide with disuccinimidyl suberate (DSS). After ethanol precipitation and RP-HPLC purification aliquots were lyophilized in TFA and stored at −20° C. with minimal hydrolysis (less than 5%) following the procedure by Snyder et al. (24). The Guiding ON was synthesized according to the procedure described by Goodman et al. (23) and added to his6-tagged GFP in a buffered solution (EPPS pH 7.7) containing nickel(II) chloride. A surfactant was added to minimize protein adhesion. Finally, the first oligonucleotide was added in equimolar amount after neutralization of the residual TFA. To investigate the rate of product formation, a standard conjugation reaction of DNA to his6-tagged GFP and serotransferrin was prepared on a 0.5 ml scale. Aliquots were removed, quenched with EDTA (5 mM final conc.) and urea (5 M final conc.) and stored at −20° C. until PAGE analysis. The normalized product formation as a function of time is presented below. The analysis indicates that at least 3 hours of reaction time was required to ensure optimal conversion (FIG. 3). The ester hydrolysis rate in the reaction buffer is shown in FIG. 4. A solution of the NHS ON (5 µM) in the reaction buffer was prepared and left at room temperature for 48 hours. At selected time-points aliquots were removed, mixed with TEAA (100 mM final conc.) and analyzed using RP-HPLC (10-20% MeCN in 0.1 M TEAA over 15 min. Flow=1 mL/min. T=25° C.). (FIG. 4). The ideal pH-range for the reaction was 7.7-8.3 (data not shown).

To avoid non-templated reaction between the first oligonucleotide and random lysines on the surface of GFP, concentration of the macromolecules was a key parameter. Furthermore, it was observed that increasing solvent salinity reduced unspecific (non-templated) labeling (FIG. 5), probably by diminishing unwanted electrostatic interactions between cationic protein surface patches and the anionic DNA. By tuning pH, concentration, and salinity it was possible to avoid non-templated reaction and obtain 38% isolated yield of the template-directed single-oligonucleotide conjugation product after gel-extraction (61% conversion) (yields and conversion are determined based on DNA). Conversely, by analyzing the conjugation reaction based on GFP fluorescence under non-denaturing conditions it was observed that essentially all GFP has reacted to form the DNA-protein conjugate (FIG. 6). To ensure the generality of the procedure, we successfully tested the protocol on several other proteins such as interleukin-6, endoglycosidase H, plasminogen activator inhibitor-1, and glutathione S-transferase carrying either N- or C-terminal his6-tags (FIG. 7).

Example 2

Conjugation of an Oligonucleotide Comprising an NHS Group to Serotransferrin

Recombinant proteins are often expressed with a terminal histidine tag to facilitate affinity purification and are thereby artificially modified to coordinate metals. However, a large proportion of naturally occurring proteins have inherent metal binding sites, either in the form of a well-defined catalytic active site or as a surface patch that favor certain metal coordination—e.g. through a histidine cluster. This allows extension of the DNA templated protein conjugation (DTPC) method beyond recombinant his-tagged proteins. Metalloproteins are involved in enzymatic processes and signaling as well as cellular transport and have been estimated to constitute approximately one third of all proteins found in nature (Waldron, K. J., Rutherford, J. C., Ford, D. & Robinson, N. J. Metalloproteins and metal sensing. Nature 460, 823-830 (2009)). We hypothesized that the Guiding ON carrying tris(NTA) as a ligand would facilitate a sufficiently strong interaction to enable template-directed labeling in the proximity of the metal binding site of a metal binding protein. To investigate this we used serotransferrin (Tf), a protein responsible for the regulation and transport of iron(III) across cell membranes (Aisen, P. & Listowsky, I. Iron transport and storage proteins. Annu. Rev. Biochem. 49, 357-393 (1980)) (FIG. 8a). When exposing the Tf apoprotein to the Guiding ON carrying a tris(NTA) moiety and subsequently to the Reacting ON in the presence of $NiCl_2$ a single-band conjugation product was observed by PAGE (FIG. 9). This conjugation product could be isolated in 13% yield after gel extraction (53% conversion).

Example 3

Site-Selectivity of the Method

Figure 12:
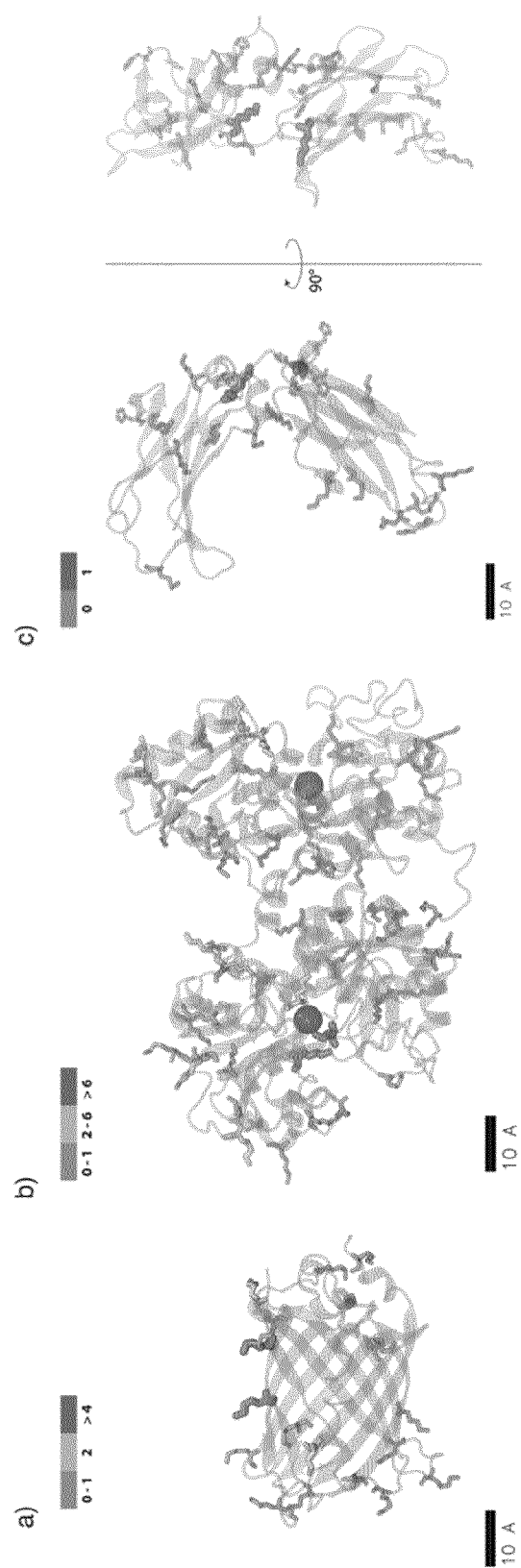

An important characteristic of the presented method is the potential site-selectivity of the labeling. The ability to produce a conjugation product exclusively when the complementary templating strand and metal ions are present strongly suggests that a certain site-selectivity can be expected (FIG. 10). Mass spectrometry analysis of purified GFP-DNA and Tf-DNA conjugates shows that only a single oligonucleotide is conjugated (FIG. 11). To evaluate which amino acids are preferentially labeled the isolated DNA-protein conjugate was analyzed by tandem mass spectrometry (MS/MS). A DSP linker containing a disulfide bond was employed (see "Experimental methods" section). This allowed removal of the oligonucleotide prior to mass spectrometry, thereby simplifying the analysis. Briefly, the disulfides in the gel-purified conjugate, both internal and between the protein and Reacting ON, were reduced and alkylated prior to tryptic digestion. This procedure leaves a distinct fragment attached to lysines previously modified with an oligonucleotide. The mass spectrometry analysis revealed oligonucleotide attachment to a limited number of lysines located in a cluster in the vicinity of the metal binding sites (FIG. 12). However, this procedure does not provide a quantitative distribution, and due to the high sensitivity of the MS/MS technique even negligible amounts of a certain product may be observed. In order to obtain an estimate of the relative product distribution conjugation products from several (>6) individual experiments were analyzed and compared using MS/MS. Both in the case of GFP and Tf this showed predominant conjugation to two closely positioned lysines (FIG. 12).

Example 4

Protein Function is not Impaired by DTPC

To assess if the protein function is impaired by the DNA conjugation, toehold-mediated strand displacement was employed to remove the Guiding ON after covalent attachment of the first oligonucleotide. This resulted in Tf covalently attached to a 22-basepair DNA duplex labeled with a Cy5 fluorophore. Electrophoretic mobility shift assays of the DNA conjugate showed a nanomolar affinity towards the Tf receptor (FIG. 8b and FIG. 13). To investigate if this retained receptor affinity would also permit cell uptake, human KB cells, a subline of the ubiquitous KERATIN-forming tumor cell line HeLa, were incubated with the DNA-Cy5-Tf conjugate. This showed that the conjugate was indeed transported to the cell interior, and as demonstrated by a competition experiment with a large excess of free native Tf, the transport is actively mediated by the Tf receptor (FIG. 8c and FIG. 14).

Example 5

Conjugation of Oligonucleotides to Alkaline Phosphatase (AP) and Carboxypeptidase B To validate the generality of the method on wild-type metal-binding proteins templated single-oligonucleotide labeling of two metal-dependent enzymes was demonstrated; alkaline phosphatase (AP) and carboxypeptidase B (CPB) (FIG. 15 and FIG. 16). The activity of purified carboxypeptidase B (CPB)-DNA conjugate was compared to the wild-type CPB enzyme using a spectrophotometric assay. In brief, CPB or CPB-DNA conjugate (74 nM) was added to Hippuryl-L-Arginine (1 mM) in Tris-HCl buffer (25 mM) with NaCl (100 mM) at pH 7.65. Absorption at 260-10 nm was measured every minute at 25° C. on a FLUOstar OPTIMA (BMG Labtech) using a UV transparent plate. The reaction mixture without enzyme was used as blank (FIG. 17). The activity of purified alkaline phosphatase (AP)-DNA conjugate was compared to the wild-type AP enzyme using a spectrophotometric assay. In brief, Alkaline phosphatase or Alkaline phosphatase-ON conjugate (15 nM) was added to para-nitrophenylphosphate (10 mM) in 1× FastAP buffer (Fermentas) at 25° C. to initiate substrate conversion. Once every 60 s, 50 µl of the reaction was quenched in 100 µl 1M KOH. After 15 min the 390 nm absorption was measured for all samples on a FLUOstar OPTIMA (BMG Labtech). The reaction mixture without enzyme was used as blank (FIG. 18). Both enzymes proved to be catalytically functional after oligonucleotide conjugation and gel-purification (FIG. 17 and FIG. 18).

Example 6

Conjugation of Oligonucleotides to Antibodies

DNA-antibody conjugates are essential to immuno-PCR (7) and are also becoming increasingly important in DNA nanotechnology. When integrated in DNA nanovehicles DNA-antibody conjugates have been used to induce apoptosis (Douglas, S. M., Bachelet, I. & Church, G. M. A logic-gated nanorobot for targeted transport of molecular payloads. Science 335, 831-834 (2012)) and there is a great potential for employing antibodies as recognition and functional elements in smart DNA nanodevices. Very recently Yin and coworkers demonstrated the use of DNA-antibody conjugates for 3D super-resolution imaging in cells (Jungmann, R. et al. Multiplexed 3D cellular super-resolution imaging with DNA-PAINT and Exchange-PAINT. (Jungmann, R. et al. Multiplexed 3D cellular super-resolution imaging with DNA-PAINT. Nature Methods 11, 313-318 (2014).

From a screening perspective it would be highly desirable to develop a general and simple conjugation method applicable to commercially available antibodies. The histidine-rich cluster located in the metal-binding region of the constant Fc domain of the antibody is shown in FIGS. 19a and 19b. BLAST alignment between human IgG1 mouse IgG1 and rabbit IgG shows primary sequence conservation of histidines and the crystal structures of their Fc domains confirm their spatial proximity (FIGS. 19a and 19b).

When similar conditions applied for labeling of his6-GFP and Tf (3 eq. $NiCl_2$ but 600 mM NaCl were used for labeling murine monoclonal antibodies (mAbs)), including anti-c-Myc, anti-FLAG®, anti-EGFR and anti-β-tubulin, a single very weak band with low mobility was observed by PAGE analysis (FIG. 20). When increasing the reaction concentration, yields of DNA-antibody conjugates were improved, but it also resulted in non-templated coupling (data not shown). However, metal-complexes containing copper(II) are generally more stable than nickel(II). Incubating the mAb, Reacting ON and Guiding ON with 3 equivalents of a copper(II) dramatically increased the yield of DNA-antibody conjugates, while non-templated coupling was still avoided (FIG. 20). However, several distinct migrating product bands were observed, which could be ascribed to more than one oligonucleotide attached to the same mAb (FIG. 21 and FIG. 23). Since IMAC using immobilized copper(II) ions commonly give rise to more unspecific protein interactions the reaction conditions could be further optimized to favor single oligonucleotide attachment by decreasing the copper(II) concentration to 1 equivalent compared to DNA while using a NaCl concentration of 600 mM (FIG. 20 and FIG. 22). Thereby, the desired single-oligonucleotide conjugates in approximately 10% after purification by gel-extraction was obtained. To characterize the DNA attachment sites, the anti-β-tubulin conjugate was fragmented into heavy and light chains by reduction and analyzed by SDS-PAGE (FIG. 19d). A slower migrating band was observed for the heavy chain conjugate (FIG. 19d, lane 4), whereas no additional bands from the light chain conjugates were observed. However, Coomassie-staining of proteins was approximately 32% less efficient when a single DNA strand was attached compared to a non-labelled protein (FIG. 24), and the relative band intensities are therefore not comparable. In order to obtain the relative distribution between heavy versus light chain labelling, a 5' fluorescein-labelled Reacting ON was used, revealing a significant selectivity towards heavy chain conjugation (FIG. 19d right). A similar experiment was performed on anti-c-Myc showing the same selectivity (FIG. 25).

To further determine whether conjugation was directed towards the constant Fc domain or the variable F(ab')$_2$ domain, both of the individual protein fragments were acquired (IgG mouse), and subjected to the reaction conditions using a 5' fluorescein functionalized Reacting ON (FIG. 19e and FIG. 26). When performing the reaction on the Fc domain, DNA-antibody conjugate product was exclusively observed when templating strand was present (FIG. 19e lanes 1-2), as demonstrated for the other metal-binding proteins (his6-tagged proteins, Tf and mAbs). However, when performing the reaction on the F(ab')$_2$ domain only, more unspecific conjugation was observed due to the approximately two times larger protein size, and only a slight increase in product formation was obtained when the templating strand was present (FIG. 19e lanes 3-4). Even more importantly, when both domains were present in equimolar amounts, a certain amount of unspecific conjugation was still observed on the F(ab')$_2$ domain, whereas the templated reaction almost exclusively was directed to the Fc domain (FIG. 19e lanes 5-6). Notably, this selectivity is achieved in spite of the approximate 2:1 excess number of lysines on F(ab')$_2$ compared to the Fc domain.

Additionally, the purified anti-β-tubulin conjugate was subjected to mass spectrometry as previously described for the his6-tagged GFP and Tf conjugates. This confirmed the labelling to be site-selectively directed towards the histidine cluster of the conserved Fc domain (FIG. 12).

The preservation of function of the anti-FLAG® conjugate was confirmed both by standard Western blotting with a secondary antibody containing horseradish peroxidase reporter enzyme and by using the conjugate directly as a primary fluorescent antibody when assembled with a fluorescein-labeled complementary ON (FIG. 27). Retained function of the anti-β-tubulin conjugate was confirmed by hybridizing the conjugate to a Cy5-modified complementary ON, which was successfully employed in immunofluorescence studies of microtubules in fixed U-87 MG cells (FIG. 19c and FIG. 27).

Discussion

The above examples have demonstrated that his6-tagged proteins and wild-type metal-binding proteins can be site-selectively labelled with DNA by DTPC. In particular, it was shown that monoclonal antibodies are mainly labelled on the constant Fc domain, making DTPC a universal method to site-selectively conjugate IgG1 antibodies. Further, it was shown that the labelled proteins had retained function after DNA conjugation.

The oligonucleotides required for the method are accessible by chemical conversions of synthetic ONs. While the tris(NTA) motif enables conjugation to such different proteins as Tf and IgG1, the potential of DTPC lies in its modularity. Using this method it becomes significantly more rapid and considerably simpler to obtain a series of different proteins functionalized with a single ON.

As a consequence of an increased requirement for iron in rapid cell division several types of cancer cells have an elevated expression of Tf receptors (Gatter, K. C., Brown, G., Trowbridge, I. S., Woolston, R. E. & Mason, D. Y. Transferrin receptors in human tissues: their distribution and possible clinical relevance. J. Clin. Pathol. 36, 539-545 (1983).). In example 4 it was shown that the DNA-Tf conjugates produced by DTPC are transported into cells via receptor-mediated endocytosis, and the presented method thereby holds the potential to be applied in targeted gene silencing by simplifying the construction of new conjugates. Furthermore, DTPC can allow identification of uncharacterized natural metalloproteins by using the covalent DNA tag as a method for protein enrichment.

Due to the unique ability of antibodies to bind its specific antigen with high affinity antibody-drug conjugates are of tremendous interest in health sciences.

Example 7

DNA-Templated Reductive Amination Using Aldehyde-Functionalized Reacting ON

A reacting oligonucleotide conjugated to an aldehyde was created and conjugated to a metal binding protein (see FIG. 28). The aldehyde-DNA conjugate was created by synthesizing a NHS-ester product (see scheme 2) that was subsequently conjugated to an amino-modified DNA strand (see compound 3).

FIG. 28 shows DNA-templated protein conjugation using reductive amination. The Guiding ON modified with tris (NTA) coordinates the metal-binding protein through an interaction with metal ions. The partly complementary Reacting aldehyde ON reacts with nearby lysine residues in the presence of a reducing agent like NaCNBH$_3$.

Synthesis

4-Formylbenzoic Acid NHS

The NHS-ester product was synthesized by mixing 4-formylbenzoic acid with 1.1 eq. EDC.HCl (N-(3-dimethylaminopropyl)-N'-ethylcarbodiimide hydrochloride) and 1.1 eq. N-hydroxysuccinimide in a solution comprising dichloromethane (DCM) at room temperature (rt), which resulted in formation of an NHS-ester product (see scheme 2):

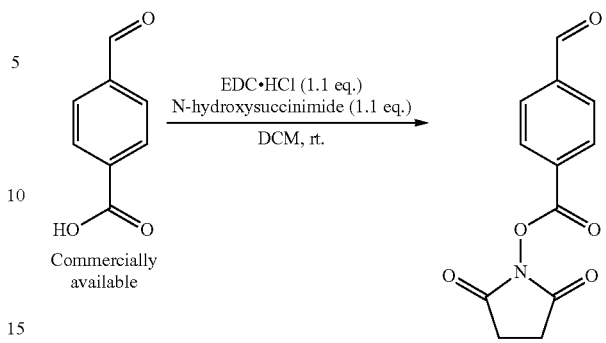

Scheme 2: Synthesis of 4-formylbenzoic acid NHS

DNA Modification

Conjugation of 4-Formylbenzoic Acid NHS Linker to Amino Modified DNA (3' Aldehyde DNA Modification) (Reacting Aldehyde ON)(Compound 3)

The aldehyde NHS product was conjugated covalently to a 3' amino-modified DNA strand (could also be a 5' amino-modified DNA strand)(compound 3 set forth in FIG. 50).

To a solution of DNA (10 nmol) in water (100 µL) was added 4-formylbenzoic acid NHS linker in DMF (300 mM, 100 µL), MeCN (100 µL), and TEA (0.75 µL). The mixture was shaken for 4 h at rt. The DNA was precipitated in an aqueous solution of NaOAc (3 M, 30 µL, pH=5.2), cold EtOH (990 µL), and glycogen (20 mg/mL, 1 µL) by incubation on dry ice for 15 min followed by centrifugation for 1 h (4° C., 20000 g). Immediately hereafter, the supernatant was removed, and the pellet was dissolved in 100 µL TEAA buffer (0.1 M) and purified by RP-HPLC 10-20% MeCN in 0.1 M TEAA over 15 min. Flow=1 mL/min. T=25° C. The product-containing fractions were collected and lyophilized.

Aldehyde ON: $R_t$=7.4 min (47%) LC-MS: [M]; Calc.: 6991 found: 6989.

DNA-Protein Conjugation Reactions

General Procedure for Conjugation Reactions

Nearly identical experimental conditions were used for conjugation reactions to his$_6$-tagged proteins, serotransferrin (Tf), and antibodies. All proteins and antibodies were used without further purification, except Trastuzumab, which was purified by Amicon filtration to remove non-protein components and alkaline phosphatase, which was purified using Illustra microspin G-25 spin columns (purchased from Sigma-Aldrich, US Biological or Roche). Generally, conjugation reactions were performed at a final concentration of 2-7 µM.

DNA Templated Conjugation Reactions on his$_6$-Tagged Proteins, Metalloproteins and Murine IgG1

Conjugations were performed on his-tagged GFP, his tagged ISDH, transferrin, anti-c-Myc, anti-FLAG® M2, anti beta-tubulin and anti beta-actin.

Reactions were performed by mixing Guiding ON (2 µM) with the protein of interest (2 µM), Cu(NO$_3$)$_2$ (6 µM), and Reacting aldehyde ON (2 µM) in phosphate buffer (50 mM, pH 7.5) containing Na$_2$SO$_4$ (500 mM) (or 400 mM NaCl) and Tween®-20 (0.02 v/v %), lastly NaCNBH$_3$ (50 mM) was added. The mixture was left to react overnight at rt before being analyzed/purified by PAGE. The scale (5-500 µl) was varied depending on application. Larger reaction volumes were concentrated using Amicon Ultra® centrifugal filters (MWCO 3000, 14100 g for 30 min), which were prewashed with buffer containing Tween®-20 (0.02 v/v %) before PAGE purification.

Conjugation Reactions on Humanized IgG1 Antibody and Alkaline Phosphatase

DNA conjugation was performed on alkaline phosphatase and Trastuzumab (commercial anticancer drug from Roche) using a similar protocol as for conjugation to his$_6$-tagged proteins was used for antibodies except higher final concentrations (4 µM for alkaline phosphatase and 6 µM for trastuzumab) was used for Reacting aldehyde ON, Guiding ON and 3 eq. Cu(NO$_3$)$_2$ (12/18 µM). The DNA-antibody conjugates were analyzed and purified by 4% native PAGE.

ON Toehold Replacement of Conjugation Products

As previously described after overnight conjugation reaction EDTA (2.5 mM) and an ON complementary to the full sequence of the Guiding ON (2 eq.) was added and left to displace the Reacting ON at room temperature for 30 min before spin filtration (for large scale reactions) of the reaction mixture (3K filters) followed by PAGE purification.

Purification/Isolation of Conjugation Product

Gel-Extraction (Yields):

As previously described protein conjugates were isolated from 4-6% native PAGE gels with Tricine buffer and extracted overnight in EPPS buffer (1.5-2 ml, 50 mM EPPS, 200 mM NaCl, 0.02% *Tween®-20, pH 7.7 or similar buffer). The samples were concentrated using 3K spin filters (prewashed with buffer). The yields were determined by comparing in-gel SYBR® Gold absorbance of the DNA-protein conjugate to a series of internal DNA standards (0.5-4 pmol of 3' amino-modified DNA strand) using the software ImageQuant.

PAGE (5% native) analysis of conjugation reactions to GFP, ISDH, Transferrin and alkaline phosphatase is shown in FIG. 29. PAGE (4% native) analysis of conjugation reactions to Anti-FLAG, Anti beta-tubulin, Anti beta-actin, Anti C myc and Trastuzumab is shown in FIG. 30. The gels show no coupling without the presence of Guiding ON illustrating that the coupling is directed.

Example 8

Site-Selective Insertion of a Bioothogonal Handle on Proteins Using DNA-Templated Conjugation A reacting oligonucleotide conjugated to an aldehyde and a cleavable diol linker was created and conjugated to a metal binding protein. After conjugation and isolation the linker was cleaved from the protein leaving an aldehyde functionality (bioorthogonal handle) attached to the protein. This aldehyde was further conjugated to amino-oxy PEG with an average MW of 5000 Da. The aldehyde-DNA with a cleavable linker was created by synthesizing a NHS-ester product that was subsequently conjugated to an amino-modified DNA strand.

FIG. 31 shows DNA-templated protein conjugation using reductive amination, cleavage and coupling of amino-oxy functionalized molecules. The Guiding ON modified with tris(NTA) coordinates the metal-binding protein through an interaction with metal ions. The partly complementary Reacting cleavable aldehyde ON reacts with nearby lysine residues in the presence of a reducing agent like NaCNBH$_3$. The modified DNA protein conjugate is purified and then the cleavable linker is cleaved using an oxidizing agent leaving an aldehyde functionality on the protein. This can be further reacted with aminooxy-functionalized small-molecules or polymers.

Synthesis

Dihydroxy Cleavable Linker 2,3-diacetoxy-4-((4-formylbenzyl)amino)-4-oxobutanoic Acid (Compound 4)

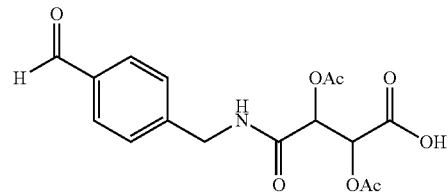 [SMILES: CC(=O)OC(C(=O)O)C(OC(C)=O)C(=O)NCc1ccc(C=O)cc1]

Diacetyl tartaric anhydride (500 mg; 2.78 mmol; 1.0 eq.) was added to a solution of (4-(dimethoxymethyl)phenyl)methanamine (503 mg; 2.78 mmol; 1.2 eq.) in dry DCM (4.5 mL) at 0° C. The reaction was allowed to warm to rt and stirred overnight. The solvent was removed in vacuo and the residue taken up in EtOAc. The organic phase was washed with 1 M aq. HCl (×2) and brine, dried over MgSO$_4$ and concentrated in vacuo. The product was a white solid (760 mg, 83%), which used without further purification. R$_f$=0.22 (MeOH:DCM 1:9 and 0.1% Formic acid); $^1$H-NMR (400 MHz, d6-DMSO) δ 13.66 (s, 1H), 9.98 (s, 1H), 8.89 (t, J=5.91, 1H), 7.87 (d, J=8.09, 2H), 7.41 (d, J=8.09, 2H), 5.56 (d, J=2.48, 1H), 5.53 (d, J=2.48, 1H), 4.47 (dd, J=6.08=16.00, 1H), 2.13 (s, 3H), 2.03 (s, 3H); $^{13}$C-NMR (100 MHz, d6-DMSO) δ 192.8, 169.6, 169.4, 167.6, 165.6, 146.1, 135.1, 129.6, 127.5, 71.8, 71.2, 42.0, 20.7, 20.3; HRMS (ESI) calc. for C$_{16}$H$_{17}$NO$_8$ ([M+H]+) 352.1027, found 352.1032.

2,3-diacetoxy-4-((4-formylbenzyl)amino)-4-oxobutanoic Acid (Compound 5)

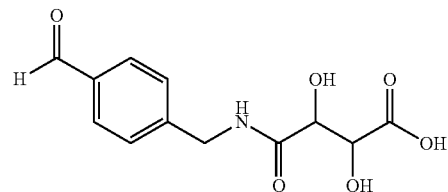 [SMILES: O=Cc1ccc(CNC(=O)C(O)C(O)C(=O)O)cc1]

The aldehyde (4) (100 mg; 0.28 mmol; 1 eq.) was dissolved in MeOH (3 mL). KOH (160 mg; 2.85 mmol; 10 eq.) in H$_2$O (3 mL) was added dropwise at 0° C. The reaction was allowed to warm to rt and stirred for 3 h. The methanol was removed under reduced pressure, and the remaining solution was acidified using 1 M aq. HCl. The water phase was extracted with EtOAc (×3). The combined organic layers were washed with brine, dried over MgSO$_4$, and concentrated in vacuo. The product was isolated as a white solid (31 mg; 41%). R$_f$=0.24 (MeOH:DCM 1:1); 1H-NMR (400 MHz, d6-DMSO) δ 9.97 (s, 1H), 8.41 (t, J=6.02, 1H), 7.83 (d, J=8.0, 2H), 7.50 (d, J=8.0, 2H), 6.03-5.57 (br s, 1H), 5.40-4.85 (br s, 1H), 4.53-4.21 (m, 4H); 13C-NMR (100 MHz, d6-DMSO) δ 192.8, 173.9, 171.9, 146.8, 134.9, 129.5, 127.6, 73.2, 71.8, 41.9.

2,5-dioxopyrrolidin-1-yl 4-((4-formylbenzyl)amino)-2,3-dihydroxy-4-oxobutanoate (Compound 6)

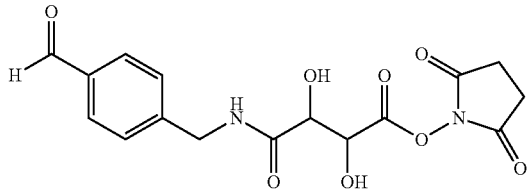 [SMILES: O=Cc1ccc(CNC(=O)C(O)C(O)C(=O)ON2C(=O)CCC2=O)cc1]

To a solution of the acid (5) (31 mg; 0.12 mmol; 1 eq.) and N-hydroxysuccinimide (15 mg; 0.13 mmol; 1.1 eq.) in dry THF (3 mL) at 0° C. was added N,N-dicyclohexylcarbodiimide (26 mg; 0.13 mmol; 1.1 eq.). The reaction was stirred at rt overnight and filtered to remove the precipitate. The dihydroxy-4-oxobutanoate crude mixture was concentrated in vacuo and used to couple onto amine modified DNA without further purification.

DNA Modification

Conjugation of Aldehyde NHS Cleavable Linker (6) to Amino Modified DNA (3' Aldehyde DNA Modification) (Cleavable Reacting ON)(7)

The aldehyde NHS product was conjugated covalently to a 3' amino-modified DNA strand (could also be a 5' amino-modified DNA strand) directly after synthesis) (compound 7 as set forth in FIG. 51).

To a solution of DNA (10 nmol) in water (100 μL) was added aldehyde NHS cleavable linker (6) in DMF (approx. 300 mM, 100 μL), MeCN (100 μL), and TEA (0.75 μL). The mixture was shaken for 4 h at rt and. The DNA was precipitated in an aqueous solution of NaOAc (3 M, 30 μL, pH=5.2), cold EtOH (990 μL), and glycogen (20 mg/mL, 1 μL) by incubation on dry ice for 15 min followed by centrifugation for 1 h (4° C., 20000 g). Immediately hereafter, the supernatant was removed, and the pellet was dissolved in 100 μL TEAA buffer (0.1 M) and purified by RP-HPLC 10-20% MeCN in 0.1 M TEAA over 15 min. Flow=1 mL/min. T=25° C. The product-containing fractions were collected and lyophilized.

Aldehyde ON: $R_t$=6.2 min (28%) ESI-MS: [M]; Calc.: 7108 found: 7108.

DNA-Protein Conjugation Reactions

General Procedure for Conjugation Reactions

Conjugation reactions, toehold replacement and purification were performed as in example 7 for his-tagged proteins, metallo-proteins and IgG antibodies. After gel extraction of the product bands the samples were concentrated using 3K spin filters (prewashed with buffer) and further purified by buffer exchange using illustra Microspin G-25 columns. The yields were determined by comparing in-gel SYBR® Gold absorbance of the DNA-protein conjugate to a series of internal DNA standards (0.5-4 pmol of 3' amino-modified DNA strand) using the software ImageQuant.

Cleavage of Diol Linker and Conjugation with Aminooxy-PEG

The DNA protein conjugate is then incubated with NaIO$_4$ (1 mM) in NaOAc with Tween-20 (pH 5.5, 100 mM) for 1 h at RT. Then excess reagents are removed and the sample buffer exchanged by Illustra microspin G-25 spin columns into Phosphate buffer with Tween-20 (pH 6.5, 50 mM). Then aminooxy PEG5000 (1 mM) and para-phenylene diamine (2 mM) is added to the protein and the sample incubated over night at RT and analyzed by SDS PAGE (NuPAGE 4-12% bistris gel) and stained with Simply blue Safestain.

FIG. 32 is a reaction scheme showing 1) DNA-templated protein conjugation with reductive amination on his-tagged GFP followed by 2) removal of DNA by NaIO$_4$ cleavage of diol linker. This leaves an aldehyde functionalized GFP which is further reacted with PEG-ONH$_2$.

Cleavage of cleavable linker (compound 7) after reacting with GFP and coupling with PEG is shown in FIG. 33. The gel shows that no cleavage and coupling occur for GFP alone, however with GFP-DNA conjugate (made with Compound 7) the DNA is removed using NaIO$_4$. This results in a gel shift and leaves an aldehyde on the protein. This aldehyde can be further reacted with PEG-ONH$_2$ as shown in lane 6, also resulting in a significant gel shift.

Glycosylated Proteins

Cleavage of the diol-cleavable linker on glycosylated proteins can potentially pose a problem, as certain carbohydrates are prone to cleavage under similar cleavage conditions with NaIO$_4$. To avoid this problem the protein can be deglycosylated.

IgG Antibody Deglycosylation

IgG antibody (25 μM) was mixed with PNGase F (50.000 units/ml) in PBS Tween buffer (1×) and incubated over night at 37 deg C. PNGase was removed by Amicon 100K filtration. Further conjugations, cleavage and coupling conditions were carried out as previously described in this example.

FIG. 34 shows for the IgG Trastuzumab that treatment with NaIO$_4$ followed by coupling with PEG-ONH$_2$ results in unspecific coupling (lane 1 and 2). However if the IgG has been pretreated with PNGase to remove glycans there is no reaction with PEG-ONH$_2$ (lane 3-6). Before SDS PAGE the antibody is reduced into heavy and light chain with 50 mM DTT.

In FIG. 35 is shown that there is a selective conjugation of one PEG chain to the deglycosylated antibody, which contain an aldehyde from cleavage of the diol DNA linker (lane 7-9). Periodate treatment and PEG coupling of the glycosylated antibody leads to multiple unspecific couplings (lane 1-3), whereas the deglycosylated antibody doesn't show any coupling (4-6). There is two bands in lane 7 and 9 as only one of two comparable heavy chains of the antibody contain a DNA strand or PEG chain respectively.

Example 9

Site-Selective Insertion of a Single Thiol on Proteins Using DNA-Templated Conjugation A reacting oligonucleotide conjugated to an NHS ester and a cleavable disulphide linker was created and conjugated to a metal binding protein. After conjugation and isolation the linker was cleaved from the protein leaving a thiol functionality attached to the protein. This thiol can be further conjugated to e.g. maleimide or iodoacetamide containing linkers.

Generally installation of a free bioorthogonal thiol group will work for proteins which doesn't contain free cysteine, but cysteines bound in disulphide bridges or no cysteines. The cleavage of the DNA disulphide strand could be performed in two different ways depending on the protein. Generally for proteins containing disulphides the linker could be cleaved using a fully complementary thiol-DNA strand as shown in FIG. 36. For IgG antibodies cleavage of the linker could also be obtained by mild reduction, reducing both interchain disulphides and the DNA linker. This can then be followed by reoxidation of the antibody and coupling of the newly introduced thiol, see FIG. 37. The NHS-disulphide-DNA with a cleavable linker was created by synthesizing a NHS-ester product that was subsequently conjugated to an amino-modified DNA strand.

Synthesis

Long DSP NHS Linker (LDSP, 8)

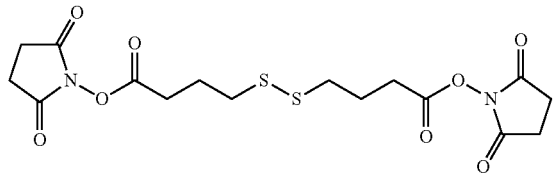 [SMILES: O=C(CCCSSCCCC(=O)ON1C(=O)CCC1=O)ON1C(=O)CCC1=O]

Compound 8 NHS Ester of 4,4'-Dithiodibutyric Acid (LDSP)

The NHS ester of 4,4'-dithiodibutyric acid (8) was prepared as for DSS and DSP described in the Experimental Methods (Formula 1 and 2).

DNA Modification

Conjugation of Disulphide Cleavable Linker LDSP (8) to Amino Modified DNA (LDSP Cleavable Reacting ON) (9)

DNA modification with Long DSP NHS linker (8) was performed as for Conjugation of DSS/DSP linker to amino modified DNA described in the Experimental Methods. The NHS linker was conjugated covalently to a 3' amino-modified DNA strand (could also be a 5' amino-modified DNA strand) (compound 9 as set forth in FIG. 52).

LDSP cleavable reacting ON: $R_t$=13.5 min

DNA-Protein Conjugation Reactions

General Procedure for Conjugation Reactions

Conjugation reactions and purifications were performed as described in the methods section and in Example 1,2, and 6 depending on the protein (his-tagged, transferrin, antibody).

DNA-Templated Disulphide Cleavage and Site-Selective Coupling

Preparation of Thiol DNA:

A DNA strand fully complementary to the reacting ON (e.g. Thiol DNA: 5'-Thiol-Modifier C6 S-SGGG CTC ATG CGA GGC TGT ATG T (SEQ ID NO:3)) and with a free thiol was used to cleave the disulphide bridge between the DNA and the DNA-protein conjugate.

The DNA strand was reduced with TCEP (100 mM) and HPLC purified by RP-HPLC 10-20% MeCN in 0.1 M TEAA over 15 min. Flow=1 mL/min. T=25° C. The product-containing fractions were collected and lyophilized.

Reduction of Protein-DNA Conjugate:

The purified Transferrin-DNA conjugate (1 µM) was mixed with thiol DNA (1 µM) in NaCl (0.3 M) and EPPS buffer (50 mM, pH 7.7, 0.02% Tween 20) in a total volume of 10 µl. It was left to react for 1-2 h.

Maleimide Coupling to Protein-Thiol

The Protein-thiol after DNA-templated reduction was mixed with PEG5000 maleimide (0.5 mM) and reacted for a couple of hours. The reaction was analyzed by SDS PAGE.

FIG. 38 shows DNA-templated reduction and maleimide coupling to single thiol on protein. In lane 1 is shown the Transferrin-DNA conjugate. Lane 2 shows this conjugate after reaction with PEG5000 maleimide, no significant gel shift occurs indicating no free thiols present on the protein. In lane 3 the thiol DNA is added to the transferrin-DNA conjugate, this leads to a band shift because some of the DNA is removed from the conjugate. In lane 4 the thiol DNA is again used for cleavage of the transferrin-DNA conjugate and the newly formed free thiol is further reacted with PEG5000 maleimide, leading to an upward gel shift.

Reduction and Reoxidation of IgG Antibodies

Procedure was inspired by Junutula J. R. et al. Nat. Biotech. 2008.

Anti C-myc (0.25 µM) was mixed with TCEP in different concentration (0.1, 1 or 10 mM) in EPPS buffer (50 mM, pH 7.7) containing Tween-20 (0.02%). It was reacted for 45 min. at RT. Then CuSO4 was added in 2 eq. compared to TCEP and the mixture left to reoxidize for 3 h at RT. The reaction scheme was analyzed by SDS PAGE (NuPAGE 4-12% bistris).

As shown in FIG. 39 Anti C-myc can be both reduced and reoxidized using TCEP and Cu(II). The antibody is partially reduced with 1 mM TCEP and fully reduced with 5 and 10 mM TCEP. Reoxidation is less complete with high concentrations of TCEP.

TCEP Cleavage of Disulphide Linker on DNA Protein Conjugate:

Different amounts of TCEP (1, 3, 5, or 7 mM) was added to purified Anti C-myc DNA conjugate with disulphide linker (0.25 µM) in PBS buffer containing 0.02% Tween-20. The mixture was incubated at room temperature for 1 h and analyzed by 4% Native PAGE.

As shown in FIG. 40 cleavage occurs already with 1 mM TCEP, showing that very mild conditions can be used for cleavage of the linker. This indicates that full reduction of the antibody is unnecessary for full linker cleavage.

Reduction and Reoxidation of Protein-DNA Conjugate Followed by Maleimide Coupling Anti C-myc-DNA conjugate (0.9 µM) was mixed with TCEP (1 mM) in PBS buffer (1×) containing Tween-20 (0.02%). It was reacted for 1 h at RT. Then CuSO4 was added in 2 eq. compared to TCEP and the mixture was left to reoxidize for 3 h at RT. Then EDTA (2.5 eq. compared to CuSO4) was added to complex the copper. The protein was then purified using Illustra microspin G-25 columns, which had been preequilibrated with PBS Tween. Lastly the protein-thiol was reacted with PEG500 maleimide (or Fluorescein maleimide) (1 mM) for 1 h. The reactions were analyzed by SDS PAGE (NuPAGE 4-12% bistris).

Example 10

Site-Selective Insertion of an Aniline Handle on Proteins Using DNA-Templated Conjugation A reacting oligonucleotide conjugated to an aldehyde and a cleavable azo linker was created and conjugated to a metal binding protein. After conjugation and isolation the linker was cleaved from the protein leaving an aniline functionality (bioorthogonal handle) attached to the protein. This aniline was further conjugated to o-aminophenol PEG with an average MW of 10000 Da. The aldehyde-DNA with a cleavable linker was created by synthesizing a NHS-ester product that was subsequently conjugated to an amino-modified DNA strand.

Synthesis of an Azobenzene-NHS Ester

Compound 10

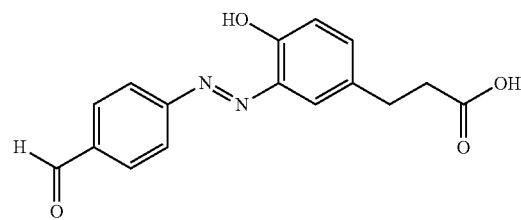 [SMILES: O=Cc1ccc(/N=N/c2cc(CCC(=O)O)ccc2O)cc1]

NaNO$_2$ (7 eq.) was added portion-wise to a solution of 4-aminobenzaldehyde (2 eq.) in 6 M HCl (10 mL/mmol hydroxyphenyl-acid) at 0° C. The mixture was stirred for 45 min at 0° C., and subsequently added to a solution of a hydroxyphenyl-acid (1 eq.). The pH was adjusted to pH=8 by addition of solid NaHCO$_3$ at 0° C. The reaction was stirred overnight at rt. The reaction was quenched with conc. aq. HCl, and the pH adjusted to 1. The solution was extracted with EtOAc (×3). The combined organic phases were washed with brine, dried Na$_2$SO$_4$, and evaporated onto celite under reduced pressure. The compound was purified by flash column chromatography to obtain 10.

Product name: 3-(3-((4-formylphenyl)diazenyl)-4-hydroxyphenyl)propanoic acid; flash column chromatography (EtOAc:Pentane 15% to 30%, with 0.5% Formic acid); yield=28%; orange solid; R$_f$=0.28 (EtOAc:Pentane 1:1 and 0.1% formic acid); $^1$H-NMR (400 MHz, d6-DMSO) δ 12.12 (s, 1H), 10.87 (s, 1H), 10.11 (s, 1H), 8.16 (d, J=8.41, 2H), 8.11 (d, J=8.41, 2H), 7.62 (d, J=1.82, 1H), 7.37 (dd, J=1.82=8.45, 1H), 7.02 (d, J=8.45, 1H), 2.82 (t, J=7.55, 2H), 2.55 (t, J=7.55, 2H); $^{13}$C-NMR (100 MHz, d6-DMSO) δ 192.7, 173.7, 154.9, 153.9, 138.5, 137.2, 135.0, 132.4, 130.7, 123.2, 120.8, 118.4, 35.2, 29.3; HRMS (ESI) calc. for C$_{16}$H$_{14}$N$_2$O$_4$ ([M+H]+) 299.1026, found 299.1027.

Compound 11

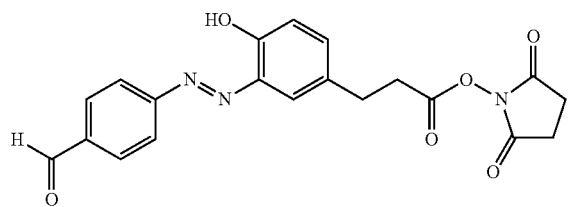 [SMILES: O=Cc1ccc(/N=N/c2cc(CCC(=O)ON3C(=O)CCC3=O)ccc2O)cc1]

The acid 10 (1 eq) and N-hydroxysuccimide (1.2) was dissolved in dry DCM (1.4 mL/mmol acid). EDC.HCl (1.2) was added slowly at 0° C. The reaction mixture was stirred for 2 h at 0° C. under an argon atmosphere. The reaction mixture was diluted with DCM. The organic phase was washed with a 2.5% aq. solution of NaHSO$_4$ (×2) and brine, dried over Na$_2$SO$_4$, filtered and concentrated in vacuo. The crude mixture was used for coupling to an amine without further purification.

The aldehyde NHS 11 was conjugated covalently to a 3' amino-modified DNA strand (could also be a 5' amino-modified DNA strand) (compound 12 set forth in FIG. 53) directly after synthesis.

To a solution of DNA (10 nmol) in water (100 µL) was added aldehyde NHS cleavable linker 11 in DMF (approx. 150 mM, 100 µL), MeCN (100 µL), and TEA (1 µL). The mixture was shaken for 2 h at rt. The DNA was precipitated in an aqueous solution of NaOAc (3 M, 30 µL, pH=5.2), cold EtOH (990 µL), and glycogen (20 mg/mL, 1 µL) by incubation on dry ice for 15 min followed by centrifugation for 1 h (4° C., 20000 g). Immediately hereafter, the supernatant was removed, and the pellet was dissolved in 100 µL TEAA buffer (0.1 M) and purified by RP-HPLC 10-20% MeCN in 0.1 M TEAA over 15 min. Flow=1 mL/min. T=25° C. The product-containing fractions were collected and lyophilized.

Aldehyde Azo ON: R$_t$=14.5 min.

Conjugation Using the Azobenzene Cleavable Linker-DNA

Conjugation reactions, toehold replacement and purification were performed as in Example 7 for his-tagged proteins, metallo-proteins and IgG antibodies. After gel extraction of the product bands the samples were concentrated using 3K spin filters (prewashed with buffer) and further purified by buffer exchange using Illustra Microspin G-25 columns.

The coupling of the azobenzene linked-DNA 12 and aldehyde-modified DNA 3 was compared using the proteins his$_6$-tagged GFP, Tf and Cmyc. The conjugation reactions showed similar conversions for the two modified DNAs which is shown in FIG. 41.

Cleavage and Conjugation of the Azobenzene Linker

The DNA protein conjugate is then incubated with Na$_2$S$_2$O$_4$ (25 mM) in Phosphate buffer (pH 6.5, 25 mM) for 1 min at RT. Then excess reagents are removed and the sample buffer exchanged by Illustra microspin G-25 spin columns in Phosphate buffer (pH 6.5, 25 mM). Then o-aminophenol PEG10,000 (5-10 equiv) and K$_3$Fe(CN)$_6$ (50-100 equiv) is added to the protein and the sample incubated 15 min at RT followed by purification using 3K spin filters (five washed with the phosphate buffer). The reaction was analyzed by SDS-PAGE.

The coupling of the DNA to the GFP was performed followed by cleavage of the linker using Na$_2$S$_2$O$_4$ forming an aniline modified GFP as shown in FIG. 42. O-aminophenol-PEG10,000 was coupled to the aniline modified GFP as shown by the faint band in lane 5.

Example 11

In order to synthesize the guiding oligonucleotide (Guiding ON) the procedure by Goodman et al. in Chembiochem, 2009 have been followed as described above. Another approach is to use a protected-NTA-phosphoramidite in solid-phase oligonucleotide synthesis to obtain the desired DNA sequence with multiply (1, 2, 3, 4 or 5) NTA-moieties in the 3' or 5' end of the DNA strand. Examples of protected-NTA-phosphoramidites are shown in formula 12, 13, 14 and 15. The procedure for the synthesis of the structures in formula 12 and 13 is shown below.

See FIGS. 43, 44 and 45 for overview and compound numbers.

Compound 13

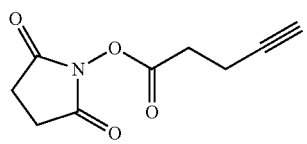

To a solution of the acid (4.3 mmol) in dry DCM (5 mL) were added EDC-HCl (7.8 mmol) and N-hydroxysuccinimide (4.9 mmol). The mixture was stirred for 2 h, before the reaction mixture was washed with 2.5% aq. NaHSO$_4$ (2×10 mL) and brine (10 mL). The organic phase was dried over Na$_2$SO$_4$, filtered and concentrated in vacuo. The resulting compound was used without further purification.

$^1$H NMR (400 MHz, CDCl$_3$) δ 2.93-2.78 (m, 6H), 2.62 (td, J=7.5, 2.5, 2H), 2.05 (t, J=5.1 Hz, 1H). $^{13}$C NMR (100 MHz, CDCl$_3$) δ 169.0, 167.1, 81.0, 70.2, 30.5, 25.7, 14.3.

Compound 14

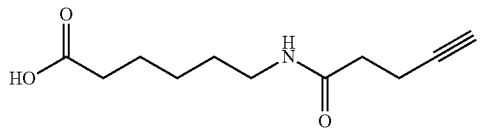

Compound 13 (3.8 mmol) was dissolved in dry DCM (5 mL) before Et$_3$N (1.6 mL) and amino-acid (8.6 mmol) were added. The reaction was left to react overnight before the solvent was evaporated. The residue was dissolved in EtOAc (40 mL) and washed with 1M HCl (3×25 mL), brine (30 mL). The organic phase was dried over MgSO$_4$, filtered and concentrated in vacuo. This yielded compound 14 without further purification.

$^1$H NMR (400 MHz, CDCl$_3$) δ 5.67 (s, 1H), 3.29 (q, J=6.8 Hz, 2H), 2.53 (td, J=6.9, 2.4 Hz, 2H), 2.42-2.33 (m, 4H), 2.01 (t, J=2.5 Hz, 1H), 1.72-1.62 (m, 2H), 1.60-1.49 (m, 2H), 1.45-1.34 (m, 2H). $^{13}$C NMR (100 MHz, CDCl$_3$) δ 177.2, 171.2, 83.2, 69.5, 39.5, 35.6, 33.5, 29.4, 26.4, 24.4, 15.1.

(2R,3R)-3-Amino-4-(bis(4-methoxyphenyl)(phenyl)methoxy)butan-2-ol (15)

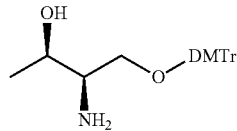

DMTr protected threoninol was synthesized according to known literature by Kumar et al., Org. Biomol. Chem. 2015, 13, 2366-2374.

Compound 16

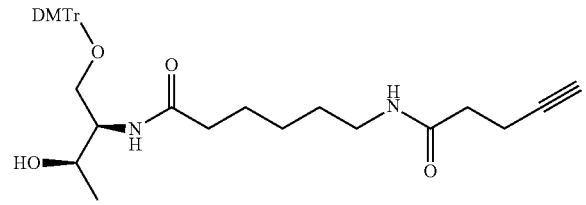

Compound 14 (0.5 mmol) was dissolved in dry DMF (1 mL) before HBTU (1.4 mmol) and DIPEA (0.7 mL) were added. A solution of compound 15 (1.0 mmol) in dry DMF (3 mL) was added and the reaction left overnight. The solvent was evaporated using high vacuum and the residue dissolved in EtOAc (30 mL). The organic phase was washed with aq. sat. NaHCO$_3$ (30 mL), brine (30 mL) dried over Na$_2$SO$_4$, filtered and concentrated. The product was purified using flash column chromatography (0-5% MeOH in DCM with 1% Et$_3$N).

$^1$H NMR (400 MHz, CDCl$_3$) δ 7.37 (d, J=7.2 Hz, 2H), 7.33-7.19 (m, 7H), 6.83 (d, J=8.1 Hz, 4H), 6.07 (d, J=8.5 Hz, 1H), 5.81 (s, 1H), 4.13-4.03 (m, 1H), 3.97-3.88 (m, 1H), 3.79 (s, 6H), 3.43-3.35 (m, 1H), 3.32-3.22 (m, 3H), 3.08-3.01 (m, 1H), 2.55-2.46 (m, 2H), 2.39-2.31 (m, 2H), 2.27-2.19 (m, 2H), 2.02-1.97 (m, 1H), 1.72-1.61 (m, 2H), 1.59-1.48 (m, 2H), 1.48-1.35 (m, 2H), 1.13 (d, J=6.2 Hz, 3H). $^{13}$C NMR (100 MHz, CDCl$_3$) δ 173.3, 171.0, 158.8, 144.5, 135.6, 135.5, 130.1, 130.0, 128.2, 128.0, 127.2, 113.5, 86.9, 83.3, 69.4, 68.9, 65.4, 55.4, 46.1, 39.3, 36.6, 35.5, 29.2, 26.5, 25.2, 20.1, 15.1.

Bromoacetic Acid N-Hydroxysuccinimide Ester (17)

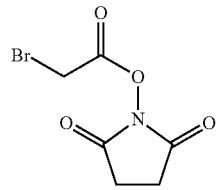 [SMILES: O=C(CBr)ON1C(=O)CCC1=O]

To a suspension of Bromoacetic acid (4.8 mmol) in dry THF (20 mL) were added DCC (5.3 mmol) and N-hydroxysuccinimide (5.5 mmol). The reaction was left for 2 h before the mixture was filtered and used without further work-up.

Fmoc-Lys(Boc)-OMe (18)

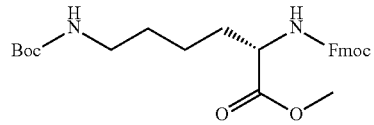

Fmoc-Lys(Boc)-OH (2.3 mmol) was dissolved in dry DMF (10 mL) and K$_2$CO$_3$ (5.0 mmol) was added. Methyl iodide (4.7 mmol) was added dropwise to the solution at 0° C. The reaction mixture was kept at 0° C. for 3.5 h and a further 1.5 h at rt before H$_2$O (10 mL) was added. The mixture was diluted with EtOAc (50 mL) and washed with aq. sat. NaHCO$_3$ (2×50 mL) and brine (50 mL). The organic phase was dried over Na$_2$SO$_4$, filtered and concentrated in vacuo yielding the desired compound.

$^1$H NMR (400 MHz, CDCl$_3$) δ 7.77 (d, J=7.3 Hz, 2H), 7.64-7.57 (m, 2H), 7.40 (t, J=7.2 Hz, 2H), 7.32 (t, J=7.3 Hz, 2H), 5.43-5.33 (m, 1H), 4.63-4.47 (m, 1H), 4.45-4.33 (m, 3H), 4.28-4.19 (m, 1H), 3.75 (s, 3H), 3.17-3.05 (m, 2H), 1.93-1.80 (m, 1H), 1.77-1.65 (m, 1H), 1.65-1.56 (m, 1H), 1.58-1.31 (m, 12H). $^{13}$C NMR (100 MHz, CDCl$_3$) δ (156.2, 156.1, 144.0, 143.9, 141.4, 127.8, 127.2, 125.2, 120.1, 79.4, 77.4, 67.1, 53.8, 52.6, 47.3, 40.2, 32.3, 29.8, 28.6, 22.5.

Fmoc-Lys(2-bromoacetyl)-OMe (19)

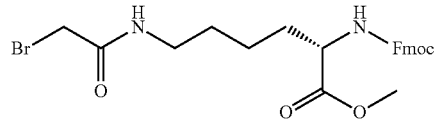

To compound 18 (2.0 mmol) in a round-bottomed flask was added 4M HCl in dioxane (10 mL) and left with stirring for 20 min. The solvent was evaporated and co-evaporated with DCM in vacuo. THF (20 mL) was added to make a suspension of the residue before the solution of compound 12 (4.0 mmol) in THF (20 mL) was added. Et$_3$N (0.48 mL) was added and the reaction was left overnight. The solvent was evaporated and the residue dissolved in EtOAc (50 mL). The organic phase was washed with aq. sat. NaHCO$_3$ (50 mL), 1M HCl (50 mL) and brine (50 mL). The compound was used without further purification.

Fmoc-Lys(2-azidoacetyl)-OMe (20)

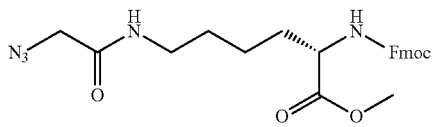

Compound 19 (0.8 mmol) was dissolved in DMF (10 mL) and acetic acid (0.1 mL) was added. A solution of sodium azide (1.2 mmol) in H$_2$O (2 mL) was added to the reaction flask held at 0° C. The reaction was stirred overnight and then diluted with H$_2$O (30 mL). The aqueous phase was extracted with EtOAc (3×40 mL). The combined organic phases were washed with brine, dried over Na$_2$SO$_4$, filtered and concentrated. The product was purified by flash column chromatography (pentane:EtOAc 2:1 to 1:1).

Compound 20 (1.3 mmol) was dissolved in a mixture of DMF and piperidine (3:2, 10 mL) and left with stirring for 1 h. The solvent was evaporated and co-evaporated with DCM (2×15 mL). Purification through a short silica column (7 cm) with eluent pentane:EtOAc (1:1) until byproduct had eluted, followed by MeOH:EtOAc (1:1) for elution of the deprotected amine. The residue was dissolved in dry MeCN (18 mL) before NaHCO$_3$ (6.8 mmol) was added. To the mixture was added methyl bromoacetate (6.6 mmol) and the reaction was kept at reflux overnight. The solvent was evaporated and the residue dissolved in EtOAc (40 mL). The organic phase was washed with aq. sat. NaHCO$_3$ (2×40 mL), brine (30 mL), dried over Na$_2$SO$_4$, filtered and concentrated in vacuo. The product was purified by flash column chromatography (pentane:EtOAc 2:1 to 1:19.

$^1$H NMR (400 MHz, CDCl$_3$) δ 6.51 (s, 1H), 3.96 (s, 2H), 3.72-3.66 (m, 9H), 3.66-3.59 (m, 4H), 3.44 (t, J=7.5 Hz, 1H), 3.34-3.25 (m, 2H), 1.77-1.37 (m, 6H). $^{13}$C NMR (100 MHz, CDCl$_3$) δ 173.1, 171.8, 166.9, 64.4, 52.8, 52.6, 51.9, 51.7, 39.3, 29.7, 28.5, 22.9.

Compound 22

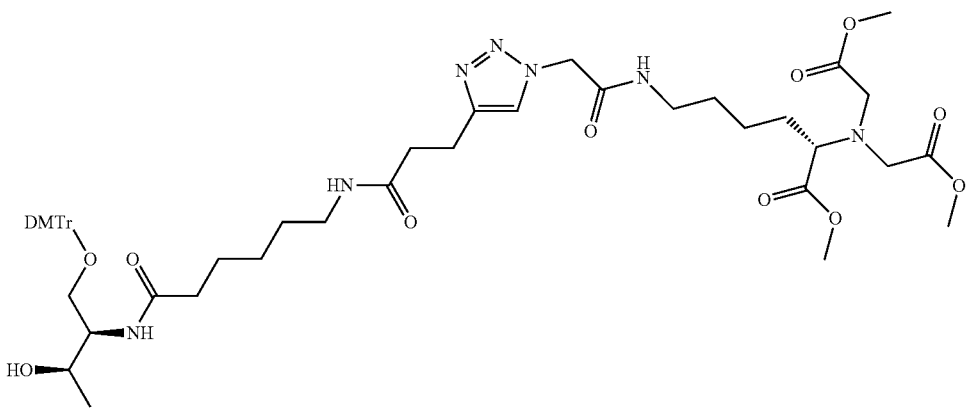

$^1$H NMR (400 MHz, CDCl$_3$) δ 7.77 (d, J=7.3 Hz, 2H), 7.65-7.55 (m, 2H), 7.45-7.36 (m, 2H), 7.36-7.29 (m, 2H), 6.41-6.28 (m, 1H), 5.45-5.29 (m, 1H), 4.50-4.33 (m, 3H), 4.30-4.18 (m, 1H), 3.96 (s, 2H), 3.76 (s, 3H), 3.39-3.22 (m, 2H), 1.93-1.82 (m, 1H), 1.79-1.49 (m, 3H), 1.49-1.31 (m, 2H). $^{13}$C NMR (100 MHz, CDCl$_3$) δ 173.0, 166.8, 144.0, 143.9, 141.5, 127.9, 127.2, 125.2, 120.2, 67.2, 52.9, 52.7, 47.3, 42.8, 39.1, 32.3, 29.0, 22.5.

Dimethyl 2,2'-((6-(2-azidoacetamido)-1-methoxy-1-oxohexan-2-yl)azanediyl)(S)-diacetate (21)

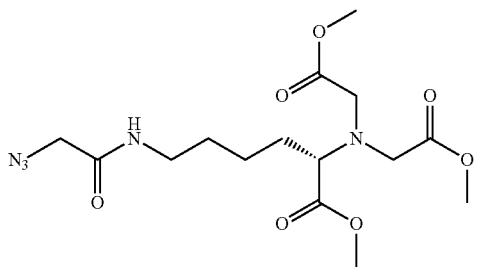 [SMILES: COC(=O)CN(CC(=O)OC)[C@@H](CCCCNC(=O)CN=[N+]=[N-])C(=O)OC]

To a solution of compound 16 (0.36 mmol) in H$_2$O/tBuOH (1:1, 4 mL) was added compound 17 (0.32 mmol). To the mixture was added CuSO$_4$—H$_2$O (0.05 mmol) and sodium ascorbate (0.18 mmol) and the reaction was left overnight with stirring. The mixture was diluted with EtOAc (20 mL) and the organic phase was subsequently washed with aq. sat. NaHCO$_3$ (20 mL), brine (20 mL), dried over Na$_2$SO$_4$, filtered and evaporated. The product was purified by flash column chromatography (0.5% to 5% MeOH in DCM with 1% Et$_3$N).

$^1$H NMR (400 MHz, CDCl$_3$) δ 7.57 (s, 1H), 7.41-7.34 (m, 2H), 7.28 (s, 6H), 6.86-6.78 (m, 4H), 6.78-6.70 (m, 1H), 6.23 (d, J=8.6 Hz, 1H), 6.08-6.01 (m, 1H), 5.58 (s, 1H), 5.01 (d, J=2.3 Hz, 2H), 4.14-4.04 (m, 1H), 3.99-3.91 (m, 1H), 3.78 (s, 6H), 3.72-3.65 (m, 9H), 3.63-3.56 (m, 5H), 3.45-3.33 (m, 2H), 3.31-3.16 (m, 3H), 3.07 (d, J=14.0 Hz, 4H), 2.64-2.54 (m, 2H), 2.26-2.17 (m, 2H), 1.71-1.36 (m, 12H), 1.13 (d, J=6.3 Hz, 3H).

Compound 23

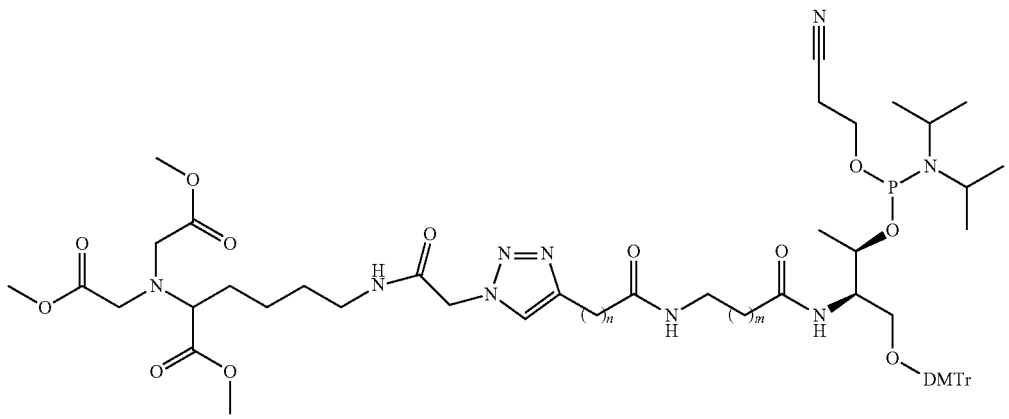

Compound 22 (0.26 mmol) was dissolved in dry DCM (5 mL) before DIPEA (0.6 mmol) and 2-cyanoethyl N,N-diisopropylchlorophosphoramidite (0.5 mmol) were added. The reaction was left with stirring for 2 h before the mixture was diluted with DCM (10 mL) and transferred to aq. sat. NaHCO$_3$ (15 mL). The organic phase was collected, dried over Na$_2$SO$_4$, filtered and concentrated. Flash column purification was performed to separate the product from unreacted starting material. The product was used without further purification in the automated solid-phase oligonucleotide synthesis.

Compound 24

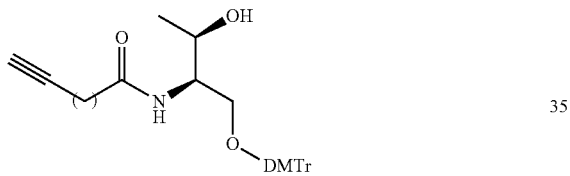

Alkyne-acid (0.5 mmol) was dissolved in dry DMF (1 mL) before HBTU (1.4 mmol) and DIPEA (0.7 mL) were added. A solution of compound 15 (1.0 mmol) in dry DMF (3 mL) was added and the reaction left overnight. The solvent was evaporated using high vacuum and the residue dissolved in EtOAc (30 mL). The organic phase was washed with aq. sat. NaHCO$_3$ (30 mL), brine (30 mL) dried over Na$_2$SO$_4$, filtered and concentrated. The product was purified using flash column chromatography (0-5% MeOH in DCM with 1% Et$_3$N).

Compound 25

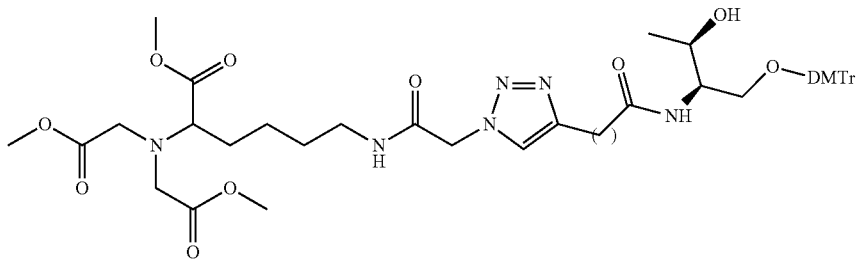

To a solution of compound 24 (0.36 mmol) in H$_2$O/tBuOH (1:1.4 mL) was added compound 21 (0.32 mmol). To the mixture was added CuSO$_4$—H$_2$O (0.05 mmol) and sodium ascorbate (0.18 mmol) and the reaction was left overnight with stirring. The mixture was diluted with EtOAc (20 mL) and the organic phase was subsequently washed with aq. sat. NaHCO$_3$ (20 mL), brine (20 mL), dried over Na$_2$SO$_4$, filtered and evaporated. The product was purified by flash column chromatography (0.5% to 5% MeOH in DCM with 1% Et$_3$N).

Compound 26

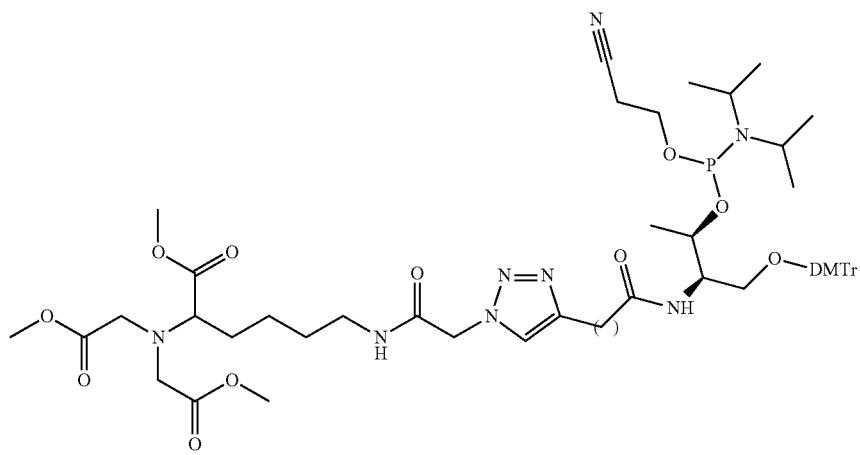

Compound 24 (0.26 mmol) was dissolved in dry DCM (5 mL) before DIPEA (0.6 mmol) and 2-cyanoethyl N,N-diisopropylchlorophosphoramidite (0.5 mmol) were added. The reaction was left with stirring for 2 h before the mixture was diluted with DCM (10 mL) and transferred to aq. sat. NaHCO$_3$ (15 mL). The organic phase was collected, dried over Na$_2$SO$_4$, filtered and concentrated. Flash column purification was performed to separate the product from unreacted starting material. The product was used without further purification in the automated solid-phase oligonucleotide synthesis.

Synthesis of the Guiding ON (Formula 19)

The tris(NTA)-DNA strand was synthesized using the standard protocol for oligonucleotide synthesis via the phosphoramidite synthesis with small changes for the protected-NTA-phosphoramidite coupling step. The protected-NTA-phosphoramidite was dissolved (100 mM solution) in anhydrous acetonitrile and coupled to the growing DNA strand with extended coupling time, 4 min per coupling step. After the desired DNA strand had been synthesized the DNA was deprotected and cleaved from the solid support with a solution of either NaOH or LiOH in H$_2$O:MeOH, or a solution of ammonium hydroxide. The DNA strand was purified by RP-HPLC 10-20% MeCN in 0.1 M TEAA over 15 min. Flow=1 mL/min. T=25° C. The product-containing fractions were collected and lyophilized.

Formula 19

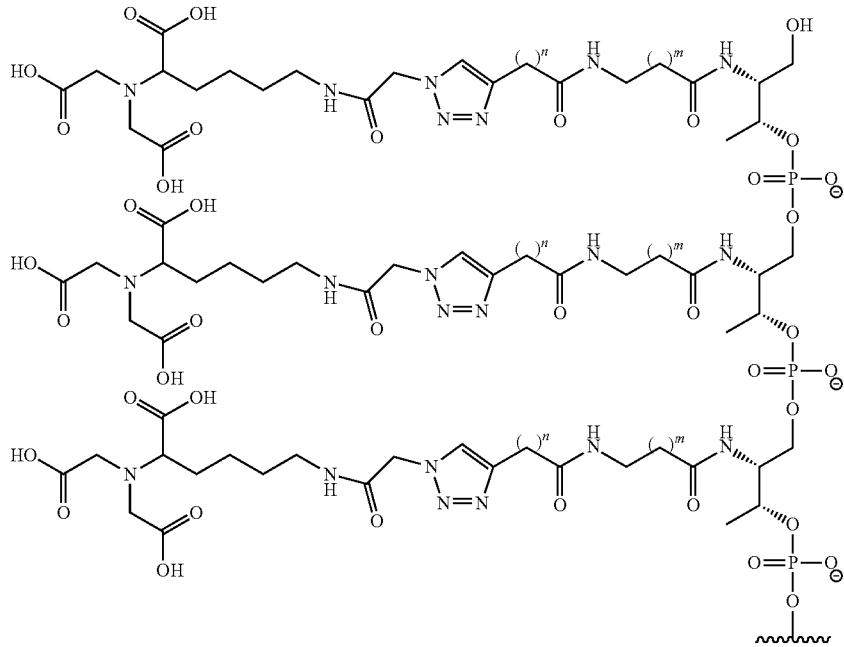

n = 1, 2, 3 or 4, m = 1, 2, 3 or 4

Example 12

Metal Directed Small Molecule Labeling Using Reductive Amination

A small molecule containing an aldehyde and two NTA-moieties were synthesized (see compound 37 and compound 38) and conjugated to a metal binding protein.

Synthesis of the Small Molecules

Compound 27

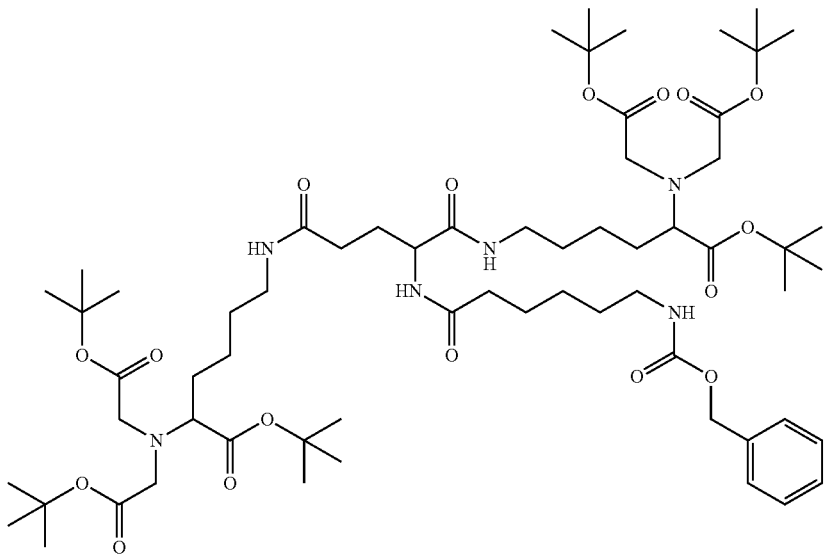 [SMILES: CC(C)(C)OC(=O)CN(CC(=O)OC(C)(C)C)C(CCCCNC(=O)CCC(NC(=O)CCCCCNC(=O)OCc1ccccc1)C(=O)NCCCCC(C(=O)OC(C)(C)C)N(CC(=O)OC(C)(C)C)CC(=O)OC(C)(C)C)C(=O)OC(C)(C)C]

The diNTA (Lata, S.; Reichel, A.; Brock, R.; Trampe, R.; Piehler, J. *J. Am. Chem. Soc* 2005, 127, 10205-10215) (1 eq), Cbz-protected linker (Schmuck, C.; Rehm, T.; Geiger, L.; Schaefer, M. *J. Org. Chem.* 2007, 72, 6162-6170) (1.3 eq) and HBTU (1.8 eq) was dissolved in a solution of TEA (2 eq) and dry DCM (10 mL/mmol diNTA). The reaction was stirred overnight under an argon atmosphere and at rt. The volatiles were removed under reduced pressure. The residue was dissolved in EtOAc, and the organic phase washed with a sat. aq. solution of $NaHCO_3$ (×2) and brine, dried over anhydr. $MgSO_4$ and concentrated in vacuo. Flash column chromatography afforded 27.

$^1$H NMR (400 MHz, $CDCl_3$) δ 7.37-7.27 (m, 6H), 7.21 (d, J=6.5 Hz, 1H), 6.98 (t, J=6.2 Hz, 1H), 6.58 (t, J=5.5 Hz, 1H), 5.05 (s, 2H), 4.34 (q, J=6.5 Hz, 1H), 3.51-3.32 (m, 10H), 3.30-3.09 (m, 6H), 2.46-2.30 (m, 2H), 2.27-2.13 (m, 2H), 2.04-1.94 (m, 2H), 1.70-1.19 (m, 72H).

Compound 28

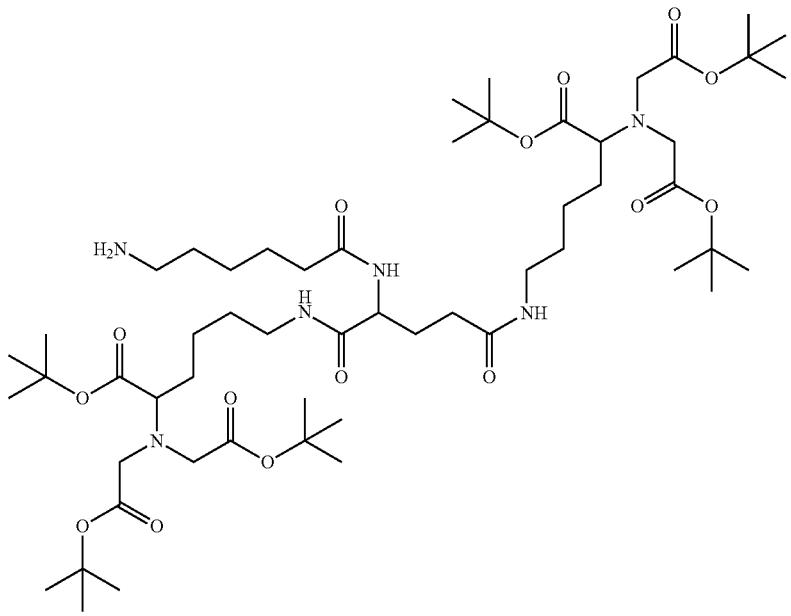 [SMILES: CC(C)(C)OC(=O)CN(CC(=O)OC(C)(C)C)C(CCCCNC(=O)CCC(NC(=O)CCCCCN)C(=O)NCCCCC(C(=O)OC(C)(C)C)N(CC(=O)OC(C)(C)C)CC(=O)OC(C)(C)C)C(=O)OC(C)(C)C]

The protected amine 27 (1 eq) was dissolved in MeOH (10 mL/mmol A). Pd/C (0.1 eq) was added and the reaction was stirred under H₂ atmosphere (1 atm., balloon) for 6 hours at rt. The reaction mixture was filtered through a celite plug and concentrated in vacuo, which afforded 28.

Compound 29

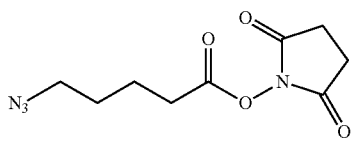 [SMILES: [N-]=[N+]=NCCCCC(=O)ON1C(=O)CCC1=O]

To a solution of the acid (Guerrant, W; Patil, V; Canzoneri, J. C.; Yao, L.-P.; Hood, R.; Oyelere, A. K. *Bioorg. Med. Chem. Lett.* 2013, 23, 3283-3287.) (1 eq) and N-hydroxylsuccimide (1.2 eq) in dry DCM (1.4 mL/mmol acid) was added EDC HCl (1.2 eq). The reaction mixture was stirred for 2 h under an argon atmosphere at rt. The reaction mixture was diluted with DCM and the organic phase was with 10% aq. NaHSO₄ (×2) and brine, dried over NaSO₄ and concentrated in vacuo. This afforded the NHS-ester D, which was used for coupling to an amine without further purification.

¹H NMR (400 MHz, CDCl₃) δ (3.34 (t, J=6.5 Hz, 2H); 2.84 (s, 4H), 2.66 (t, J=7.0, 2H), 1.94-1.79 (m, 2H), 1.77-1.65 (m, 2H).

Compound 30

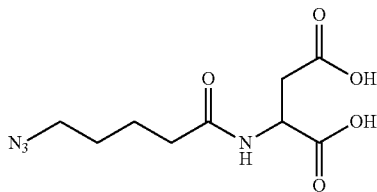 [SMILES: [N-]=[N+]=NCCCCC(=O)NC(CC(=O)O)C(=O)O]

Aspartic acid (2 eq.) was dissolved in DMF (2.5 mL/mmol NHS-ester). The NHS-ester 29 (1 eq) was added at 0° C. and the reaction was stirred overnight at rt. The solvent was evaporated under reduced pressure and the residue taken up in EtOAc. The organic phase was washed with 1 M aq. HCl and brine, dried over MgSO₄ and concentrated in vacuo affording 30.

¹H NMR (400 MHz, d6-DMSO) δ 12.49 (br s, 1H), 8.16 (d, J=7.9 Hz, 1H), 4.52 (q, J=7.5 Hz, 1H), 3.32 (t, J=6.0 Hz, 2H), 2.73-2.62 (m, 1H), 2.61-2.50 (m, 1H), 2.13 (t, J=6.2 Hz, 2H), 1.60-1.44 (m, 4H).

Compound 31

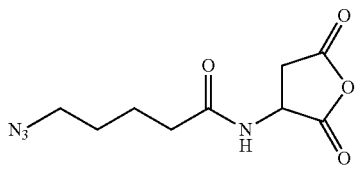 [SMILES: [N-]=[N+]=NCCCCC(=O)NC1CC(=O)OC1=O]

The di-acid 30 (1 eq.) was dissolved in acetic anhydride (10 mL/mmol di-acid) at 80° C. The reaction was stirred 2 h at 80° C., cooled to rt and stirred overnight under an argon atmosphere. The volatiles were evaporated using an oil pump and a heating bath set to 65° C. Toluene (×3) was added to the residue and evaporated in vacuo. This afforded the anhydride 31.

¹H NMR (400 MHz, DMSO) δ 8.82 (d, J=6.5 Hz, 1H), 4.63-4.53 (m, 1H), 3.22 (dd, J=10.0=18.5 Hz, 2H), 2.82 (dd, J=5.8=18.5 Hz, 2H), 2.17 (t, J=6.7 Hz, 2H), 1.62-1.44 (m, 4H).

Compound 32

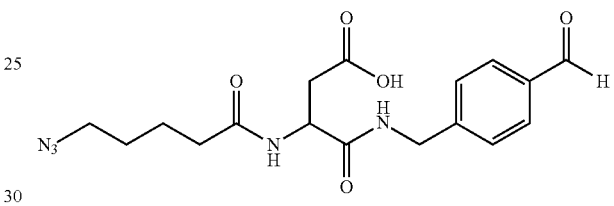

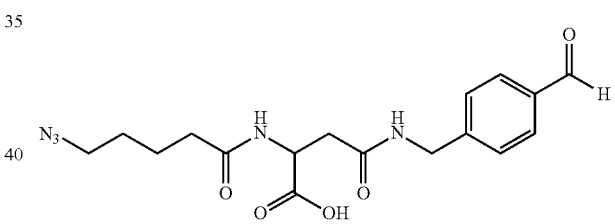

Mixture is Obtained

The amine (Simpson, M. G.; Pittelkow, M; Watson, S. P.; Sanders, J. K. M. *Org. Biomol. Chem.* 2010, 8, 1181-1187.) (1.2 eq) was dissolved in a mixture of DCM and THF (1:1, 6 mL/mmol anhydride). The anhydride 31 (1 eq) was added at 0° C. and the reaction was stirred overnight at rt. The solvent was evaporated and the residue taken up in EtOAc. The organic phase was washed with 1 M aq. HCl and brine, dried over MgSO₄ and concentrated in vacuo to afford the title compound 32.

¹H NMR (400 MHz, DMSO) δ 12.37 (br s, 2H), 9.98 (s, 2H), 8.59-8.42 (m, 2H), 8.21-8.07 (m, 2H), 7.89-7.80 (m, 4H), 7.51-7.39 (m, 4H), 4.66-4.48 (m, 2H), 4.40-4.30 (m, 4H), 2.74-2.64 (m, 2H), 2.59-2.50 (m, 2H), 2.20-2.09 (m, 4H), 1.61-1.43 (m, 8H).

Compound 33

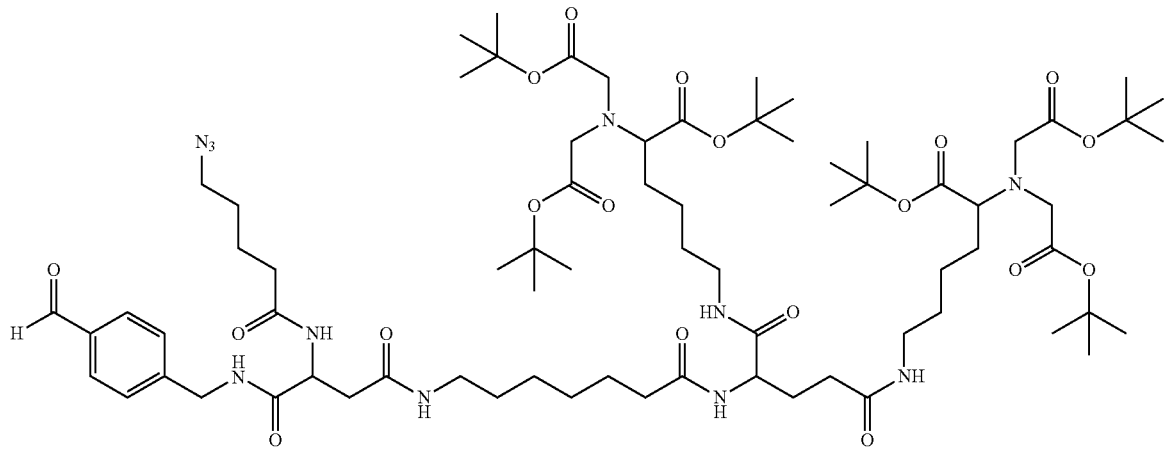 [SMILES: CC(C)(C)OC(=O)CN(CC(=O)OC(C)(C)C)C(CCCCNC(=O)CCC(NC(=O)CCCCCCNC(=O)CC(NC(=O)CCCCN=[N+]=[N-])C(=O)NCc1ccc(C=O)cc1)C(=O)NCCCCC(C(=O)OC(C)(C)C)N(CC(=O)OC(C)(C)C)CC(=O)OC(C)(C)C)C(=O)OC(C)(C)C]

HBTU (1.7 eq) was added to a mixture of amine 28 (1 eq), acid 32 (1.2 eq) and DIPEA (2 eq) in dry DMF (4 mL/mmol 28) under an argon atmosphere. The reaction mixture was stirred at rt overnight. The solvent was evaporated under reduced pressure and the residue dissolved in EtOAc. The organic phase was washed with sat. aq. NaHCO$_3$ (×2) and brine, dried over Na$_2$SO$_4$ and concentrated in vacuo. Flash column chromatography afforded the title compound.

Compound 34

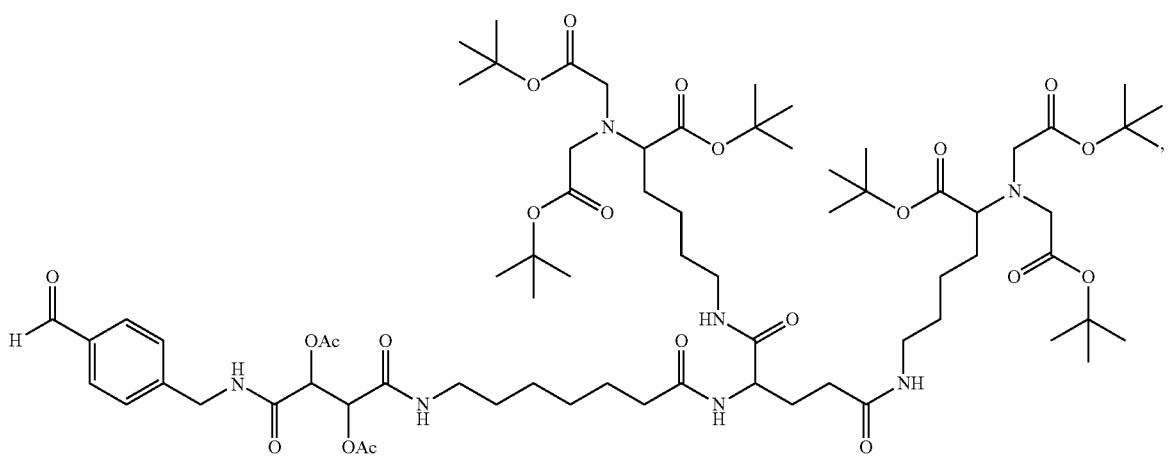

HBTU (1.7 eq) was added to a mixture of amine 28 (1 eq), acid 4 (1.2 eq) and DIPEA (2 eq) in dry DMF (4 mmol/mmol 28) under an argon atmosphere. The reaction mixture was stirred at rt overnight. The solvent was evaporated under reduced pressure and the residue dissolved in EtOAc. The organic phase was washed with sat. aq. NaHCO$_3$ (×2) and brine, dried over Na$_2$SO$_4$ and concentrated in vacuo. Flash column chromatography afforded the title compound.

$^1$H NMR (400 MHz, CDCl$_3$) δ 9.99 (s, 1H), 7.84 (d, J=8.0 Hz, 2H), 7.44 (d, J=8.0 Hz, 2H), 7.21 (d, J=6.6 Hz, 1H), 7.15 (t, J=6.6 Hz, 1H) 7.01 (t, J=6.9 Hz, 1H), 6.75 (t, J=6.6 Hz, 1H), 6.58 (t, J=5.6 Hz, 1H), 5.72 (d, J=3.2 Hz, 1H) 5.66 (d, J=3.2 Hz, 1H), 4.65-4.59 (m, 1H), 4.49-4.32 (m, 2H), 3.54-3.08 (m, 16H), 2.49-2.36 (m, 2H), 2.31-1.92 (m, 10H), 1.83-1.22 (m, 72H).

Compound 35

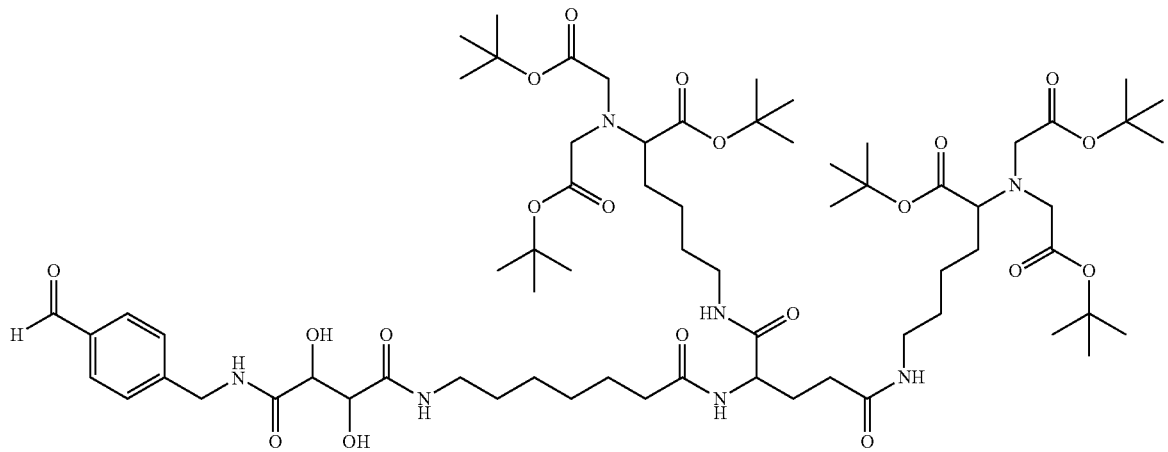

K$_2$CO$_3$ (1.5 eq) was added to a solution of 34 (1 eq) in MeOH (10 mL/mmol K) at 0° C. The reaction was stirred for 1 h at 0° C. The mixture was concentrated to a third of the solvent volume and filtered through a silica plug. Evaporation of the solvent afforded the titled compound.

$^1$H NMR (400 MHz, CDCl$_3$) δ 10.00 (s, 1H), 7.85 (d, J=7.9 Hz, 2H), 7.75-7.68 (m, 1H), 7.44 (d, J=7.9 Hz, 2H), 7.37-7.26 (m, 1H), 7.15 (d, J=6.3 Hz, 1H), 7.02-6.94 (m, 1H), 6.81-6.74 (m, 1H), 4.70-4.32 (m, 5H), 3.71-3.07 (m, 16H), 2.53-1.90 (m, 6H), 1.73-1.09 (m, 72H).

Compound 36

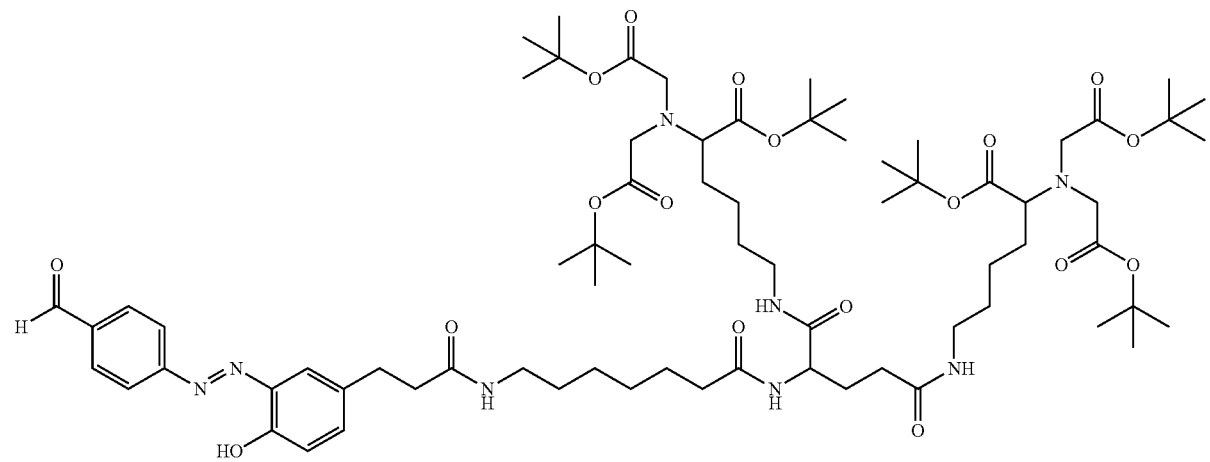 [SMILES: CC(C)(C)OC(=O)CN(CC(=O)OC(C)(C)C)C(CCCCNC(=O)CCC(NC(=O)CCCCCCNC(=O)CCc1ccc(O)c(/N=N/c2ccc(C=O)cc2)c1)C(=O)NCCCCC(C(=O)OC(C)(C)C)N(CC(=O)OC(C)(C)C)CC(=O)OC(C)(C)C)C(=O)OC(C)(C)C]

The NHS-ester 11 (2 eq) was added to a solution of the amine 28 (1 eq) in dry DCM (5 mL/mmol 28) at 0° C. The reaction was stirred at rt overnight. The solvent was evaporated and the residue taken up in EtOAc. The organic phase was washed with sat. aq. NaHCO$_3$ (×2) and brine. Flash column chromatography afforded the title compound.

$^1$H NMR (400 MHz, CDCl$_3$) δ (12.57 (s, 1H), 10.10 (s, 1H), 8.08-7.97 (m, 4H), 8.20 (s, 1H), 7.31-7.21 (m, 1H), 7.05-6.94 (m, 2H), 6.66-6.57 (m, 1H), 5.95-5.85 (1, H), 4.40-4.32 (m, 1H), 3.53-2.96 (m, 16H), 2.58-2.37 (m, 4H), 2.31-2.14 (m, 4H), 2.06-1.95 (m, 2H), 1.72-1.16 (m, 72H).

Compounds—General Procedure for Deprotection of the Carboxylates Tert Butyl Esters

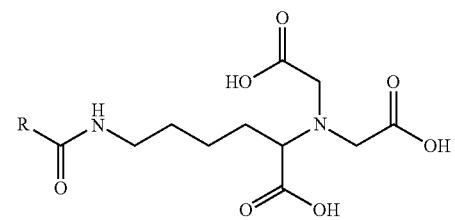

The tert butyl ester (1 eq) was dissolved in a mixture of TFA and dry DCM (3:1, 5 mL/mmol) under an argon atmosphere at rt. The reaction was stirred overnight. The volatiles were evaporated and the residue trituated in diisopropyl ether to afford the title compound.

R is a group as defined elsewhere herein.

The deprotected form of compound 35 is called compound 37:

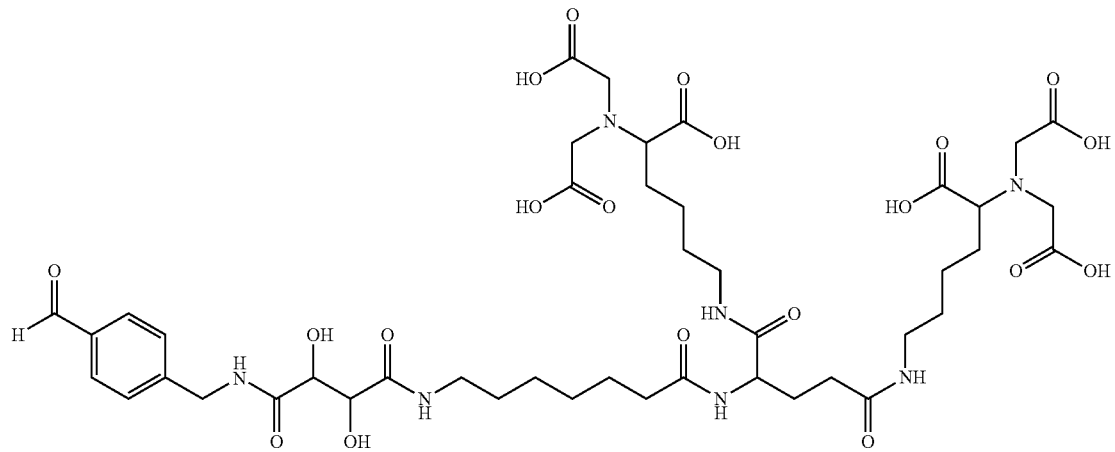 [SMILES: O=Cc1ccc(CNC(=O)C(O)C(O)C(=O)NCCCCCCC(=O)NC(CCC(=O)NCCCCC(C(=O)O)N(CC(=O)O)CC(=O)O)C(=O)NCCCCC(C(=O)O)N(CC(=O)O)CC(=O)O)cc1]

The deprotected form of compound 36 is called compound 38:

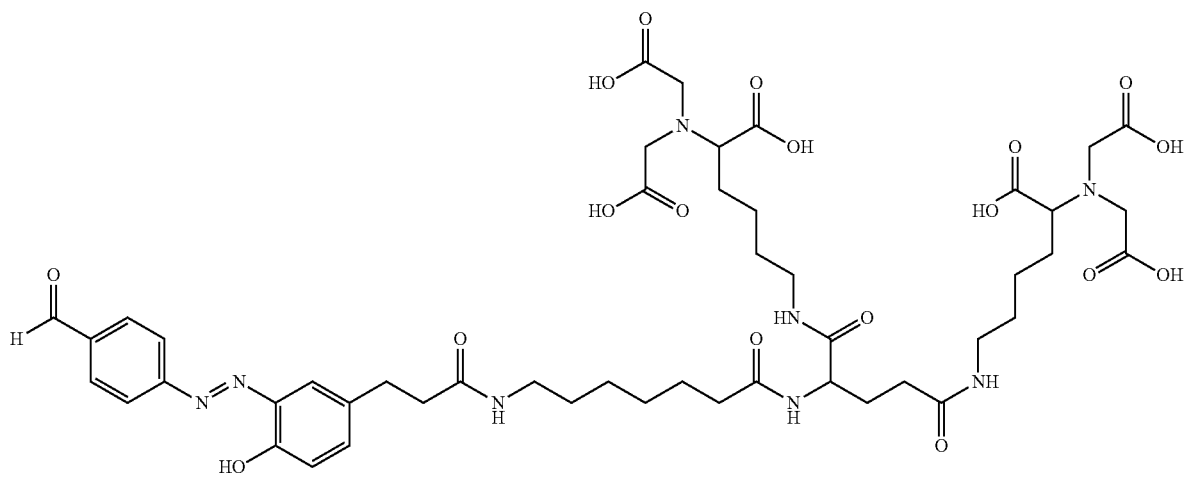 [SMILES: O=Cc1ccc(/N=N/c2cc(CCC(=O)NCCCCCCC(=O)NC(CCC(=O)NCCCCC(C(=O)O)N(CC(=O)O)CC(=O)O)C(=O)NCCCCC(C(=O)O)N(CC(=O)O)CC(=O)O)ccc2O)cc1]

General Procedure for Metal Directed Conjugation of Small Molecules to Metal Binding Proteins The conjugation reactions on his$_6$-tagged proteins, serotransferrin and antibodies were performed under nearly identical experimental conditions. All proteins and antibodies were used without further purification, except Trastuzumab, which was purified by Amicon filtration to remove non-protein components. The conjugation reactions were generally performed at a final concentration of protein on 2-7 µM.

DNA Templated Conjugation Reactions on his$_6$-Tagged Proteins, Metalloproteins and Murine IgG1

Conjugations were performed on his-tagged GFP, transferrin, anti-c-Myc, and Trastuzumab. Reactions were performed by mixing the small molecule (2-20 µM) with the protein of interest (2 µM), and CuSO$_4$ (4-40 µM) in a HEPES buffer (50 mM, pH 7.5) containing 100 mM NaCl and Tween®-20 (0.02 v/v %). Lastly NaCNBH$_3$ (50 mM) was added. The reaction mixture was left to react overnight at rt and before analysis by SDS-PAGE (4-12%), IEF-gel or purification by Amicon Ultra® centrifugal filters (MWCO 3000, 14100 g for 30 min) and Illustra Microspin G-25 spin columns (purchased from Sigma-Aldrich, US Biological or Roche).

Metal mediated coupling of 37 or 38 was performed on the proteins his$_6$-tagged GFP, Tf, Cmyc and Trastuzumab which is shown in FIG. 46. Each gel shows selective coupling in the presence of a directing metal in this case CuSO$_4$. This is seen by a band shift up on SDS-PAGE and a band shift down on a IEF-gel for lane 2.

Example 13

Site-Selective Insertion of a Bio-Orthogonal Handle on Proteins Using Metal-Mediated Small Molecule Labelling A reacting small molecules containing an aldehyde and two NTA-moieties was synthesized and conjugated to an antibody. After conjugation and purification, the linker was cleaved from the protein leaving either an aldehyde or an aniline (bioorthogonal handles) attached to the protein. The aldehyde was further conjugated to amino-oxy PEG with an average MW of 2000 or 5000 Da. The aniline is further conjugated to o-aminophenol PEG with an average MW of 10.000 Da.

Small Molecule Conjugation to Protein

The conjugation of the small molecule to the protein was performed according to example X2. The conjugates were purified by 3K spin filters (prewashed with buffer) and illustra Microspin G-25 columns.

Further Reactions of Protein Conjugates of Compound 37 (Dihydroxy Cleavable Linker)

The purified conjugate was reacted with $NaIO_4$ (1 mM) in NaOAc buffer with Tween-20 (pH 5.5, 100 mM) for 1 h at RT. Then excess reagents are removed and sample buffer exchanged by Illustra microspin G-25 spin columns into Phosphate buffer with Tween-20 (pH 6.5, 50 mM). Then aminooxy PEG5000 (1 mM) and para-phenylene diamine (2 mM) is added to the protein and the sample incubated over night at RT and analyzed by SDS PAGE (NuPAGE 4-12% bistris gel) and stained with Simply blue Safestain.

The small molecule 37 was coupled to $his_6$-tagged GFP by reductive amination as shown in FIG. 47. The dihydroxy linker was subsequently cleaved of by reaction with $NaIO_4$, which afforded an aldehyde modified GFP. The aldehyde modified GFP was further conjugated with either 2000PEG-$ONH_2$ or 5000PEG-$ONH_2$.

Further Reactions of Protein Conjugates of Compound 38 (Azobenzene-Cleavable Linker)

The purified conjugate was reacted with $Na_2S_2O_4$ (25 mM) in Phosphate buffer (pH 6.5, 25 mM) for 1 min at RT. Then excess reagents are removed and sample buffer exchanged by Illustra microspin G-25 spin columns into Phosphate buffer (pH 6.5, 25 mM). Then o-aminophenol-PEG10,000 (10 µM) and $K_3Fe(CN)_6$ (100 µM) is added to the protein and the sample incubated over night at RT and analyzed by SDS PAGE (NuPAGE 4-12% bistris gel) and stained with Simply blue Safestain.

Cleavage of the azobenzene cleavable linker after conjugation of 38 to Tf and further coupling with PEG to the cleaved conjugate is shown in FIG. 48. The gel shows that no cleavage and coupling occur for Tf alone, however, with the small molecule 38-GFP conjugate the small molecule is cleaved of using $Na_2S_2O_4$ leaving aniline-modified Tf. This results in a small gel shift. The aniline is further reacted with o-aminophenol-PEG10,000 as shown in lanes 7 and 9 resulting in significant gel shifts.

REFERENCES (BACKGROUND OF THE INVENTION)

1. Niemeyer, C. M. Semisynthetic DNA-protein conjugates for biosensing and nanofabrication. *Angew. Chem. Int. Ed.* 49, 1200-1216 (2010).
2. Stephanopoulos, N. & Francis, M. B. Choosing an effective protein bioconjugation strategy. *Nat. Chem. Biol.* 7, 876-884 (2011).
3. Corey, D. R. & Schultz, P. G. Generation of a hybrid sequence-specific single-stranded deoxyribonuclease. *Science* 238, 1401-1403 (1987).
4. Saghatelian, A., Guckian, K. M., Thayer, D. A. & Ghadiri, M. R. DNA detection and signal amplification via an engineered allosteric enzyme. *J. Am. Chem. Soc.* 125, 344-345 (2003).
5. Howorka, S., Cheley, S. & Bayley, H. Sequence-specific detection of individual DNA strands using engineered nanopores. *Nat. Biotechnol.* 19, 636-639 (2001).
6. Rabuka, D., Rush, J. S., deHart, G. W., Wu, P. & Bertozzi, C. R. Site-specific chemical protein conjugation using genetically encoded aldehyde tags. *Nat. Protoc.* 7, 1052-1067 (2012).
7. Kazane, S. A. et al. Site-specific DNA-antibody conjugates for specific and sensitive immuno-PCR. *Proc. Natl. Acad. Sci. U.S.A.* 109, 3731-3736 (2012).
8. Kazane, S. A. et al. Self-assembled antibody multimers through peptide nucleic acid conjugation. *J. Am. Chem. Soc.* 135, 340-346 (2013).
9. Netirojjanakul, C. et al. Synthetically modified Fc domains as building blocks for immunotherapy applications. *Chem. Sci.* 4, 266-272 (2013).
10. Barbuto, S. et al. Induction of innate and adaptive immunity by delivery of poly dA:dT to dendritic cells. *Nat. Chem. Biol.* 9, 250-256 (2013).
11. Keppler, A. et al. A general method for the covalent labeling of fusion proteins with small molecules in vivo. *Nat. Biotechnol.* 21, 86-89 (2003).
12. Los, G. V. et al. HaloTag: a novel protein labeling technology for cell imaging and protein analysis. *ACS Chem. Biol.* 3, 373-382 (2008).
13. Gautier, A. et al. An engineered protein tag for multi-protein labeling in living cells. *Chem. Biol.* 15, 128-136 (2008).
14. Niemeyer, C. M., Sano, T., Smith, C. L. & Cantor, C. R. Oligonucleotide-directed self-assembly of proteins: semisynthetic DNA-streptavidin hybrid molecules as connectors for the generation of macroscopic arrays and the construction of supramolecular bioconjugates. *Nucl. Acids Res.* 22, 5530-5539 (1994).
15. Tsukiji, S., Miyagawa, M., Takaoka, Y., Tamura, T. & Hamachi, I. Ligand-directed tosyl chemistry for protein labeling in vivo. *Nat. Chem. Biol.* 5, 341-343 (2009).
16. Hughes, C. C. et al. Marinopyrrole A target elucidation by acyl dye transfer. *J. Am. Chem. Soc.* 131, 12094-12096 (2009).
17. Uchinomiya, S.-H. et al. Site-specific covalent labeling of His-tag fused proteins with a reactive Ni(II)-NTA probe. *Chem. Commun.* 5880-5882 (2009).
18. Koshi, Y. et al. Target-specific chemical acylation of lectins by ligand-tethered DMAP catalysts. *J. Am. Chem. Soc.* 130, 245-251 (2008).
19. Meredith, G. D., Wu, H. Y. & Allbritton, N. L. Targeted protein functionalization using His-tags. *Bioconjugate Chem.* 15, 969-982 (2004).
20. Li, G. et al. Photoaffinity labeling of small-molecule-binding proteins by DNA-templated chemistry. *Angew. Chem. Int. Ed.* 52, 9544-9549 (2013).
21. Vinkenborg, J. L., Mayer, G. & Famulok, M. Aptamer-based affinity labeling of proteins. *Angew. Chem. Int. Ed.* 51, 9176-9180 (2012).

The invention claimed is:

1. A method for site selective conjugation of an oligonucleotide conjugate to a metal binding protein comprising a metal binding site, said method comprising:
providing a first oligonucleotide conjugate comprising a compound that comprises a reactive chemical group that reacts with a nucleophilic amino acid residue in the vicinity of said metal binding site of said metal binding protein
providing a second oligonucleotide conjugate that hybridizes to said first oligonucleotide conjugate and wherein said second oligonucleotide is conjugated to at least one ligand that binds to a metal at said metal binding site,
contacting said metal binding protein with said first oligonucleotide conjugate and said second oligonucleotide conjugate,
whereby hybridization of the first oligonucleotide conjugate to the second oligonucleotide conjugate and binding of the ligand to the metal binding site guides the reactive chemical group of the first oligonucleotide conjugate into proximity with the nucleophilic amino acid residue in a nucleophilic reaction between the nucleophilic amino acid residue and the reactive group of the first oligonucleotide conjugate, thereby conjugating the first oligonucleotide conjugate to the metal binding protein.

2. The method according to claim 1, wherein said metal binding site is a histidine cluster.

3. The method according to claim 1, wherein said metal binding protein is an IgG antibody comprising a histidine cluster, wherein said histidine cluster is located in the Fc region of the IgG antibody.

4. The method according to claim 1, wherein the nucleophilic amino acid residue is a lysine, cysteine or tyrosine.

5. The method according to claim 1, wherein the ligand comprises at least one of the molecules selected from the group consisting of iminodiacetic acid, pentetic acid, diethylene triamine pentaacetic acid (DPTA), ethylenediaminetetraacetic acid (EDTA), aminosalicyclic derivatives, 8-hydroxyquinoline, carboxymethylated amino acids, terpyridine and bis(2-pyridylmethyl) amine derivatives.

6. The method according to claim 1, wherein the ligand comprises at least one nitrilotriacetic acid (NTA) moiety.

7. The method according to claim 1, wherein the compound comprising the reactive group of the first oligonucleotide conjugate comprises an electrophile.

8. The method according to claim 7, wherein the compound comprising the reactive chemical group of the first oligonucleotide conjugate is N-hydroxysuccinimide.

9. The method according to claim 7, wherein the compound comprising the reactive chemical group of the first oligonucleotide conjugate is an aldehyde or a ketone in combination with a reducing agent.

10. The method according to claim 9, wherein said reducing agent is selected from the group consisting of sodium borohydride, sodium cyanoborohydride, sodium triacetoxyborohydride and decaborane.

11. The method according to claim 7, wherein the compound comprising the reactive chemical group of the first oligonucleotide conjugate is selected from the group consisting of reactive esters, N-hydroxysulfosuccinimide esters, N-hydroxyphthalimide esters, tetrafluorophenyl esters, p-nitrophenyl esters, thio-esters, phosphate esters, maleimides, isocyanates, isothiocyanates, acyl fluoride, imidoesters, aldehydes, ketones and 1-fluoro-2-nitrobenzenes.

12. The method according to claim 1, wherein the compound comprising the reactive chemical group is conjugated via a linker attached to the first oligonucleotide conjugate.

13. The method to according to claim 12, wherein said linker is an amine linker.

14. The method to according to claim 13, wherein said amine linker comprises the structure of Formula 4:

Formula 4

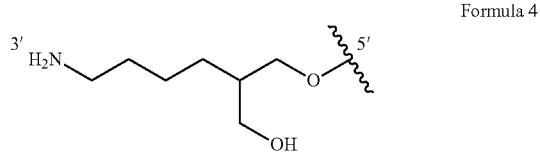 [SMILES: *OCC(CO)CCCCN]

15. The method according to claim 12, wherein said compound comprising the reactive chemical group is formed by reacting a linker having the structure of Formula 4:

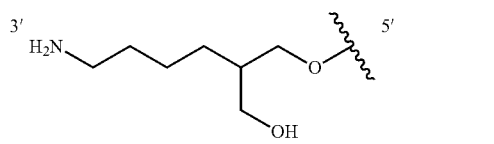 [SMILES: *OCC(CO)CCCCN]

with a homo-bifunctional linker.

16. The method according to claim 15, wherein said homo-bifunctional linker comprises the structure of Formula 5 or Formula 6:

Formula 5

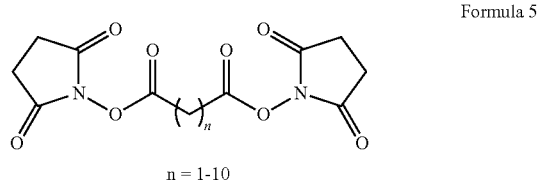

n = 1-10

Formula 6

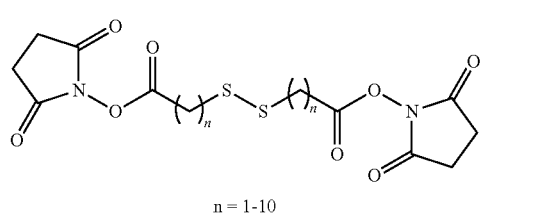

n = 1-10

17. The method according to claim 15, wherein said homo-bifunctional linker is selected from the group consisting of dimethyl adipimidate.2 HCl, dimethyl pimelimidate.2 HCl, dimethyl suberimidate.2 HCl, dimethyl 3,3'-dithiobispropionimidate.2 HCl, bis(succinimidyl) penta(ethylene glycol), bis(succinimidyl) nona(ethylene glycol), bis(sulfosuccinimidyl) suberate, Bis[2-(succinimidooxycarbonyloxy)ethyl]sulfone, disuccinimidyl glutarate, disuccinimidyl tartarate, 3,3'-dithiobis[sulfosuccinimidylpropionate], 4,4'-dithiobis[sulfosuccinimidylbutenoate], ethylene glycol bis[succinimidylsuccinate], tris-succinimidyl aminotriacetate, and 1,5-difluoro-2,4-dinitrobenzene.

18. The method according to claim 12, wherein said compound comprising the reactive chemical group is formed by reacting a linker having the structure of Formula 4:

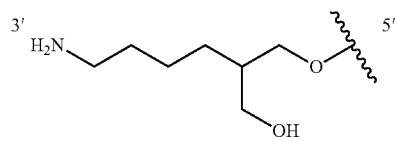 [SMILES: *OCC(CO)CCCCN]

with a hetero-bifunctional linker.

19. The method according to claim 18, wherein said hetero-bifunctional linker is selected from the group consisting of sulfosuccinimidyl (4-iodoacetyl) aminobenzoate, succinimidyl (4-iodoacetyl)aminobenzoate, succinimidyl 3-(bromoacetamido)propionate, succinimidyl iodoacetate, sulfosuccinimidyl 4-(N-maleimidomethyl)cyclohexane-1-carboxylate, 2-unit ethyleneglycol functionalized with succinimidyl and maleimido ends, 4-unit ethyleneglycol functionalized with succinimidyl and maleimido ends, 6-unit ethyleneglycol functionalized with succinimidyl and maleimido ends, 8-unit ethyleneglycol functionalized with succinimidyl and maleimido ends, 12-unit ethyleneglycol functionalized with succinimidyl and maleimido ends, 24-unit ethyleneglycol functionalized with succinimidyl and maleimido ends, succinimidyl 4-(N-maleimidomethyl)cyclohexane-1-carboxylate, succinimidyl 4-(N-maleimidomethyl)cyclohexane-1-carboxy-(6-amidocaproate), N-epsilon-maleimidocaproyl-oxysulfosuccinimide ester, N-epsilon-malemidocaproyl-oxysuccinimide ester, N-gamma-maleimidobutyryl-oxysulfosuccinimide ester, N-gamma-maleimidobutyryl-oxysuccinimide ester, N-kappa-maleimidoundecanoyl-oxysulfosuccinimide ester, m-maleimidobenzoyl-N-hydroxysulfosuccinimide ester, m-maleimidobenzoyl-N-hydroxysuccinimide ester, sulfosuccinimidyl 4-(p-maleimidophenyl)butyrate, succinimidyl 4-(p-maleimidophenyl)butyrate, N-alpha-maleimidoacetoxysuccinimide ester, N-beta meleimidopropyl-oxysuccinimide ester and succinimidyl 6-[(beta-maleimidopropionamido)hexanoate].

20. The method according to claim 1, wherein the oligonucleotide of the first oligonucleotide conjugate comprises at least 7 bases.

21. The method according to claim 1, wherein the oligonucleotide of the first oligonucleotide conjugate has the sequence 5'-ACATACAGCCTCGCATGAGCCC-3' (SEQ ID NO: 1).

22. The method according to claim 1, wherein the oligonucleotide of the second oligonucleotide conjugate comprises at least 7 bases.

23. The method according to claim 1, wherein the oligonucleotide of the second oligonucleotide conjugate has the sequence 5'-GGGCTCATGCGAGGCTTACGAAC-3' (SEQ ID NO: 2).

24. The method according to claim 1, wherein the ligand is conjugated via a linker to the second oligonucleotide.

25. The method according to claim 24, wherein said linker is an amine linker.
26. The method according to claim 25, wherein said amine linker comprises the structure of Formula 11:
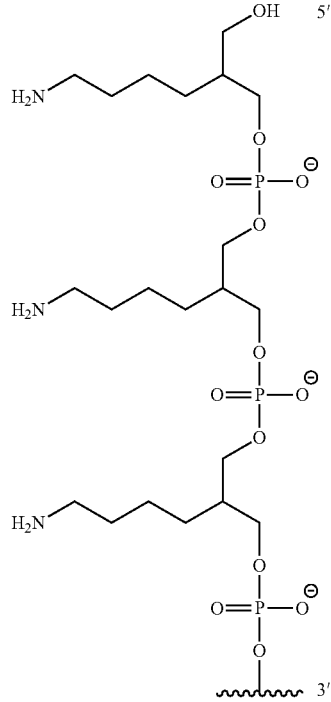
Formula 11
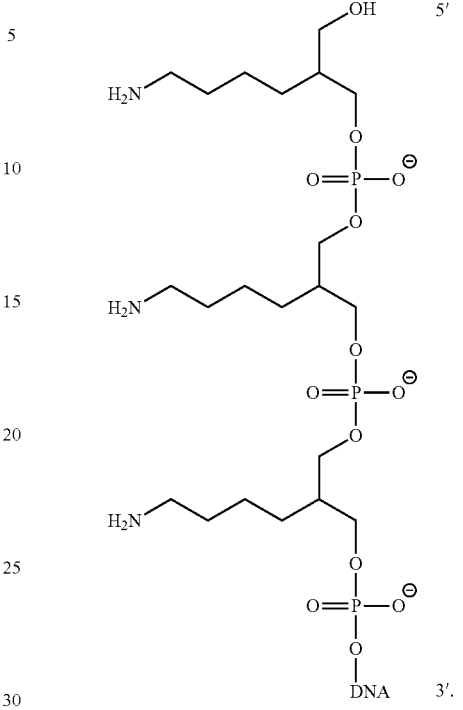
Formula 11
27. The method of claim 24, wherein the ligand and linker comprises the structure of formula 17:
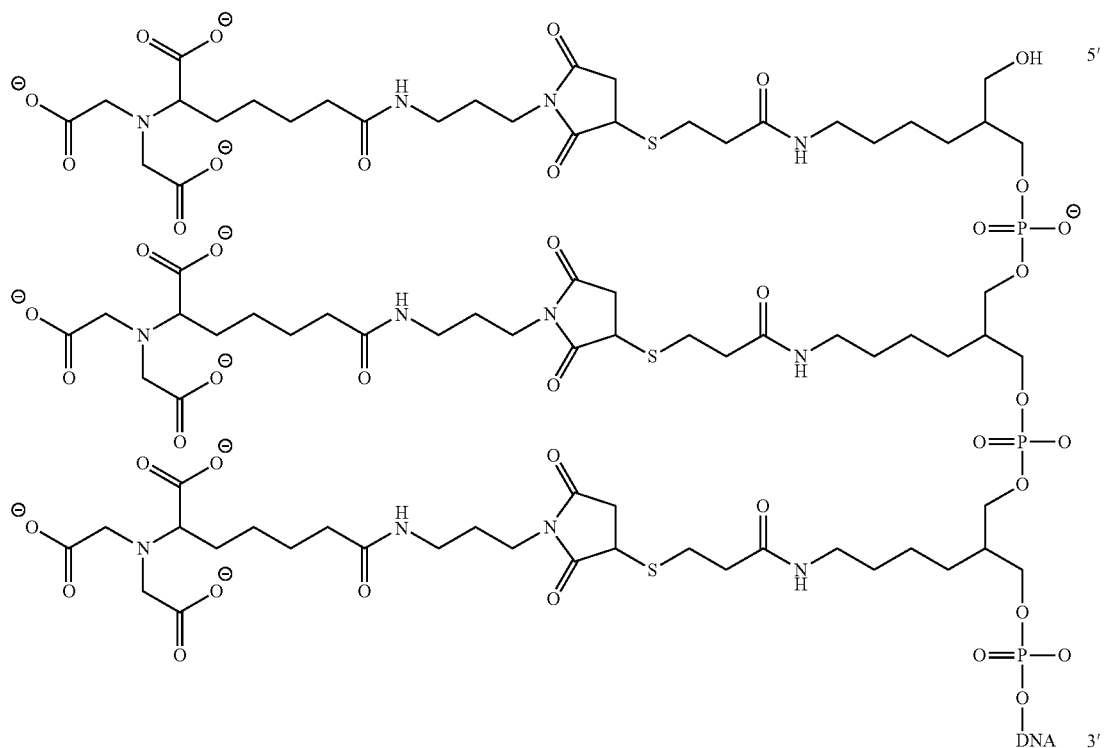
Formula 17

28. The method according to claim 24, wherein the ligand and linker comprises the structure of formula 19:

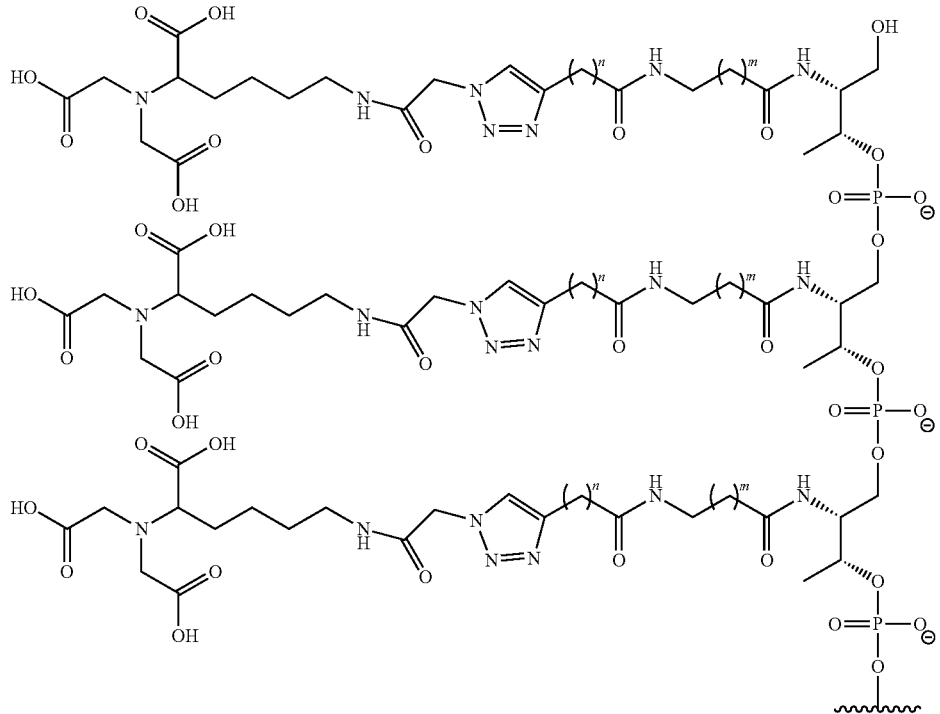

n = 1, 2, 3 or 4, m = 1, 2, 3 or 4

29. The method according to claim 1, wherein said first oligonucleotide conjugate comprises:
- a first linker comprising the reactive group, said reactive group being an aldehyde or a ketone,
- a second linker selected from the group consisting of $C_{1-20}$-alkane and $PEG_{1-20}$, and,
- a third linker which is a cleavable linker located between the second linker and the oligonucleotide of the first oligonucleotide conjugate,
- wherein said first linker, said second linker and said third linker are covalently linked.

30. The method according to claim 29, wherein said aldehyde or ketone of the first linker can react with an amine on the metal binding protein in the presence of a reducing agent by a reductive amination thereby linking the reactive group to the metal binding protein.

31. The method according to claim 29, wherein said second linker further comprises a functional chemical group selected from the group consisting of alkynes, azides, acetals, ketals, tetrazines and alkenes.

32. The method according to claim 29, wherein the third linker can be cleaved photochemically, by reduction, by oxidation, by bases, by acids, enzymatically and/or by fluoride.

33. The method according to claim 29, wherein said third linker is an oxidatively cleavable linker comprising the structure of Formula 7 or 8:

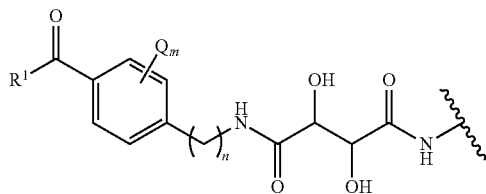

Formula 7

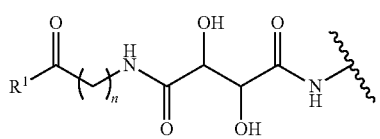

Formula 8 wherein
n is 1, 2, 3, 4, 5, 6, 7, 8, 9, 10, 11 or 12
m is 0, 1, 2, 3 or 4
$R^1$ is selected from the group consisting of —H, trifluoromethyl, aldehyde, —$C_{1-100}$-alk(en/yn)yl, —$C_{1-100}$-alkoxy, -acyloxy, -sulfhydryl, -nitro and -azide
Q is selected from the group consisting of —$C_{1-100}$-alk(en/yn)yl, —$C_{1-100}$-alkoxy, -acyloxy, -halogen, -cyano, -nitro, -carboxy, -acyl, -amino, -hydroxyl, -acyloxy, -amide, -sulfhydryl, -sulfoxide, -sulfone, -sulfonyl and -azide.

34. The method according to claim 29, wherein said third linker is a reducible cleavable linker comprising the structure of Formula 9 or 10:

Formula 9

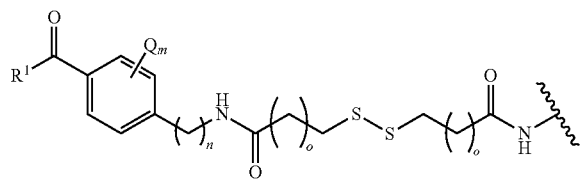

Formula 10

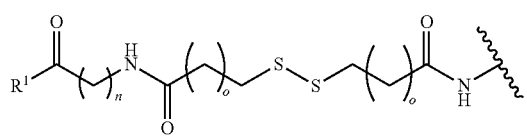

wherein
- n is 1, 2, 3, 4, 5, 6, 7, 8, 9, 10, 11 or 12
- m is 0, 1, 2, 3 or 4
- o is 1, 2, 3, 4, 5, 6, 7, 8, 9 or 10
- $R^1$ is selected from the group consisting of —$C_{1-100}$-alk(en/yn)yl, —$C_{1-100}$-alkoxy, -sulfhydryl, -nitro and -azide
- Q is selected from the group consisting —$C_{1-100}$-alk(en/yn)yl, —$C_{1-100}$-alkoxy, -halogen, -cyano, -nitro, -carboxy, -acyl, -amino, -hydroxyl, -acyloxy, -amide, -sulfhydryl, -sulfoxide, -sulfone, -sulfonyl and -azide.

35. A metal binding protein conjugate obtainable by the method according to claim 1.

36. The metal binding protein conjugate according to claim 35, wherein the metal binding site is a histidine cluster.

37. The metal binding protein conjugate according to claim 35, wherein said protein is an IgG antibody.

38. The metal binding protein conjugate according to claim 35, wherein the first oligonucleotide conjugate is conjugated to the metal binding protein within a radius of at most 3 nm from the metal binding site.

39. The metal binding protein conjugate according to claim 35, wherein the first oligonucleotide conjugate is conjugated to the protein via a cleavable linker.

40. The metal binding protein conjugate according to claim 35, wherein said protein conjugate comprises a cleavable linker that upon cleavage reveals a functional chemical group to which a fluorophore, a cytotoxic agent or a polymer can be conjugated.

41. The metal binding protein conjugate according to claim 40, wherein said fluorophore is selected from the group consisting of xanthenes, cyanines, squaraines, naphtalenes, coumarins, oxadiazoles, antracenes, pyrenes, oxazines, acridines, arylmethines and tetrapyrroles.

42. The metal binding protein conjugate according to claim 35, wherein said protein conjugate comprises a functional chemical group to which a cytotoxic agent can be conjugated.

43. The metal binding protein conjugate according to claim 42, wherein said cytotoxic agent is selected from the group consisting of toxins, antibiotics, radioactive isotopes and nucleolytic enzymes.

44. The metal binding protein conjugate according to claim 43, wherein the cytotoxic agent is a toxin selected from the group consisting of doxorubicin derivatives, maytansinoids, auristatins, calicheamicins, CC-1065, duocarmycins, azonatides, PBD dimers and antracyclines.

45. The metal binding protein conjugate according claim 42, wherein said protein conjugate is conjugated to a cytotoxic agent via a linker that is cleavable under reducing, oxidative, enzymatic, photochemical, basic or acidic conditions, or by fluoride.

\* \* \* \* \*